(12) United States Patent
Chan et al.

(10) Patent No.: US 11,154,436 B2
(45) Date of Patent: Oct. 26, 2021

(54) ABSORBENT ARTICLES WITH BIOCOMPOSTABLE PROPERTIES

(71) Applicant: Tethis, Inc., Raleigh, NC (US)

(72) Inventors: Ryan Nicholas Chan, Raleigh, NC (US); Gordon Sidney Cox, Durham, NC (US); Hailey Katherine Davis, Raleigh, NC (US); Vladimiro Nettel, Kirkland (CA)

(73) Assignee: TETHIS, INC., Raleigh, NC (US)

( * ) Notice: Subject to any disclaimer, the term of this patent is extended or adjusted under 35 U.S.C. 154(b) by 0 days.

(21) Appl. No.: 17/150,394

(22) Filed: Jan. 15, 2021

(65) Prior Publication Data

US 2021/0161732 A1  Jun. 3, 2021

Related U.S. Application Data

(63) Continuation of application No. 17/038,954, filed on Sep. 30, 2020, which is a continuation-in-part of application No. 16/592,948, filed on Oct. 4, 2019, now Pat. No. 10,980,912, which is a continuation-in-part of application No. 14/728,240, filed on Jun. 2, 2015, now Pat. No. 10,982,013.

(Continued)

(51) Int. Cl.
| | | |
|---|---|---|
| A61F 13/53 | (2006.01) |
| A61F 13/472 | (2006.01) |
| A61F 13/15 | (2006.01) |
| A61F 13/49 | (2006.01) |

(52) U.S. Cl.
CPC ........ *A61F 13/53* (2013.01); *A61F 13/15203* (2013.01); *A61F 13/472* (2013.01); *A61F 13/49* (2013.01); *A61F 2013/15422* (2013.01); *A61F 2013/530481* (2013.01)

(58) Field of Classification Search
CPC .. A61F 13/53; A61F 13/472; A61F 13/15203; A61F 2013/15422; A61F 2013/530481
See application file for complete search history.

(56) References Cited

U.S. PATENT DOCUMENTS

| | | |
|---|---|---|
| 4,590,081 A | 5/1986 | Sawada et al. |
| 5,176,669 A | 1/1993 | Klemp |

(Continued)

FOREIGN PATENT DOCUMENTS

| | | |
|---|---|---|
| WO | 2002074814 A1 | 9/2002 |
| WO | 2008022127 A2 | 2/2008 |

(Continued)

*Primary Examiner* — Ariana Zimbouski
(74) *Attorney, Agent, or Firm* — Neo IP

(57) ABSTRACT

Disclosed is an absorbent article with biocompostable properties, such as a feminine hygiene pad. Particularly, the present invention is directed to an absorbent sanitary article with a high degree of biocompostability. The sanitary article comprises, in one embodiment, at least a top layer, a back layer, and absorbent core, wherein the absorbent core includes a superabsorbent polymer, and wherein at least the superabsorbent polymer is biocompostable. The absorbent article exhibits improved biocompostable properties and performance comparable to non-biodegradable absorbent articles which include non-biodegradable superabsorbent polymers.

20 Claims, 18 Drawing Sheets

Related U.S. Application Data

(60) Provisional application No. 62/006,317, filed on Jun. 2, 2014.

(56) References Cited

U.S. PATENT DOCUMENTS

| | | | |
|---|---|---|---|
| 5,599,916 | A | 2/1997 | Dutkiewicz et al. |
| 7,459,501 | B2 | 12/2008 | Doane et al. |
| 8,383,573 | B2 | 2/2013 | Dupont et al. |
| 8,461,129 | B2 * | 6/2013 | Bolduc .................. A61L 15/28 514/54 |
| 8,507,607 | B2 | 8/2013 | Chambers |
| 8,563,466 | B2 | 10/2013 | Chevigny et al. |
| 8,710,212 | B2 | 4/2014 | Thibodeau et al. |
| 8,907,155 | B2 | 12/2014 | Wang et al. |
| 10,183,094 | B2 | 1/2019 | Yamaguchi et al. |
| 2005/0214541 | A1 | 9/2005 | Berrada et al. |
| 2008/0177057 | A1 | 7/2008 | Bolduc et al. |
| 2010/0057027 | A1 | 3/2010 | Furno et al. |
| 2010/0179497 | A1 | 7/2010 | Brownlee |
| 2011/0152814 | A1 | 6/2011 | Seneviratne |
| 2011/0184366 | A1 | 7/2011 | Carbonari et al. |
| 2011/0319849 | A1 | 12/2011 | Collias et al. |
| 2012/0052037 | A1 | 3/2012 | Sivik et al. |
| 2012/0121519 | A1 | 5/2012 | Thomaides et al. |
| 2012/0310190 | A1 | 12/2012 | Lavon et al. |
| 2014/0309606 | A1 | 10/2014 | Richlen et al. |
| 2015/0352520 | A1 | 12/2015 | Suarez-Hemandez |
| 2017/0002098 | A1 * | 1/2017 | Ayoub .................... A61L 15/60 |
| 2017/0021051 | A1 | 1/2017 | Richards et al. |
| 2017/0056253 | A1 | 3/2017 | Chester et al. |
| 2017/0224540 | A1 | 8/2017 | Li et al. |
| 2017/0281423 | A1 * | 10/2017 | Panayotova ............ A61L 15/60 |
| 2018/0153746 | A1 | 6/2018 | Sookraj |
| 2018/0289734 | A1 | 10/2018 | Benedictis et al. |
| 2018/0371309 | A1 | 12/2018 | Chan et al. |
| 2019/0111176 | A1 | 4/2019 | Serna |
| 2019/0330383 | A1 | 10/2019 | Aoki et al. |
| 2020/0054782 | A1 | 2/2020 | Chan et al. |
| 2020/0138642 | A1 | 5/2020 | Wagner et al. |
| 2020/0147258 | A1 | 5/2020 | Galabura et al. |

FOREIGN PATENT DOCUMENTS

| | | |
|---|---|---|
| WO | 2009012284 A1 | 1/2009 |
| WO | 2013096891 A9 | 8/2013 |
| WO | 2013180643 A1 | 12/2013 |
| WO | 2012064741 A3 | 4/2014 |

* cited by examiner

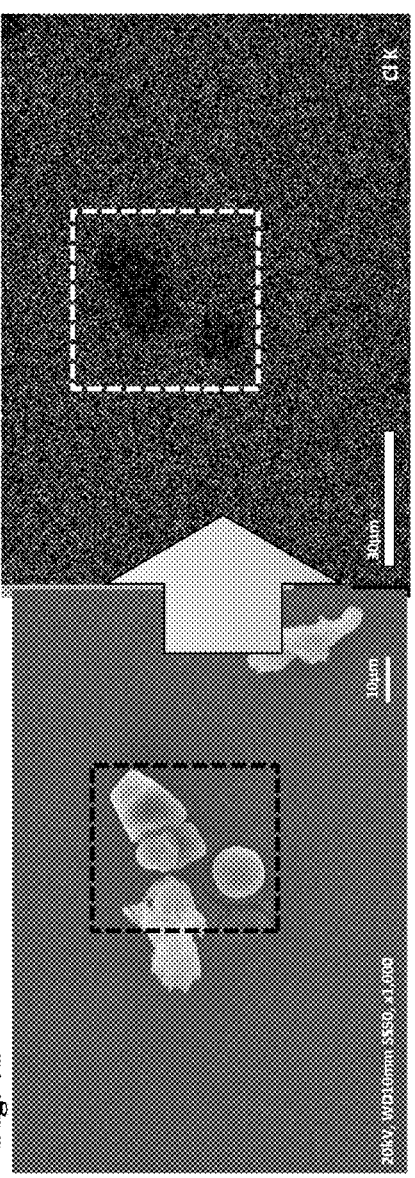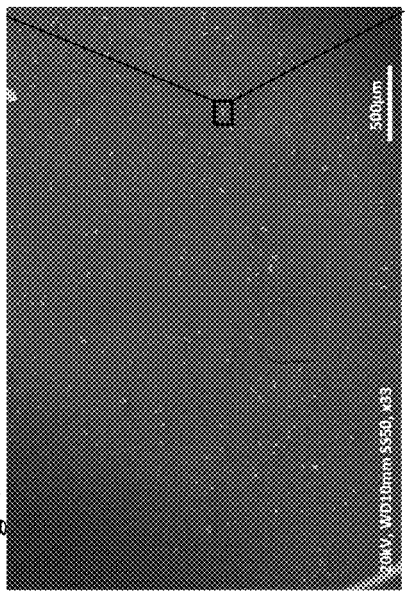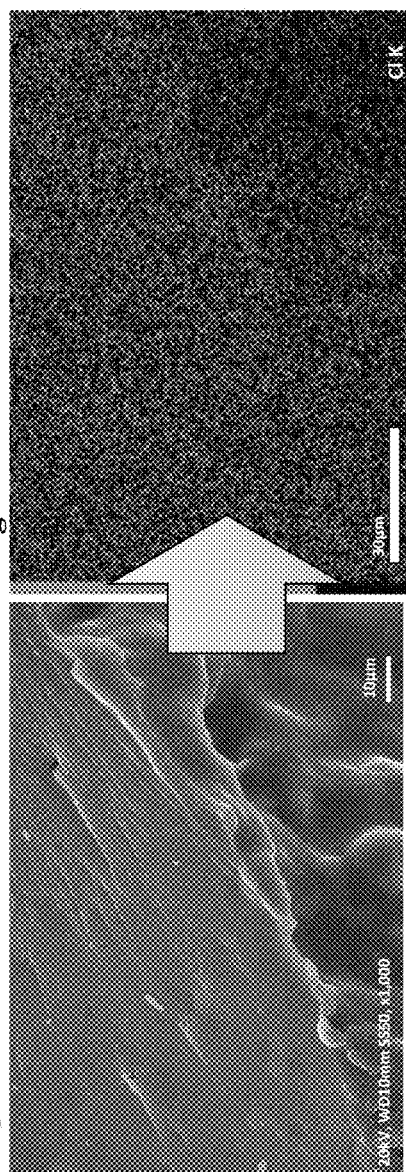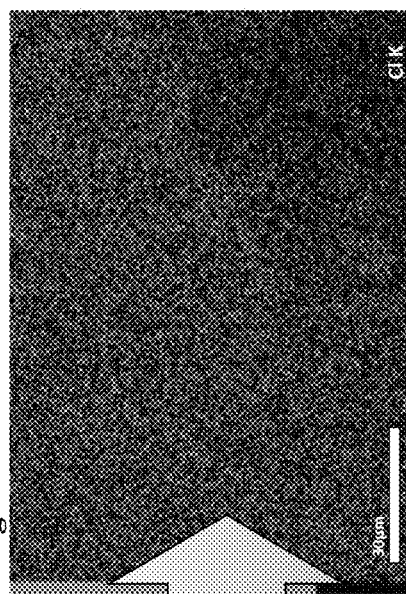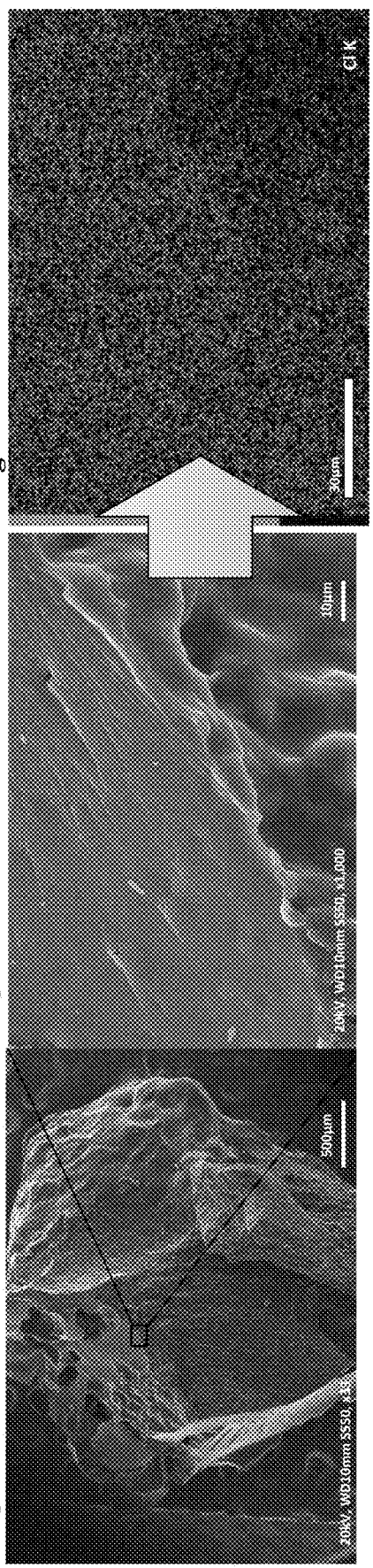
Fig. 7A Fig. 7B Fig. 7C Fig. 7D Fig. 7E Fig. 7F

ABSORBENT ARTICLES WITH BIOCOMPOSTABLE PROPERTIES

CROSS REFERENCE TO RELATED APPLICATIONS

This application relates to and claims priority from the following applications. This application is a continuation of U.S. application Ser. No. 17/038,954, filed Sep. 30, 2020, which is a continuation-in-part of U.S. application Ser. No. 16/592,948, filed Oct. 4, 2019, which is a continuation-in-part of U.S. application Ser. No. 14/728,240, filed Jun. 2, 2015, which claims the benefit of U.S. Provisional patent Application No. 62/006,317, filed Jun. 2, 2014. Each of the above-mentioned applications is incorporated herein by reference in its entirety.

BACKGROUND OF THE INVENTION

1. Field of the Invention

The present invention generally relates to sanitary articles with biocompostable properties, including disposable baby diapers, adult incontinence products, and menstrual pads. Particularly, the present invention relates to sanitary articles with elements that include high bioderived content, including absorbent cores with superabsorbent properties and high biocompatibility.

2. Description of the Prior Art

Sanitary absorbent articles are used for a variety of hygienic purposes, including infant and adult incontinence and menstruation. Articles are traditionally constructed with a variety of layers that aid in the distribution and absorption of fluids while providing comfort to a user. Often, the hygienic articles are constructed with layers and absorbent materials, such as superabsorbent polymers (SAPs), that are synthetically derived, are non-biodegradable, and are non-biocompostable.

Consumers have expressed an increased desire for biodegradability and/or biocompostability in absorbent sanitary articles. As such, biopolymers and bio-derived polymers for integration in the absorbent articles have been examined for their absorbency properties, including naturally occurring materials and their derivatives, such as starches, celluloses, and polysaccharides. However, these biopolymers are often more difficult to synthesize, more expensive to make, and have inferior absorption properties relative to traditional, non-biocompostable materials, such as polyacrylates.

Examples of relevant prior art documents include the following:

U.S. Patent Publication No. 20180153746 for "Biodegradable sanitary articles with higher biobased content" by inventor Sookraj, filed Dec. 6, 2016, and published Jun. 7, 2018, is directed to sanitary articles such as disposable diapers, adult incontinent pads, feminine hygiene products, and sanitary napkins comprised of biodegradable polymers with higher biobased content. The sanitary articles include a topsheet, an absorbent core, and a backsheet. The topsheet is comprised of biodegradable polyester polyol polymer foam which may be configured to wick liquid away from a wearer's body and may be impregnated with superabsorbent polymer. The absorbent core may be comprised of superabsorbent polymer including a cross-linked and/or partially neutralized polyacrylic acid polymer, cross-linked polyacrylic acids or cross-linked starch-acrylic acid graft polymers. The backsheet may be comprised of poly-lactone polymers having generally hydrophobic characteristics. In preferred embodiments, the polymeric materials comprising the topsheet, absorbent core, and backsheet are formed from raw materials with high biobased content.

U.S. Patent Publication No. 20170021051 for "Biodegradable Absorbent Articles" by inventor Richards, et al., filed Jul. 15, 2016, and published Jan. 26, 2017, is directed to a biodegradable, disposable absorbent article, such as a diaper, having a non-woven inner layer of natural fibers and a non-woven outer layer of natural fibers and a treatment applied to at least one surface thereof. The treatment includes at least one compound selected from the group consisting of waxes, urethanes, silicones, fluorocarbons, and non-fluorochemical repellents. The absorbent article has a core of natural fibers or fibrous material, and optionally polyacrylate superabsorbent particles, positioned between the inner layer and the outer layer. The article may contain polylactic acid films between the layers.

U.S. Patent Publication No. 20170224540 for "Biodegradable, biobased diaper" by inventors Li, et al., filed Aug. 8, 2015, and published Aug. 10, 2017, for a disposable diaper that is biobased and/or biodegradable. The diaper is either made of wholly or partially renewable resources, at the same time can decompose in a compost site, and biodegrade in a conventional landfill as well as in marine conditions such as fresh, brackish or salt water.

WIPO Publication No. WO2012064741 for "Method for the production of substituted polysaccharides via reactive extrusion" by inventors Hanna, et al., filed Nov. 8, 2011 and published May 18, 2012, is directed to a reactive extrusion process for the production of substituted polysaccharides, in particular, cellulose acetate, starch acetate, carboxymethyl cellulose, and carboxymethyl starch.

U.S. Pat. No. 8,710,212 for "Starch networks as absorbent or superabsorbent materials and their preparation by extrusion" by inventors Thibodeau, et al., filed Mar. 26, 2004 and issued Apr. 29, 2014, is directed to an absorbent material consisting of a molecular network of starch molecules, the starch molecules comprising an amylopectin content of at least 90% (w/w). The molecular network can either be comprised of self-entangled starches or cross-linked starches.

WIPO Publication No. WO2013096891 for "Algal thermoplastics, thermosets, paper, adsorbants and absorbants" by inventors Harlin, et al., filed Dec. 21, 2012 and published Jun. 27, 2013, is directed to biomass-based materials and valuable uses of microalgal biomass including: (i) acetylation of microalgal biomass to produce a material useful in the production of thermoplastics; (ii) use of triglyceride containing microalgal biomass for production of thermoplastics; (iii) combination of microalgal biomass and at least one type of plant polymer to produce a material useful in the production of thermoplastics; (iv) anionization of microalgal biomass to form a water absorbant material; (v) cationization of microalgal biomass, and optional flocculation, to form a water absorbant material; (vi) crosslinking of anionized microalgal biomass; (vii) carbonization of microalgal biomass; and (viii) use of microalgal biomass in the making of paper.

WIPO Publication No. WO2013180643 for "A fiber-based substrate provided with a coating based on a biopolymer material and a method of producing it" by inventors Johansson, et al., filed May 31, 2013 and published Dec. 5, 2013, is directed to a coated product, comprising a substrate and a coating layer, wherein said substrate is in shape of a web, sheet or tray of fiber-based material such as paper or paperboard, and wherein said coating layer forms a barrier on the substrate and mainly contains biopolymer material cross-linked by a cross-linking agent, wherein the cross-linking agent is citric acid in a range of 14-50 pph, and the biopolymer material is diesterified and hydrolyzed to an extent of less than 80%, preferably less than 50% and most preferred less than 30%.

WIPO Publication No. WO2008022127 for "Process for producing biopolymer nanoparticles" by inventors Wildi, et al., filed Aug. 14, 2007 and published Feb. 21, 2008, is directed to a process for producing a biopolymer nanoparticles product. In this process, biopolymer feedstock and a plasticizer are fed to a feed zone of an extruder having a screw configuration in which the feedstock is processed using shear forces in the extruder, and a crosslinking agent is added to the extruder downstream of the feed zone. The biopolymer feedstock and plasticizer are preferably added separately to the feed zone. The screw configuration may include two or more steam seal sections. Shear forces in a first section of the extruder may be greater than shear forces in an adjacent second section of the extruder downstream of the first section. In a post reaction section located after a point in which the crosslinking reaction has been completed, water may be added to improve die performance.

U.S. Pat. No. 5,599,916 for "Chitosan salts having improved absorbent properties and process for the preparation thereof" by inventors Dutkiewicz, et al., filed Dec. 22, 1994 and issued Feb. 4, 1997, is directed to a method for producing a water-swellable, water-insoluble chitosan salt having improved absorption properties. The method involves forming a mixture of a chitosan, water, an acid, and, optionally, a crosslinking agent, recovering the formed chitosan salt from the mixture and, optionally, treating said recovered chitosan salt with heat or under humid conditions.

U.S. Pat. No. 4,590,081 for "Method of manufacturing foamed foodstuff" by inventors Sawada, et al., filed Mar. 1, 1984 and issued May 20, 1986, is directed to a method of manufacturing a foamed foodstuff by inserting powdered and granular ingredients for a foodstuff into an extruder which is provided with two screws which mesh with each other and rotated at high speed in the same direction, mixing and heating the ingredients in a preheating zone, adding a predetermined quantity of a liquid to the mixed ingredients in a liquid-addition zone, kneading the moistened ingredients in a kneading zone, transforming the starch in the ingredients into alpha starch in an alpha formation zone, and then extruding the ingredients from the extruder.

WIPO Publication No. WO2002074814 for "Batch cookable modified high amylose starches and their use in paper sizing applications" by inventors Billmers, et al., filed Mar. 16, 2001 and published Sep. 26, 2002, is directed to pregelatinized modified, high amylose starches that are batch cookable to a uniform, substantially particle-free dispersion at atmospheric pressures and the process of preparing such starches in an extruder. Such pregelatinized, modified, high amylose starches are useful in a variety of applications without the need for jet cooking. In addition, such starches are readily dispersible at high solids to provide uniform formulations and are substantially non-retrograded. Further, such starches provide improved surface sizing agents which use results in the preparation of paper which is characterized by improved water resistance, reduced porosity, and other size properties.

U.S. Pat. No. 8,383,573 for "Dual character biopolymer useful in cleaning products" by inventors Dupont, et al., filed Nov. 18, 2009 and issued Feb. 26, 2013, is directed to new cleaning compositions including novel amphoteric dispersant polymers containing anionic and nitrogen containing substitution are disclosed. In particular, cleaning compositions containing modified polysaccharides having anionic and nitrogen containing substitution and methods of forming the same are disclosed.

U.S. Publication No. 20120121519 for "Natural polymeric emulsifiers and method for use" by inventors Thomaides, et al., filed Nov. 7, 2011 and published May 17, 2012, is directed to polymeric emulsifiers including polysaccharides modified with at least one cross-linking reagent and with from about 1 mol % to about 10 mol % of at least one ionic reagent, methods for preparing the same, and emulsions including the polymeric emulsifiers.

SUMMARY OF INVENTION

The present invention relates to modified biopolymers, including charge-modified biopolymers, crosslinked biopolymers, and/or crosslinked, charge-modified biopolymers. In particular, the present invention relates to modified biopolymers used as superabsorbent polymers. Methods of producing and using a modified biopolymer of the present invention are also provided.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 7A shows a Scanning Electron Microscope (SEM) image of a commercially available cationic starch at 33× magnification.

FIG. 7B shows a SEM image of the commercially available cationic starch at 1000× magnification.

FIG. 7C shows a SEM image of an Energy Dispersive X-ray Spectrometry (EDS) chlorine map of the commercially available cationic starch.

FIG. 7D shows a SEM image of a cationic starch prepared according to methods of the present invention at 33× magnification.

FIG. 7E shows a SEM image of the cationic starch prepared according to methods of the present invention at 1000× magnification.

FIG. 7F shows a SEM image of an EDS chlorine map of the cationic starch prepared according to methods of the present invention.

DETAILED DESCRIPTION

Figure 1A:
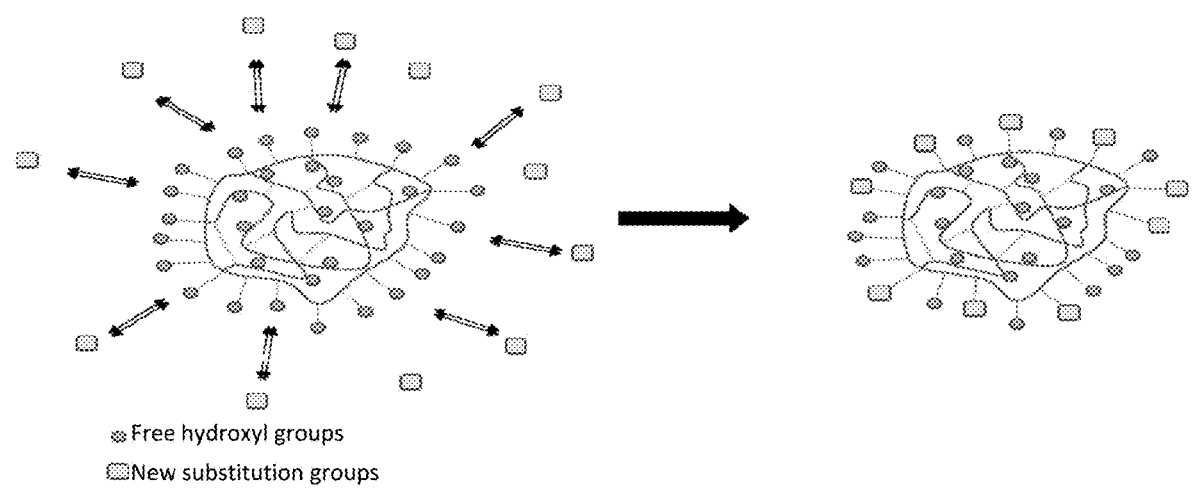
FIG. 1A is a schematic of a heterogeneous phase reaction.

The present invention is generally directed to sanitary articles with biocompostable elements. In general, this includes articles with a series of layers, including a top layer, a back layer, and an absorbent core, wherein the absorbent core preferably integrates modified biopolymers, including charge-modified biopolymers, crosslinked biopolymers, and/or crosslinked, charge-modified biopolymers. In particular, the invention incorporates modified biopolymers used as superabsorbent polymers. Particularly, the superabsorbent polymer includes a high degree of bioderived content and is preferably biocompostable. Methods of producing and using a modified biopolymer of the present invention are also provided.

Superabsorbent polymers are crosslinked hydrophilic polymers that absorb and retain large amounts of liquids. In general, superabsorbent polymers are able to absorb and retain at least 10 times their weight of a 0.9% NaCl solution, also referred to as a "saline solution" throughout the present application. Due to their ability to absorb liquids, superabsorbent polymers are often used in absorbent articles (e.g., diapers, incontinence products, feminine hygiene products, wound dressings).

Most superabsorbent polymers are formed of polyacrylates, which are formed from monomers (e.g., acrylic acid, acrylamide) obtained from non-renewable sources. However, polyacrylates are generally not biodegradable. Additionally, polyacrylates often contain some residual monomers, which may be toxic or cause allergic contact dermatitis.

In one embodiment, the present invention is directed to a biocompostable absorbent sanitary article, including a fluid-permeable top layer, a fluid-resistant back layer, and an absorbent core, wherein the absorbent core includes a superabsorbent polymer (SAP), wherein the SAP includes a modified starch-based biopolymer, wherein the SAP is biocompostable, and wherein the biobased carbon content of the SAP is at least approximately 50%. In one embodiment, the SAP does not include a synthetic polymer. In another embodiment, the biobased carbon content of the SAP is between approximately 60% and approximately 95%. In yet another embodiment, the biobased carbon content of the SAP is between approximately 80% and approximately 90%. In yet another embodiment, the biobased carbon content of the SAP is between approximately 84% and approximately 90%. In another embodiment, the biocompostable absorbent sanitary article includes an acquisition distribution layer (ADL), wherein the ADL is operable to wick and distribute fluid from the fluid-permeable top layer to the absorbent core. In another embodiment, the SAP is further integrated into the fluid-permeable top layer. In another embodiment, the fluid-permeable top layer, the fluid-resistant back layer, and/or the absorbent core are biocompostable. In another embodiment, the amylose content of the modified starch-based biopolymer is less than about 85% w/w. In another embodiment, the SAP has a centrifuge retention capacity (CRC) of at least about 12 g/g or an absorbency under load (AUL) at 0.7 psi of at least about 8 g/g in a saline solution. In another embodiment, the SAP exhibits no cytotoxicity and is not a dermal irritant. In another embodiment, the SAP exhibits over 40% degradation in 60 days and 60% degradation in 90 days relative to an analytical grade cellulose control. In another embodiment, at least about 95% of the particle sizes of the SAP are between about 150 micrometers (about 0.00394 inches) and about 850 micrometers (about 0.0256 inches). In another embodiment, the article is one of: a baby diaper, an adult incontinence product, or a menstrual pad. In another embodiment, the biobased carbon content of the SAP is at least about 80%.

In another embodiment, the present invention is directed to a biocompostable absorbent sanitary article including a fluid-permeable top layer, a fluid-resistant back layer, and an absorbent core, wherein the absorbent core includes a superabsorbent polymer (SAP) and absorbent fiber, wherein the SAP includes a modified biopolymer, and wherein the amylose content of the modified biopolymer is less than about 80% w/w. In one embodiment, the article includes at least an intermediate layer, wherein the intermediate layer does not include the SAP. In another embodiment, the SAP is biocompostable such that the SAP is operable to exhibit at least 90% degradation within 180 days when compared to analytical grade cellulose in a test directed by ASTM D5338 or an equivalent biodegradation test. In another embodiment, the article includes at least one adhesive between layers of the biocompostable absorbent sanitary article, and/or an external adhesive, wherein the at least one adhesive and/or the external adhesive are biocompostable such that the at least one adhesive and/or the external adhesive is operable to exhibit at least 90% degradation within 180 days relative to an analytical grade cellulose control. In another embodiment, the article is constructed from at least 75% biobased carbon content. In another embodiment, the absorbent core is folded at least once such that the absorbent core forms a central longitudinal channel and/or such that the absorbent core forms two or more layers. In another embodiment, the modified biopolymer includes a modified starch-based biopolymer made from corn starch, potato starch, pea starch, and/or tapioca starch. In another embodiment, ethanol is not used in a charge modification step of an extrusion process in making the SAP. Alternatively, no type of alcohol is used in a charge modification step of an extrusion process in making the SAP. In another embodiment, biobased carbon content of the SAP is at least 80%. In another embodiment, the SAP has a free swell capacity (FSC) of at least 25 g/g in a 0.9% saline solution, a centrifuge retention capacity (CRC) of at least about 16 g/g in a 0.9% saline solution, and an absorbency under load (AUL) at 0.7 psi of at least about 6 g/g in a 0.9% saline solution.

Another embodiment of the present invention is directed to a biocompostable absorbent sanitary article, including a fluid-permeable topsheet, a fluid-resistant backsheet, an acquisition distribution layer, and an absorbent core, wherein the absorbent core includes at least cellulose fluff pulp and an integrated superabsorbent polymer (SAP), and wherein the SAP includes a modified biopolymer, and wherein the SAP is biocompostable such that the SAP is operable to exhibit at least 90% degradation within 180 days when compared to a cellulose control.

Yet another embodiment of the present invention is directed to a biocompostable absorbent sanitary article, including a fluid-permeable top layer, a fluid-resistant back layer, and a superabsorbent polymer (SAP), wherein the SAP includes a modified biopolymer, and wherein the SAP is biocompostable such that the SAP is operable to exhibit at least 90% degradation within 180 days when compared to a cellulose control. In one embodiment, the article includes an absorbent core without fluff. In another embodiment, the SAP has a free swell capacity (FSC) of at least about 13 g/g in defibrinated sheep's blood or a centrifuge retention capacity (CRC) of at least about 12 g/g in defibrinated sheep's blood.

Referring now to the drawings in general, the illustrations are for the purpose of describing one or more preferred embodiments of the invention and are not intended to limit the invention thereto.

The present invention describes a modified biopolymer (e.g., a charge-modified biopolymer, a crosslinked biopolymer, and/or a crosslinked, charge-modified biopolymer), methods of producing the modified biopolymer, and articles containing the modified biopolymer. In one embodiment, the crosslinked, charged-modified biopolymer is formed of one biopolymer that has been charge-modified and then crosslinked. In another embodiment, the crosslinked, charged-modified biopolymer is formed of at least two different biopolymers that are crosslinked and at least one of the biopolymers has been charge-modified. In another embodiment, the at least two different biopolymers are crosslinked with each other. In yet another embodiment, a crosslinked, charge-modified biopolymer is formed of two different biopolymers that are crosslinked and both of the biopolymers are charge-modified.

A "biopolymer" as used herein refers to a polymer that has at least one free amine and/or hydroxyl group present on a majority of the monomeric units of the polymer and is a polymer produced by a living organism or a derivative thereof, or is a synthetic version of this polymer produced by abiotic chemical routes. In one embodiment, a free amine and/or hydroxyl group is present on each of the monomeric units of the polymer backbone. Exemplary biopolymers include, but are not limited to, proteins and/or polysaccharides. As one of ordinary skill in the art will understand, a biopolymer may be synthetically obtained (e.g., through laboratory synthesis) and/or obtained and/or derived from nature (e.g., from a living or previously living organism). In one embodiment, the biopolymer is the same as a polymer found in nature (i.e., a native biopolymer) or is a derivative thereof. In another embodiment, the biopolymer is a derivative of a polymer produced by a living organism, the derivative caused by the synthetic method used to obtain or isolate the biopolymer from nature. In yet another embodiment, the biopolymer is a polymer produced by bacteria and/or microbes.

Further exemplary biopolymers include, but are not limited to, starches (including amylose and/or amylopectin), chitosans, hemicelluloses, lignins, celluloses, chitins, alginates, dextrans, pullanes, polyhydroxyalkanoates, fibrins, cyclodextrins, proteins (e.g., soy protein), other polysaccharides (e.g., pectin), and/or polylactic acids.

A biopolymer used in a method of the present invention preferably has a moisture content of less than about 20% by weight. In one embodiment, the biopolymer has a moisture content of less than about 20%, less than about 15%, less than about 10%, or less than about 5% by weight. In another embodiment, the biopolymer has a moisture content in a range of about 5% to about 20% by weight or about 10% to about 15% by weight. In yet another embodiment, a method of the present invention utilizes a biopolymer (e.g., starch) having a moisture content of less than about 20% by weight. In one embodiment, the biopolymer is in powder form.

A biopolymer used in a method of the present invention preferably has a molecular weight of at least about 10,000 Daltons. In one embodiment, the biopolymer has a molecular weight of at least about 10,000; at least about 20,000; at least about 30,000; at least about 40,000, at least about 50,000; at least about 60,000; at least about 70,000; at least about 80,000; at least about 90,000; or at least about 100,000 Daltons. In a preferred embodiment, the biopolymer has a molecular weight of at least about 50,000 Daltons. In another embodiment, the biopolymer has a molecular weight of about 100,000 Daltons to about 4,000,000 Daltons, about 500,000 Daltons to about 3,000,000 Daltons, or about 1,000,000 Daltons to about 2,000,000 Daltons. In yet another embodiment, when only one biopolymer is used to prepare the modified biopolymer, the biopolymer has a molecular weight of at least 50,000 Daltons. In still another embodiment, when two or more different biopolymers are used to prepare the modified biopolymer, at least one of the two or more different biopolymers has a molecular weight of at least 10,000 Daltons (e.g., at least 20,000; at least 30,000; at least 40,000, at least 50,000 Daltons). In one embodiment, the modified biopolymer is prepared using a biopolymer having a molecular weight of at least 50,000 Daltons optionally with a second different biopolymer having a molecular weight of at least 10,000 Daltons. In another embodiment, the biopolymer is polydisperse.

The present invention relates to the use of crosslinked, modified biopolymers as superabsorbent materials or superabsorbent polymers. The effectiveness of superabsorbent polymers is typically measured using Free Swell Capacity (FSC), Centrifuge Retention Capacity (CRC), and/or Absorbance Under Load (AUL). FSC refers to the superabsorbent polymer's ability to swell, whereas CRC refers to the superabsorbent polymer's ability to retain absorbed liquid under force following swelling and AUL refers to the superabsorbent polymer's ability to swell under pressure during swelling; AUL is generally directly related to "gel strength". The AUL is critical to success in hygiene product constructions. When absorbent particles have poor gel strength, these particles also have poor permeability and the outer particles will swell too quickly, preventing fluid uptake of the innermost particles. This inhibits the absorbent from swelling to its full potential and is known as gel blocking. Notably, the CRC and the AUL are generally inversely correlated, (i.e., a modified biopolymer with a higher CRC will typically have a lower AUL than a modified biopolymer with a lower CRC).

In a preferred embodiment, the modified biopolymer (manufactured from industrial grade corn starch) has a Centrifuge Retention Capacity (CRC) of at least 15 g/g in a saline solution according to INDA/EDANA Standard NWSP 241.0.R2 (15) entitled "Polyacrylate Superabsorbent Powders—Determination of the Fluid Retention Capacity in Saline Solution by Gravimetric Measurement Following Centrifugation." In another embodiment, the modified biopolymer has a CRC of at least 16 g/g or at least 19 g/g in a saline solution according to this standard. Alternatively, the modified biopolymer has a FSC of between about 18 and about 32 g/g and a CRC of between about 8 and about 19 g/g in a saline solution. In another embodiment, the modified biopolymer has a FSC of at least 25 g/g and a CRC of at least 17 g/g in a saline solution. In yet another alternative, the modified biopolymer has a FSC between 28 g/g and 45 g/g and a CRC between 17 g/g/and 30 g/g in a saline solution. In another embodiment, the modified biopolymer has a FSC of between about 18 and about 24 g/g and a CRC of between about 13 and about 16 g/g in defibrinated sheep's blood. In yet another embodiment, the modified biopolymer has a FSC of between about 21 and about 26 g/g and a CRC of between about 15 and about 19 g/g in FDA menses simulant. In other alternatives, the modified biopolymer has a FSC of between 18 g/g and 30 g/g and a CRC of between 13 g/g and 20 g/g in defibrinated sheep's blood and a FSC of between 21 g/g and 35 g/g and a CRC of between 15 g/g and 25 g/g in FDA menses simulant.

The present invention is advantageously utilized in two absorbent formulations with distinct applications, namely a first type of formulations which includes internal crosslinking (referred to herein as "modified biopolymer 1") and a second type of formulations which includes both internal crosslinking and surface crosslinking (referred to herein as "modified biopolymer 2"). Generally, modified biopolymer 1 has higher FSC and CRC values than modified biopolymer 2, and is consequently used in applications such as rheology modifiers. Modified biopolymer 2 generally has higher AUL values, and is consequently utilized in hygiene applications such as baby diapers, adult incontinence products, and feminine hygiene products. In one embodiment, the modified biopolymer 1 formulation includes a FSC of about 40 g/g, a CRC of about 35 g/g, and an AUL of about 5 g/g in a saline solution.

While synthetic superabsorbent polymers such as polyacrylate typically have a FSC of about 40 g/g, a CRC of about 35 g/g, and an AUL at 0.7 psi of about 15 g/g in 0.9% saline, the hygiene formulation of the present invention provides a biodegradable superabsorbent polymer with a CRC preferably between about 20 g/g and about 30 g/g and an AUL preferably between about 10 g/g to about 15 g/g in a saline solution. In another embodiment, the modified biopolymer preferably has a FSC of at least 25 g/g in a saline solution. In yet another embodiment, the present invention provides a biodegradable superabsorbent polymer with a CRC of at least about 18 g/g and an AUL at 0.7 psi of at least about 8 g/g in a saline solution. FSC, CRC, and AUL values within these ranges are provided in the examples below for specific formulations of modified biopolymer 1 and modified biopolymer 2.

The modified biopolymer 1 and modified biopolymer 2 formulations preferably utilize the same starch-based biopolymer. Notably, modified biopolymer 1 formulations of the present invention include bulk crosslinking (also referred to as "interior crosslinking") and do not include significant amounts of surface crosslinking. Bulk crosslinking involves crosslinkers forming covalent bonds between polymers and are assumed to be evenly distributed through the material. In contrast, modified biopolymer 2 formulations include both bulk crosslinking and surface crosslinking. As used herein, the term "surface crosslinking" denotes chemical and/or physical interactions where polymers are no longer freely soluble. Modified biopolymer 2 formulations generally have increased gel strength, but generally decreased retention compared to modified biopolymer 1 material.

Advantageously, the modified biopolymers of the present invention are superabsorbent polymers and do not require addition of synthetics or integration with synthetics such as polyacrylate to perform as a superabsorbent polymer. Accordingly, the modified biopolymers of the present invention do not include acrylic-based polymers (polyacrylate, acrylamide, etc.) in one embodiment. In other words, the modified biopolymers of the present invention are not graft polymers according to one embodiment of the present invention.

Alternatively, the present invention includes percentages of synthetic polymers such as polyacrylate blended with the modified biopolymers of the present invention. By way of example and not limitation, synthetic polymers such as polyacrylate are blended with modified biopolymer 2 of the present invention. Specifically, one blend includes 25% synthetic polymer and 75% modified biopolymer 2 in one embodiment. In another embodiment, a blend includes 50% synthetic polymer and 50% modified biopolymer 2. In other embodiments, ranges of synthetic superabsorbent polymers included in blends with modified biopolymer 2 are from about 5% to about 10%, about 10% to about 15%, or about 15% to about 20% synthetic superabsorbent polymer. In one embodiment, the blend includes between approximately 20% and approximately 30% modified biopolymer and between approximately 70% and approximately 80% synthetic polymer. Alternatively, the blend includes between approximately 30% and approximately 60% modified biopolymer and between approximately 40% and approximately 70% synthetic polymer. In yet another alternative, any blend percentage of modified biopolymer and synthetic polymer is utilized. Examples of synthetic polymers used in blending include, but are not limited to, sodium polyacrylate, potassium polyacrylate, alkyl polyacrylate, any other acrylate-based superabsorbent polymers, acrylamides, and polyacrylamides. In other embodiments, the modified biopolymer is blended with non-synthetic SAPs, such as polysaccharide-based SAPs, including cellulose or starch-based SAPs, glutamic acid-based polymers such as polyglutamic acid and other polymers created by fermentation. As used in the present application, "blending" refers to physical blending (i.e., physically mixing two or more polymers) or chemical blending through reaction or compounding.

In a preferred embodiment, the biopolymer is a starch. Exemplary starches include, but are not limited to, corn starch, potato starch, tapioca starch, and pea starch. Other starches utilized in the present invention include wheat starch, cassava starch, rice starch, sorghum starch, and/or barley starch. In one embodiment, the starch has an amylopectin content of about 70% w/w or more and an amylose content of about 30% w/w or less. In another embodiment, the starch has an amylopectin content of at least 70%, at least 75%, at least 80%, no greater than 80%, or no greater than about 85% w/w and an amylose content of less than 30%, less than 25%, less than 20%, no less than 20%, or no less than about 15% w/w. In yet another embodiment, the starch has an amylopectin content of less than 90% w/w.

In a further preferred embodiment, the biopolymer includes industrial grade corn starch manufactured from *Zea mays* indentata (commonly referred to as "dent" corn or "field" corn). The corn starch of the present invention includes an amylose content of approximately 30% w/w and an amylopectin content of approximately 70% w/w, and more specifically an amylose content of about 27% w/w and an amylopectin content of about 73% w/w. However, the content of the corn starch is operable to vary from between about 70% to about 75% amylopectin w/w and between about 25% to about 30% amylose w/w. Notably, the corn starch utilized in the present invention does not have an amylopectin content of 90% w/w or over 90% w/w. Waxy starches, such as waxy corn starch, typically have an amylopectin content of 100% w/w, approximately 100% w/w, or at least 90% w/w, such as the starches described in U.S. Pat. No. 8,710,212. Notably, the waxy starches described in U.S. Pat. No. 8,710,212 are much more expensive than the starches utilized in the present invention and have higher amylopectin content (w/w) than the starches utilized in the present invention. The higher amylopectin content of these waxy starches (at least 90% w/w) accordingly provides higher molecular weight molecules, which traditionally provide better performance (free swell capacity, centrifuge retention capacity, etc.) compared to non-waxy or regular industrial grade corn starches. The FSC of the absorbent material in the '212 patent is at least 13 g/g and the CRC is at least 10 g/g in a saline solution. However, the modified biopolymers of the present invention advantageously provide a biocompostable superabsorbent polymer with at least 75% biobased carbon content, and more preferably between at least 80% biobased carbon content or at least 85% biobased carbon content, with a FSC of at least 30 g/g, a CRC of at least 15 g/g, and an AUL at 0.7 psi of at least 11 g/g in a saline solution. In another embodiment, the biocompostable superabsorbent polymer has approximately 100% or 100% biobased carbon content.

Due to the cost prohibitive nature of waxy corn starch for use in hygiene products, the present invention preferably does not utilize waxy corn starch or any starch with an amylopectin content of greater than 90% for the starch-based modified biopolymer of the present invention. Alternatively, the present invention utilizes a mix of industrial or "dent" corn starch and waxy corn starch, with the amylopectin content of the mix of starches being less than 90%.

In another preferred embodiment, the biopolymer includes potato starch, which includes an amylopectin content of approximately 80% w/w and an amylose content of approximately 20% w/w. However, the content of the potato starch or any other botanical-based starch is operable to vary from between about 15% to about 20% amylose w/w and between about 80% to about 85% amylopectin w/w. In another embodiment, the amylose content of tapioca starch is between about 15% to about 18%, and correspondingly the amylopectin content of tapioca starch is between about 82% to about 85%.

In one embodiment, the starch is dissolvable in water (e.g., pre-gelatinized starch). In another embodiment, the starch is steam exploded to form a pre-gelatinized starch. In yet another embodiment, the starch has a reduced degree of crystallinity compared to a native starch.

In another preferred embodiment, the biopolymer is a chitosan. The chitosan preferably has a degree of deacetylation of about 50% to about 100%. In one embodiment, the chitosan has a degree of deacetylation of at least 50%, at least 55%, at least 60%, at least 65%, at least 70%, at least 75%, at least 80%, at least 85%, at least 90%, at least 95%, or at least 100%. In another embodiment, the chitosan has a degree of deacetylation in a range of about 70% to about 100% or at least 80%. In yet another embodiment, the chitosan has a molecular weight of at least 80,000 Daltons.

In one embodiment, the biopolymer is charge-modified according to a method described herein (e.g., by reacting the biopolymer with at least one charge-modifying agent in a homogeneous reaction blend). In one embodiment, the biopolymer naturally carries a charge (i.e., the biopolymer is natively charged in that the charge is present on the biopolymer not through a method of the present invention). In another embodiment, a method of the present invention changes the charge present on a biopolymer (e.g., type and/or amount of charge). In still another embodiment, a charge-modified biopolymer is soluble (e.g., partially or fully soluble) in a polar solvent (e.g., water and/or a polar organic solvent at room temperature and/or a nonpolar solvent at room temperature. In yet another embodiment, the charge-modified biopolymer is at least 70% soluble in a polar and/or a nonpolar solvent at room temperature. In one embodiment, solubility is used as an indication and/or a characteristic of a degree of charge modification.

"Charge-modifying agent" as used herein refers to a molecule or compound including a first moiety that reacts with an amine and/or hydroxyl group of the biopolymer and a second moiety that is positively charged or negatively charged under suitable conditions (e.g., at a certain pH). "Moiety" as used herein, refers to a portion of a molecule or compound having a particular functional or structural feature. For example, a moiety is a functional group or a reactive portion of a compound. As those of skill in the art recognize, a strong acidic moiety (e.g., —$SO_3H$) or a weak acidic moiety (e.g., —COOH) form a negatively charged moiety and a strong basic moiety (e.g., —$NH_3OH$) or a weak basic moiety (—$NH_2$) form a positively charged moiety.

In one embodiment, the at least one charge-modifying agent includes at least one moiety that is a positively charged group, such as, but not limited to, a primary amine, secondary amine, tertiary amine, quaternary ammonium, sulfonium, and/or phosphonium group. Exemplary charge-modifying agents that have a positively charged moiety include, but are not limited to, ethylene imine, N-(2-hydroxyethyl) ethylene imine, cyanamide, beta-morpholinoethyl chloride, S-diethyl amino 1,2-epoxypropane dimethyl aminoethyl methacrylate, epoxy 3-methyl ammonium, N-(2,3-epoxypropyl) trimethyl ammonium chloride, (4-chlorobutene-2) trimethyl ammonium chloride, 2-chloroethyl methyl ethyl sulfonium iodide, and/or Z-chloroethyl tributylphosphonium chloride. In another embodiment, the charge-modifying agent is a tertiary amino alkyl group, a hydroxyalkyl group, a quaternary ammonium alkyl group, or a hydroxyalkyl group.

In one embodiment, a positively charged moiety is introduced into and/or onto a biopolymer by reacting the biopolymer and the charge-modifying agent in a homogeneous reaction blend. This reaction optionally occurs in the presence of a catalyst. In another embodiment, this reaction is a dry melt process and/or is an etherification or esterification reaction.

Additionally, or alternatively, the at least one charge-modifying agent includes at least one moiety that has a negatively charged group, such as, but not limited to, a carboxyl, a sulfonate, a sulfate, and/or a phosphate group (e.g., sodium tripolyphosphate, phosphate esters, etc.). Exemplary charge-modifying agents that have a negatively charged moiety include, but are not limited to, acids (e.g., citric acid, glacial acetic acid, ethylenediaminetetraacetic acid (EDTA), and/or diethylene triamine pentaacetic acid (DTPA)); mono-halogen substituted carboxylic acids (e.g., monochloroacetic acid); acetates (e.g., sodium monochloroacetate); anhydrides (e.g., succinic anhydride, maleic anhydride, citraconic anhydride, and/or octenyl succinicanhydride); alkyl esters of acrylic acid, crotonic acid or itaconic acid (e.g., methyl and ethyl esters of acrylic acid, crotonic acid, or itaconic acid); acrylonitrile and its derivatives; sodium periodate; sulfones; and/or sulfonic acids (e.g., halo alkane sulfonic acids, chlorooxypropane sulfonic acid, epoxypropane sulfonic acid, chlorooxypropane sulfonic acid, epoxypropane sulfonic acid, ethene sulfonic acid, and/or salts thereof).

Figure 8:
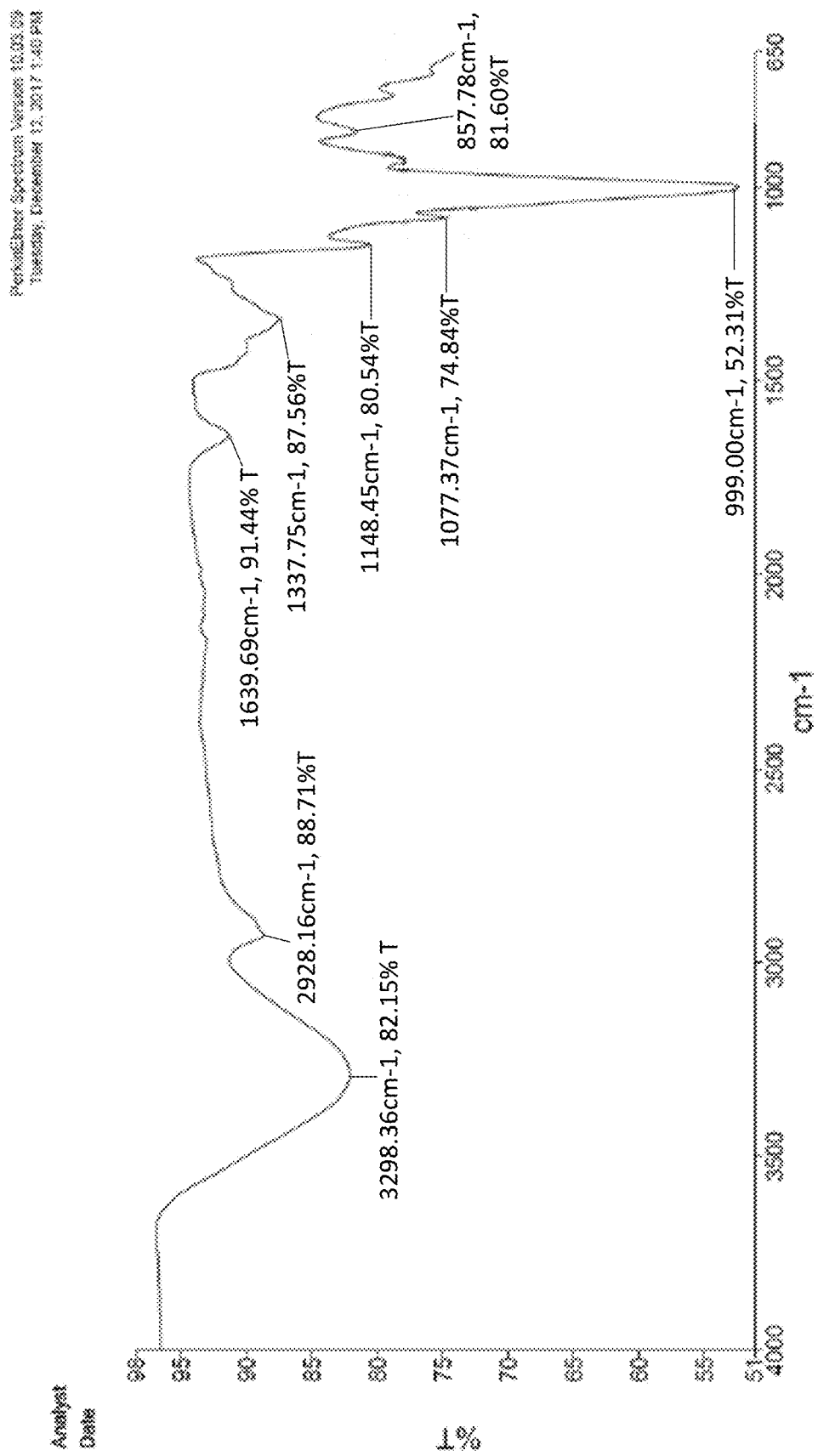
FIG. 8 illustrates FTIR spectrum for unmodified industrial grade corn starch.
Figure 9:
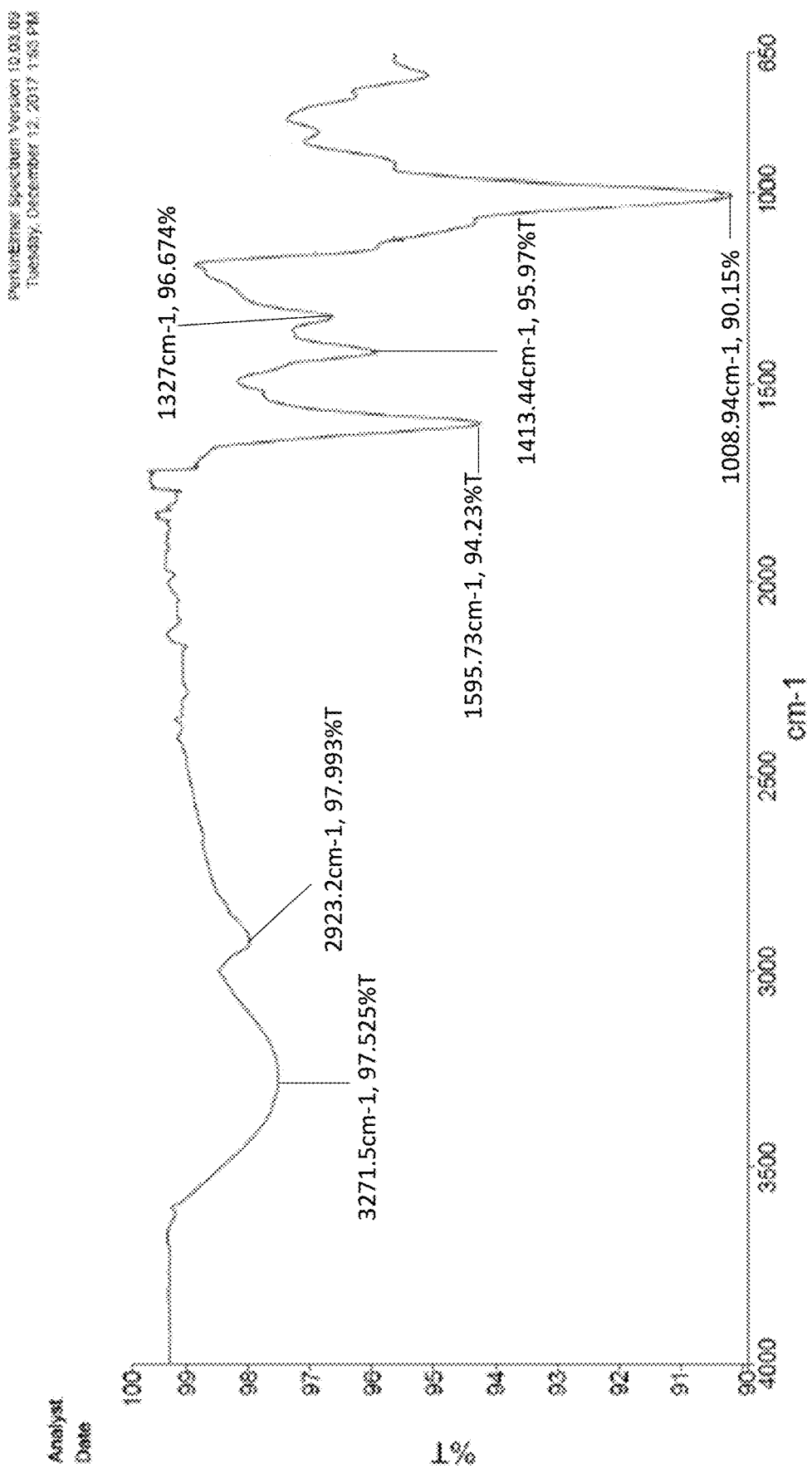
FIG. 9 illustrates FTIR spectrum for charge-modified starch according to one embodiment of the present invention.

FIG. 8 illustrates a FTIR spectrum for unmodified industrial grade corn starch. FIG. 9 illustrates FTIR spectrum for carboxymethyl starch according to one embodiment of the present invention, showing the peak at approximately 1596 cm$^{-1}$ from the carbonyl bond in the carboxymethyl substituent attached to the starch backbone. Thus, the present invention provides a carboxymethyl corn starch-based modified biopolymer according to one embodiment of the present invention.

In one embodiment, a negatively charged moiety is introduced into the biopolymer by reacting the biopolymer and the at least one charge-modifying agent in a homogeneous reaction blend in the presence of an alkaline catalyst. In one example, the charge-modifying agent is acrylonitrile and the reaction of the biopolymer and the acrylonitrile in the presence of an alkaline catalyst is followed by hydrolysis of the cyanoethyl groups. In another example, the charge-modifying agent is sodium periodate, and the reaction with the biopolymer is followed by a treatment to transform the carbonyl groups into carboxyl groups (e.g., by treating with sodium chlorite, sodium bisulfite, and/or potassium bisulfite). In yet another embodiment, both carboxyl and sulfonate groups are introduced into a biopolymer by reacting the biopolymer with an anhydride of an unsaturated acid (e.g., maleic acid) and a bisulfite. The bisulfite is reacted with the unsaturated bond of the polysaccharide half ester.

In one embodiment, one or more of the at least one charge-modifying agent reacts with an amine and/or hydroxyl group of the biopolymer to provide a charge-modified biopolymer. In one embodiment, the charge-modified biopolymer is cationic (i.e., has a net positive charge) or is anionic (i.e., has a net negative charge). In another embodiment, the charge-modified biopolymer contains both positively and negatively charged moieties.

In one embodiment, the biopolymer is crosslinked by reacting at least one crosslinking agent with the biopolymer and optionally with at least one different biopolymer that is optionally charge-modified. In another embodiment, the at least one crosslinking agent is reacted with at least one charge-modified biopolymer. "Crosslinking agent" as used herein refers to a compound that links two or more biopolymer chains and/or portions of the biopolymer together, the biopolymer optionally being charge-modified. In one embodiment, the linkage is achieved via a covalent bond or an ionic bond. In another embodiment, the linkage is through a moiety or group of the biopolymer or different biopolymers.

Crosslinking agents include, but are not limited to an acid including an organic acid or an inorganic acid. Examples of acids include dicarboxylic acid, tricarboxylic acid including citric acid, oxalic acid, malonic acid, succinic acid, glutaric acid, adipic acid, pimelic acid, fumaric acid, maleic acid, malic acid, tartaric acid, 2-acrylamido-2-methyl-1-propane-sulfonic acid), a sulfonic acid derivative (e.g., sodium 4-vinylbenzenesulfonate, 3-sulfopropyl methacrylate potassium salt, [2-(methacryloyloxy)ethyl]dimethyl-(3-sulfopropyl) ammonium hydroxide salt, [3-(methacryloylamino)propyl]dimethyl(3-sulfopropyl)ammonium hydroxide salt, hydrochloric acid and aluminum chloride. Other crosslinking agents include a sodium phosphate (e.g., sodium trimetaphosphate, sodium tripolyphosphate), a borate (e.g., sodium borate, sodium tetraborate, disodium tetraborate), an ionic crosslinker (e.g., calcium chloride, calcium hydroxide, etc.), a glycidyl ether (e.g., allyl glycidyl ether), an ammonium salt (e.g., glycidyltrimethylammonium chloride, (3-chloro-2-hydroxypropyl)trimethylammonium chloride, [2-(Acryloyloxy)ethyl]trimethylammonium chloride, (3-acrylamidopropyl)trimethylammonium chloride, [3-(methacryloylamino)propyl]trimethylammonium chloride, [2-(methacryloyloxy)ethyl]trimethylammonium chloride, diallyldimethylammonium chloride), a (meth)acrylic acid (e.g., acrylic acid, methacrylic acid), a (meth)acrylate (e.g., glycidyl methacrylate, glycidyl acrylate), a (meth)acrylate derivate (e.g., N-(3-aminopropyl)methacrylamide hydrochloride, 2-aminoethyl methacrylate hydrochloride), an ester (e.g., ethylene carbonate), a polyol (e.g., propane diol), an oxazolidinone (e.g., 2-hydroxyethyl-2-oxazolidinone), a metal crosslinker including a salt of a metal cation plus an anion, with the anion being organic or inorganic with examples of metal crosslinkers including metal lactates (e.g., aluminum lactate), zinc chloride, magnesium acetate, and magnesium acetate tetrahydrate and/or an anhydride (e.g., succinic anhydride, maleic anhydride). Crosslinkers that are not preferred include iron lactate including 0.5%, 1.5%, or 3% w/w iron lactate individually or in combination with 0.5% citric acid or 2-oxazlidinone including 0.1% or 0.4% w/w 2-oxazalidinone. Accordingly, the present invention preferably does not utilize these individual crosslinkers or these crosslinkers in combination with citric acid in one embodiment.

In one embodiment, the at least one charge-modifying agent dehydrates to yield an anhydride when heated inside an extruder. The free hydroxyl groups from a biopolymer (e.g., starch) present in the reaction mixture react with the anhydride to form starch citrate. In another embodiment, additional dehydration of the biopolymer and/or the charge-modified biopolymer allows for crosslinking of the biopolymer and/or the charge-modified biopolymer to occur. In yet another embodiment, crosslinking of the biopolymer and/or the charge-modified biopolymer is achieved due to the heat inside the extruder and/or during a post treatment process (e.g., a thermal post-treatment process). In still another embodiment, the charge-modified biopolymer is prepared using a ring-opening polymerization of anhydrous acids.

In one embodiment, the modified biopolymer includes a plurality of pores or void spaces formed therein. In another embodiment, the pores or void spaces have an average diameter of about 0.1 micron to about 500 microns (e.g., about 10 microns to about 500 microns, about 50 microns to about 500 microns, about 100 microns to about 400 microns, or about 250 microns to about 500 microns). In yet another embodiment, the pores or void spaces have an average diameter of about 0.1 micron, about 1 micron, about 10 microns, about 25 microns, about 50 microns, about 100 microns, about 150 microns, about 200 microns, about 250 microns, about 300 microns, about 350 microns, about 400 microns, about 450 microns, or about 500 microns.

In one embodiment, the modified biopolymer has a net positive charge (i.e., is cationic) or a net negative charge (i.e., is anionic). In another embodiment, the modified biopolymer is a polyampholyte. In yet another embodiment, the modified biopolymer is a polyelectrolyte that is hydrophilic (e.g., due to the number of ionizable groups present on the modified biopolymer). In a preferred embodiment, the modified biopolymer is a superabsorbent. In one embodiment, the superabsorbent absorbs a fluid in an amount of at least 15 times (e.g., 20×, 30×, 40×, 50×, 100×, etc.) relative to its weight. In another embodiment, the superabsorbent absorbs a saline solution in an amount of at least 20 times (e.g., 25×, 30×, etc.) relative to its weight at room temperature and/or water in an amount of at least 35 times or more (e.g., 40×, 45×, etc.) relative to its weight at room temperature. In yet another embodiment, the corn starch biopolymer superabsorbent of the present invention has a swelling capacity with a minimum of 13 g/g, and an exemplary swelling capacity of at least 23 g/g in defibrinated sheep's blood according to a modified FSC ran with defibrinated sheep's blood, compared to traditional synthetic swelling capacity with a minimum of 5 g/g and a maximum of 22 g/g.

The modified biopolymer is preferably a biosorbent. A "biosorbent" as used herein refers to an absorbent (e.g., that is utilized in the removal of a fluid) and/or an adsorbent (e.g., that is utilized as an ion exchange material and/or metal chelating material). In a preferred embodiment, the biosorbent is a superabsorbent.

The modified biopolymer preferably has an absorbency under load (AUL) at 0.7 psi of at least 5 g/g in a saline solution. The AUL is tested according to INDA/EDANA Standard WSP 242.2.R3 entitled "Gravimetric Determination of Permeability Dependent Absorption Under Pressure", which is incorporated herein by reference in its entirety.

The modified biopolymer preferably has a charge density of about 3 meq/g or more (e.g., as determined by titration). In one embodiment, charge density is determined by titration as described in Example 1.1. In one embodiment, the modified biopolymer has a charge density of at least 3 meq/g, at least 3.5 meq/g, at least 4 meq/g, at least 4.5 meq/g, at least 5 meq/g, at least 5.5 meq/g, at least 6 meq/g, at least 6.5 meq/g, at least 7 meq/g, at least 7.5 meq/g, at least 8 meq/g, at least 8.5 meq/g, at least 9 meq/g, at least 9.5 meq/g, or at least 10 meq/g as determined by titration. In a preferred embodiment, the modified biopolymer has a charge density of at least about 5 meq/g as determined by titration.

In one embodiment, the modified biopolymer has the charge modification substantially uniformly distributed throughout the bulk of the modified biopolymer. Thus, the modified biopolymer has a substantially uniform charge density. In another embodiment, the uniformity of the charge density of a modified biopolymer is determined by evaluating the presence of insoluble materials after exposure of the modified biopolymer to a solvent (e.g., water). In yet another embodiment, observation of particles (such as, for example, 1-10 μm particles) indicates the lack of charge modification within the particles and/or modified biopolymer. In still another embodiment, charge density distribution on the modified biopolymer is determined and/or evaluated using one or more spectrographic analytical techniques such as, but not limited to, EDS, Electron Phenomenological Spectroscopy (EPS), and/or Time-of-Flight Secondary Ion Mass Spectrometry (TOF-SIMS) of the charged moiety's counter ion. In one embodiment, an uneven distribution of counter ions and/or the presence of particles (e.g., 1-10 μm particles) lacking the counter ion indicates non-uniformity and/or inhomogeneity in regard to the distribution of the charge on the modified biopolymer.

The modified biopolymer of the present invention preferably has an increased charge density and/or degree of crosslinking compared to a modified biopolymer (e.g., a crosslinked, charge-modified biopolymer) prepared using a conventional method. "Conventional method" as used herein in reference to a method for preparing a modified biopolymer refers to a method for preparing a modified biopolymer in which the biopolymer is a solid (e.g., a particulate) and a reaction of the biopolymer with at least one reactant in the method occurs at a solid interface of the biopolymer. In one embodiment, a conventional method is a method that does not involve a melt extrusion process, such as a reactive extrusion process. In another embodiment, a conventional method is a semi-dry process, a multi-phase process, a process having a liquid interface with a solid material, and/or a heterogeneous process. In still another embodiment, a conventional method is a heterogeneous wet chemistry method and/or a multi-phase process. Conventional methods utilized in the present invention typically form homogenous reaction blends once all reactants are added.

The modified biopolymer preferably has a charge density and/or degree of crosslinking that is increased by at least 5% or more compared to a modified biopolymer prepared using a conventional method. In one embodiment, the modified biopolymer has a charge density and/or degree of crosslinking that is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, or at least 200% to a modified biopolymer prepared using a conventional method.

In one embodiment, a degree or an amount of crosslinking present in the modified biopolymer provides mechanical rigidity to the modified biopolymer and/or correlates with a degree of mechanical rigidity in the modified biopolymer.

The modified biopolymer preferably has a degree of substitution of at least 0.01 (e.g., in a range of about 0.01 to about 0.3). In a preferred embodiment, the modified biopolymer has a degree of substitution of between about 0.3 to about 0.6, and more preferably between about 0.4 to about 0.6. In another embodiment, the degree of substitution is less than about 0.5. In other alternatives, the degree of substitution is about 0.6, about 0.5, and about 0.42. In yet another embodiment, the degree of substitution is measured by nitrogen content (e.g., for anionic modified biopolymers).

Figure 10:
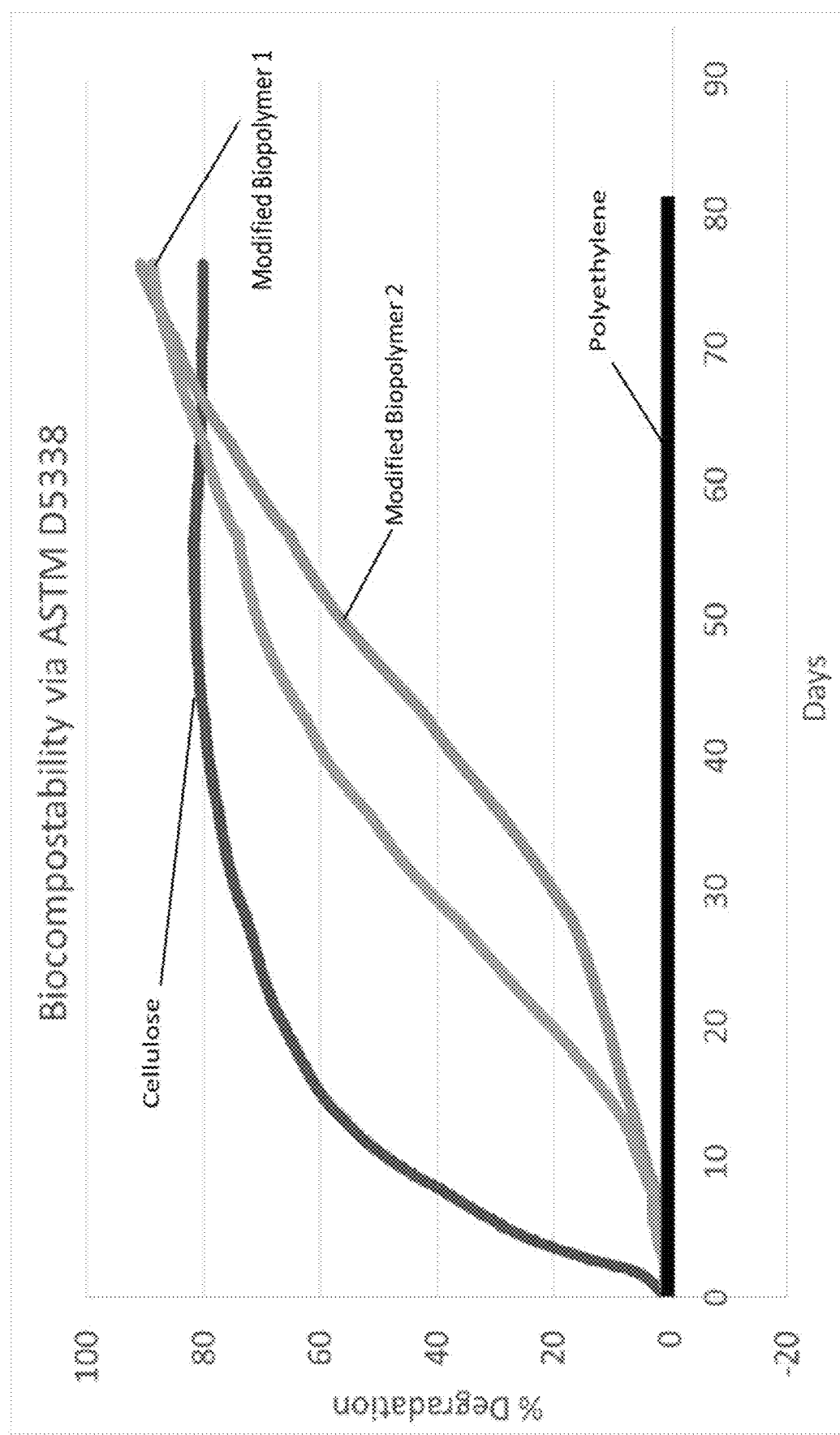
FIG. 10 is a chart illustrating the percent degradation of two modified corn starch-based biopolymers compared to analytical grade cellulose and polyethylene.

The modified biopolymer preferably is biocompostable and/or biodegradable. In one embodiment, the modified biopolymer degrades by at least 90% relative to a cellulose control in less than 180 days according to a modified ASTM D5338, where fewer samples were run on smaller, more precise equipment compared to traditional ASTM D5338. Specifically, at least the modified biopolymers described in Example 11 below are biocompostable according to ASTM D5338. ASTM D5338 is a standard biodegradation test that measures the aerobic biodegradation of plastic materials under controlled composting conditions; ASTM D5338 is a test method for meeting the biocompostability standard of the ASTM D6400 standard. In a preferred embodiment, the modified biopolymer degrades by at least 90% in less than 90 days relative to cellulose. The modified biopolymers of the present invention are biodegradable and/or biocompostable regardless of the starch utilized, wherein starches include but are not limited to, corn starch, potato starch, tapioca starch, and pea starch. FIG. 10 is a chart illustrating the percent degradation of two modified corn starch-based biopolymers having at least 80% biobased carbon content, an amylose content of approximately 30% w/w, and an amylopectin content of approximately 70% w/w compared to analytical grade cellulose with particles having diameters no greater than 20 microns and pellets of polyethylene. Notably, the Biorenewable Carbon Index (BCI) for the modified biopolymers estimated 84% to 85% biobased carbon content, and the ASTM D6866 Carbon 14 Test measured 85.9% biobased carbon content for these modified biopolymers. The ASTM D5338 testing was conducted at the University of Georgia's Center for Biodegradable Polymers and Additives, and the ASTM D6866 Carbon 14 Test was conducted at Beta Analytic in Florida. As illustrated in FIG. 10 both modified biopolymers of the present invention showed over 90% degradation in less than 90 days relative to a cellulose control (analytical grade cellulose), and are accordingly biocompostable according to ASTM D5338 guidelines. Notably, both modified biopolymers of the present invention degraded over 80% in 70 days, over 60% in 50 days, over 40% in 45 days, and over 20% in 30 days relative to a cellulose control. Both modified biopolymers of the present invention also degrade over 70% in 70 days, over 50% in in 50 days, over 35% in 45 days, and over 15% in 30 days relative to a cellulose control. In other words, both modified biopolymers exhibited over 40% degradation in 60 days and over 60% degradation in 90 days relative to a cellulose control. Both modified biopolymers degraded more than the cellulose control after approximately 70 days. The aforementioned degradation data applies to modified biopolymers with a particle size range of 150 microns to 350 microns. In another embodiment, another modified biopolymer of the present invention with a particle size range of 150 microns to 850 microns degrades over 40% in 35 days, over 45% in 85 days, and over 50% in 90 days. In another embodiment, ASTM D6400 (ASTM D6400-19, Standard Specification for Labeling of Plastics Designed to be Aerobically Composted in Municipal or Industrial Facilities, ASTM International, West Conshohocken, P A, 2019), ISO 14855 (ISO 14855-2:2018, Determination of the Ultimate Aerobic Biodegradability of Plastic Materials Under Controlled Composting Conditions—Method by Analysis of Evolved Carbon Dioxide—Part 2: Gravimetric Measurement of Carbon Dioxide Evolved in a Laboratory-Scale Test, International Organization for Standardization, Geneva, Switzerland, 2018), and/or ASTM D5338 (ASTM D5338-15, Standard Test Method for Determining Aerobic Biodegradation of Plastic Materials Under Controlled Composting Conditions, Incorporating Thermophilic Temperatures, ASTM International, West Conshohocken, Pa., 2015), each of which is incorporated herein by reference in its entirety, are used to determine biocompostability and/or biodegradability. The modified corn starch-based biopolymers are biocompostable according to ASTM D5338 guidelines. According to the Biorenewable Carbon Index (BCI), these modified biopolymers include between approximately 84% to approximately 85% biobased carbon content. The BCI method provides a quantitative estimate of the number of bioderived carbons in the final product as a percentage of total carbons in the final product. As an example, sodium polyacrylate (a synthetic SAP) has 0 bio-derived carbons out of three total carbons in each sodium acrylate monomer. In contrast, glucose has 6 bio-derived carbons out of the total 6 carbons in each glucose monomer. According to the ASTM D6866-18 Carbon 14 Test, the modified corn starch-based biopolymers include about 85.9% biobased carbon content, which meets the criteria for the four-star rating of the TUV Austria OK biobased certification (formerly known as the Vincotte Bioderived certification), with the four-star rating requiring that composition include greater than 80% biobased carbon content. The ASTM D6866 Carbon 14 Test was completed by the Beta Analytic Biobased and Biogenic Carbon Testing Laboratory ISO/IEC 17025:2005 (Testing accreditation PJLA #59423, Miami, Fla.).

In one embodiment, the modified biopolymer includes a plurality of pores and/or void spaces. The modified biopolymer of the present invention has an increased porosity and/or pore size compared to a modified biopolymer prepared using a conventional method. In one embodiment, the porosity is increased by increasing the number of pores or void spaces. The pores or void spaces are substantially the same size (e.g., varying in size or diameter by less than about 20%) in one embodiment. Alternatively, the pores or void spaces are different sizes. In one embodiment, the modified biopolymer has a porosity and/or pore size that is increased by at least about 5% or more compared to a modified biopolymer prepared using a conventional method. In some embodiments, the modified biopolymer has a porosity and/or pore size that is increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, or at least 200% compared to a modified biopolymer prepared using a conventional method.

In one embodiment, the modified biopolymer has a more uniform porosity and/or pore size compared to a modified biopolymer prepared using a conventional method. A more uniform porosity includes a more uniformly or evenly dispersed number of pores or void spaces throughout the modified biopolymer. In another embodiment, a more uniform pore size includes a more uniform diameter of the pores or void spaces throughout the modified biopolymer. In yet another embodiment, the porosity and/or pore size of the modified biopolymer of the present invention is more uniform compared to the porosity and/or pore size of a modified biopolymer prepared using a conventional method, and varies by less than about 20% (e.g., by less than 20%, less than 15%, less than 10%, less than 5%) as determined by comparing two or more defined areas of the modified biopolymer compared to two or more defined areas of the modified biopolymer prepared using a conventional method.

In one embodiment, the modified biopolymer sequesters, binds, absorbs, chelates, uptakes, adsorbs, and/or the like a fluid (e.g., water, hydrocarbons, oils, alcohols, aqueous solutions, non-aqueous solutions, ionic solutions such as salt solutions, biological fluids such as blood and/or urine, gases, waste water, and/or fracking fluids), a charged species (e.g., ions such as potassium ions ($K^+$), calcium ions ($Ca^{2+}$), sodium ions ($Na^+$), chloride ions ($Cl^-$), fluoride ions ($F^-$), phosphite ions ($PO_3^{3-}$), sulfate ions ($SO_4^{2-}$), sulfite ions ($SO_3^{2-}$), phosphate ions ($PO_4^{3-}$), polyatomic ions, and/or metal ions; charged peptides, polypeptides, nucleic acids, and/or oligonucleotides; and the like), and/or a metal (e.g., lead, mercury, cadmium, arsenic, copper, chromium, thallium, selenium, zinc, calcium, magnesium, silver, boron, and the like). In another embodiment, the modified biopolymer physically adsorbs a species present in the fluid (e.g., an ionic species and/or a metal). In yet another embodiment, the species is dissolved in the fluid. In still another embodiment, the modified biopolymer binds a fluid, charged species, and/or metal (e.g., via hydrogen bonding, covalent bonding, van der Waals/adsorptive binding, and/or ionic bonding).

In one embodiment, the modified biopolymer sequesters, binds, absorbs, chelates, uptakes, adsorbs, and/or the like an ion and/or a metal. In another embodiment, the metal is in an ionized form (e.g., in the form of a salt). As those skilled in the art recognize, a metal may exist in a number of ionized forms (e.g., monovalent, divalent, polyvalent, anionic, and/or cationic forms). Further exemplary ions and/or metals, in any ionized form, that the modified biopolymer sequesters, binds, absorbs, chelates, uptakes, adsorbs, and/or the like include, but are not limited to, sodium, potassium, lithium, ammonium, barium, strontium, manganese, silver, cesium, zinc, cadmium, selenium, calcium, magnesium, iron, radium, mercury, copper, lead, nickel, chromium, arsenic, gold, uranium, chloride, bromide, nitrate, iodide, carbonate, sulphate, and/or phosphate.

In one embodiment, the modified biopolymer sequesters, binds, absorbs, chelates, uptakes, adsorbs, and/or the like an organic compound. Exemplary organic compounds include, but are not limited to, toluene, xylenes, benzene, ethylbenzene, trimethylbenzene, acetone, and/or methanol.

The modified biopolymer of the present invention sequesters, binds, absorbs, chelates, uptakes, adsorbs, and/or the like an increased amount or concentration of a fluid, a charged species, and/or a metal compared to a modified biopolymer prepared using a conventional method. In a preferred embodiment, the modified biopolymer of the present invention sequesters, binds, absorbs, chelates, uptakes, adsorbs, and/or the like an increased amount or concentration of a fluid, charged species, and/or a metal by at least about 5% or more compared to a modified biopolymer prepared using a conventional method. In some embodiments, the modified biopolymer sequesters, binds, absorbs, chelates, uptakes, adsorbs, and/or the like an increased amount or concentration of a fluid, charged species, and/or a metal by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, or at least 200% compared to a modified biopolymer prepared using a conventional method.

As previously detailed, the modified biopolymer is preferably formed of a starch and/or a chitosan. In one embodiment, the starch and/or the chitosan is charged-modified and the starch and the chitosan are crosslinked with each other to form a crosslinked, charged-modified starch-chitosan biopolymer.

The modified biopolymer is preferably formed in a homogeneous reaction blend. A homogeneous reaction blend is a melted blend of all components or reactants in a single phase. In one embodiment, the homogeneous reaction blend is obtained using an extruder. In another embodiment, the homogeneous reaction blend is obtained using a reactive extrusion process in an extruder.

In one embodiment, the homogeneous reaction blend is in the form of a single liquid phase. In another embodiment, the homogeneous reaction blend provides a uniform distribution of the components or reactants as compared to a conventional method. In yet another embodiment, formation of the homogeneous reaction blend provides a chemical reaction that occurs more uniformly and/or completely as compared to a conventional method. In one embodiment, the biopolymer in the homogeneous reaction blend is a melted thermoplastic. In a preferred embodiment, the homogeneous reaction blend does not include ethanol. The homogeneous reaction blend preferably does not include ethanol in the extrusion mixture so that the extrusion mixture is purposefully substantially or completely gelatinized or gelatinous and is not in granular form. In another embodiment, the biopolymer reacts thermo-mechanically and/or chemically with one or more reagents to form a charge-modified biopolymer. In yet another embodiment, the charge-modified biopolymer is thermoplastic and/or a viscoelastic material. In still another embodiment, hydrogen bonding and/or crystalline domains initially present in the biopolymer are removed. Advantageously, this allows for all or substantially all portions of the biopolymer to be available for chemical reaction (e.g., via charge-modification and/or crosslinking).

A "reactive extrusion process" as used herein refers to a process in which a biopolymer is both chemically and physically modified. In one embodiment, the reactive extrusion process provides for a chemical modification of the biopolymer, such as, but not limited to, grafting onto the biopolymer, crosslinking of the biopolymer, functionalization of the biopolymer, and/or charge-modification of the biopolymer. In another embodiment, the reactive extrusion process provides for polymerization and/or branching of the biopolymer. In yet another embodiment, the polymerization and/or branching is with a different biopolymer to provide a co-polymer. An exemplary physical modification is changing the form of the biopolymer, such as, but not limited to, from a powder, particulate, and/or solid form to a molten or melted form.

In one embodiment, a biopolymer and at least one charge-modifying agent are reacted in a homogeneous reaction blend to form a charge-modified biopolymer. In another embodiment, the biopolymer and the at least one charge-modifying agent are combined, optionally with a plasticizer and/or catalyst, to form the homogeneous reaction blend. In yet another embodiment, at least two different biopolymers are reacted with at least one charge-modifying agent in a homogeneous reaction blend. Optionally, one or more of the at least two different biopolymers is charge-modified prior to the reacting step.

In one embodiment, the at least one charge-modifying agent is present in a homogeneous reaction blend in an amount of about 5% to about 200% or more by weight of at least one biopolymer present in the homogeneous reaction blend. In one embodiment, the at least one charge-modifying agent is present in a homogeneous reaction blend in an amount of at least about 75% by weight of at least one biopolymer present in the homogeneous reaction blend. In another embodiment, the at least one charge-modifying agent is present in a homogeneous reaction blend in an amount of at least about 75% by weight of a biopolymer and provides a modified biopolymer having a charge density of at least 1.5 meq/g (e.g., as determined by titration).

In one embodiment, a biopolymer and at least one crosslinking agent are reacted in a homogeneous reaction blend to form a crosslinked biopolymer. In another embodiment, the biopolymer and the at least one crosslinking agent are combined, optionally with a plasticizer and/or catalyst, to form the homogeneous reaction blend. In yet another embodiment, at least two different biopolymers are reacted with at least one crosslinking agent in the homogeneous reaction blend.

Alternatively, a biopolymer (e.g., starch), a polymer (e.g., polyacrylate), and at least one crosslinking agent are reacted in a homogenous reaction blend to form a graft copolymer (e.g., starch-acrylate copolymer). In one embodiment, the biopolymer is a charge-modified biopolymer. In another embodiment, cyclic ester co-polymers such as poly(caprolactone) are utilized to form graft copolymers. Cyclic ester co-polymers are described in U.S. Pat. No. 5,540,929, which is incorporated herein by reference in its entirety. Other co-polymers operable to be utilized in the present invention include polystyrenes, polybutadienes, or any other molecule including a terminal alkene operable to be grafted through a free radical mechanism.

In one embodiment, the homogeneous reaction blend is formed using at least two different biopolymers. In another embodiment, the homogeneous reaction blend is formed using a charge-modified biopolymer and at least one different biopolymer. In yet another embodiment, one or more of the at least one different biopolymer is charge-modified. When two biopolymers are present in the homogeneous reaction blend, a first biopolymer is present in the homogeneous reaction blend in an amount of about 10% to about 200% or more by weight of a second biopolymer present in the homogeneous reaction blend. In still another embodiment, the first biopolymer is present in the homogeneous reaction blend in an amount of about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, or more by weight of the second biopolymer present in the homogeneous reaction blend.

In one embodiment, the first biopolymer and the second biopolymer are present in the homogeneous reaction blend in a ratio in a range of 0.1:1 to 4:1 (first biopolymer: second biopolymer) (e.g., in a ratio in a range of 0:5:1 to 2:1 or 1:1 to 3:1). In another embodiment, the first biopolymer and the second biopolymer are present in the homogeneous reaction blend in a ratio of about 0.5:1, 1:1, or 1:0.5.

In one embodiment, a biopolymer and at least one charge-modifying agent are reacted in a homogeneous reaction blend to form a charge-modified biopolymer. The charge-modified biopolymer is then reacted with at least one crosslinking agent in the homogeneous reaction blend to form a crosslinked, charge-modified biopolymer. In another embodiment, at least two different biopolymers are reacted with at least one charge-modifying agent in the homogeneous reaction blend to form at least one charge-modified biopolymer. In yet another embodiment, the charge-modified biopolymer is crosslinked to one or more of the at least two different biopolymers in the homogeneous reaction blend. The one or more different biopolymers is optionally charge-modified prior to a combining, a reacting, and/or a crosslinking step. In still another embodiment, the biopolymer and the at least one charge-modifying agent are combined to form the homogeneous reaction blend.

In one embodiment, a crosslinked, charge-modified biopolymer is formed using a first biopolymer and a second biopolymer. In one embodiment, the first biopolymer and/or the second biopolymer is charge-modified prior to addition to a homogeneous reaction blend. In another embodiment, the first biopolymer and/or the second biopolymer is charge-modified in the homogeneous reaction blend. In yet another embodiment, charge modification of the first biopolymer and/or the second biopolymer and subsequent crosslinking occur in more than one homogeneous reaction blend. In one example, charge modification of the first biopolymer occurs in a first reaction blend to form a charge-modified first biopolymer, charge modification of the second biopolymer occurs in a second reaction blend to form a charge-modified second biopolymer, and crosslinking of the charge-modified first biopolymer and the charge-modified second biopolymer occurs in a third homogeneous reaction blend to form a crosslinked, charge-modified biopolymer.

In one embodiment, one or more steps (e.g., a combining, reaction, and/or crosslinking step) occur simultaneously and/or sequentially with another step. For example, in one embodiment, a reacting step to form a charge-modified biopolymer occurs simultaneously with a crosslinking step to form a crosslinked, charge-modified biopolymer. In another embodiment, a crosslinking step to form a crosslinked, charge-modified biopolymer occurs after a reacting step to form a charge-modified biopolymer. In yet another embodiment, a reacting step and a crosslinking step occur in different reaction zones of an extruder.

In one embodiment, the modified biopolymer is produced using a continuous process. In another embodiment, the reacting and/or crosslinking steps occur and/or are carried out in a continuous process. A continuous process is one that does not involve intermediate steps that stop a reaction in process. Exemplary intermediate steps include, but are not limited to, changing a buffer or providing a wash step before obtaining the product. In yet another embodiment, the continuous process is carried out or performed in an extruder optionally using a reactive extrusion process. For example, a continuous process includes a process in which all reactants are added to an extruder either at the same time or different times and the process occurs continuously (i.e., without stopping for intermediate steps) until the modified biopolymer is extruded. In still another embodiment, a continuous process also includes a step that is carried out or performed in an extruder, such as a reacting and/or a crosslinking step.

In one embodiment, the modified biopolymer is produced using a continuous process followed by a non-continuous process (e.g., post-treatment). In another embodiment, the modified biopolymer is produced using a continuous process, a non-continuous process (e.g., a batch process), and optionally a subsequent continuous process. In one example, a continuous process is used to prepare a charge-modified biopolymer (e.g., a charge-modified starch), and then the charge-modified biopolymer undergoes a post-treatment (e.g., optionally a batch process). In another example, the charge-modified biopolymer (e.g., a charge-modified starch) is then reacted with a second biopolymer (e.g., chitosan). In one embodiment, the second biopolymer is charge-modified.

In one example, a charge-modified first biopolymer and a charge-modified second biopolymer that is different than the charge-modified first biopolymer are combined, optionally with at least one plasticizer, at least one crosslinking agent, and/or at least one catalyst, to form a homogeneous reaction blend. The charge-modified first biopolymer and the charge-modified second biopolymer are crosslinked in the homogeneous reaction blend to form a crosslinked, charge-modified biopolymer.

In another example, a first biopolymer, a second biopolymer that is different than the first biopolymer, at least one charge-modifying agent, at least one plasticizer, and optionally at least one catalyst are combined to form a homogeneous reaction blend. The first biopolymer and the second biopolymer are reacted with the at least one charge-modifying agent to form a charge-modified first biopolymer and a charge-modified second biopolymer. The charge-modified first biopolymer and the charge-modified second biopolymer are crosslinked to form a crosslinked, charge-modified biopolymer.

In yet another example, a first biopolymer, a first charge-modifying agent, and optionally at least one catalyst are combined to form a homogeneous reaction blend including a charge-modified first biopolymer. A charge-modified second biopolymer and at least one plasticizer are added to the homogeneous reaction blend including the charge-modified first biopolymer. The charge-modified first biopolymer and the charge-modified second biopolymer are crosslinked to form a crosslinked, charge-modified biopolymer.

In still another example, a first biopolymer, a first charge-modifying agent, and optionally at least one catalyst are combined to form a charge-modified first biopolymer. A homogeneous reaction blend is formed including the charged-modified first biopolymer, a charged-modified second biopolymer, and at least one plasticizer. The charge-modified first biopolymer and the charged-modified second biopolymer are crosslinked to form a crosslinked, charge-modified biopolymer.

In yet another example, a homogeneous reaction blend is formed by combining a first biopolymer, a second biopolymer that is optionally charged-modified, and at least one charge-modifying agent. The first biopolymer and the at least one charge-modifying agent are reacted in the homogeneous reaction blend to form a charge-modified biopolymer. The charge-modified biopolymer and the second biopolymer are crosslinked in the homogeneous reaction blend to form a crosslinked, charge-modified biopolymer.

In still another example, a first homogeneous reaction blend is formed by combining a first biopolymer and at least one charge-modifying agent. The first biopolymer and the at least one charge-modifying agent are reacted in the first homogeneous reaction blend to form a charge-modified biopolymer. The charge-modified first biopolymer is combined with a second biopolymer that is optionally charge-modified to form a second homogeneous reaction blend. The charge-modified first biopolymer and the second biopolymer are crosslinked in the second homogeneous reaction blend to form a crosslinked, charge-modified biopolymer.

In one embodiment, a reaction (e.g., charge-modification, crosslinking) occurs with faster kinetics than kinetics of the same reaction in a conventional method. In one embodiment, at least one reaction occurs at a speed increased compared to a speed of the same reaction in a conventional method. The modified biopolymer is preferably produced at an overall greater speed of reaction compared to a conventional method.

In one embodiment, at least one plasticizer is present in the homogeneous reaction blend with the biopolymer and the at least one charge-modifying agent. In another embodiment, the at least one plasticizer is combined with the biopolymer and the at least one charge-modifying agent to form a homogeneous reaction blend. In yet another embodiment, the at least one plasticizer is present in the homogeneous reaction blend in an amount of about 10% to about 400% or more by weight of at least one biopolymer present in the homogeneous reaction blend. In a preferred embodiment, the at least one plasticizer is present in the homogeneous reaction blend in an amount of at least about 30% or more by weight of at least one biopolymer (e.g., starch) present in the homogeneous reaction blend. In another preferred embodiment, the at least one plasticizer is present in the homogeneous reaction blend in an amount of at least about 100% or more by weight of at least one biopolymer (e.g., chitosan, hemicellulose, pectin, and/or soy protein) present in the homogeneous reaction blend.

In one embodiment, the at least one plasticizer is a low molecular weight non-volatile compound. Additional exemplary plasticizers include, but are not limited to, triphenyl phosphate, camphor oil, amyl acetate, allylurea, citrate esters, phthalic acid esters, citric acid, dioctyl phthalate, fatty acid esters, benzoates, tartrates, chlorinated hydrocarbons, esters of adipic acid, polyols (e.g., glycerol, ethylene glycol (EG), diethylene glycol (DEG), triethylene glycol (TEG), tetraethylene glycol, polyethylene glycol, propylene glycol (PG), sorbitol, mannitol, xylitol, fatty acids, and/or vegetable oils), lecithin, waxes, amino acids, surfactants, and/or water.

In one embodiment, the at least one plasticizer reduces the glass transition temperature ($T_g$). In another embodiment, the at least one plasticizer improves the flexibility, workability, distensibility, and/or processability of a biopolymer (e.g., by lowering the glass transition temperature ($T_g$)). In yet another embodiment, the biopolymer is not thermoplastic and the glass transition temperature ($T_g$) must be lowered by addition of the at least one plasticizer prior to extrusion.

The at least one plasticizer reduces the tension of deformation, hardness, density, viscosity, and/or electrostatic charge of the biopolymer and at the same time increases the biopolymer chain flexibility, resistance to fracture, and/or dielectric constant. Other properties of the biopolymer that may also be affected by the inclusion of the at least one plasticizer include, but not limited to, degree of crystallinity, optical clarity, electric conductivity, fire behavior and/or resistance to biological degradation. In one embodiment, the at least one plasticizer allows for the biopolymer to melt and/or become thermoplastic to provide a single phase. In another embodiment, the at least one plasticizer disrupts hydrogen bonds present in a crystalline structure of the biopolymer. In yet another embodiment, disrupting the hydrogen bonds leads to breaking of crystalline domains that prevent thermal processing. Advantageously, this allows for the melt processability of biopolymers that are not traditionally melt processable.

Figure 1B:
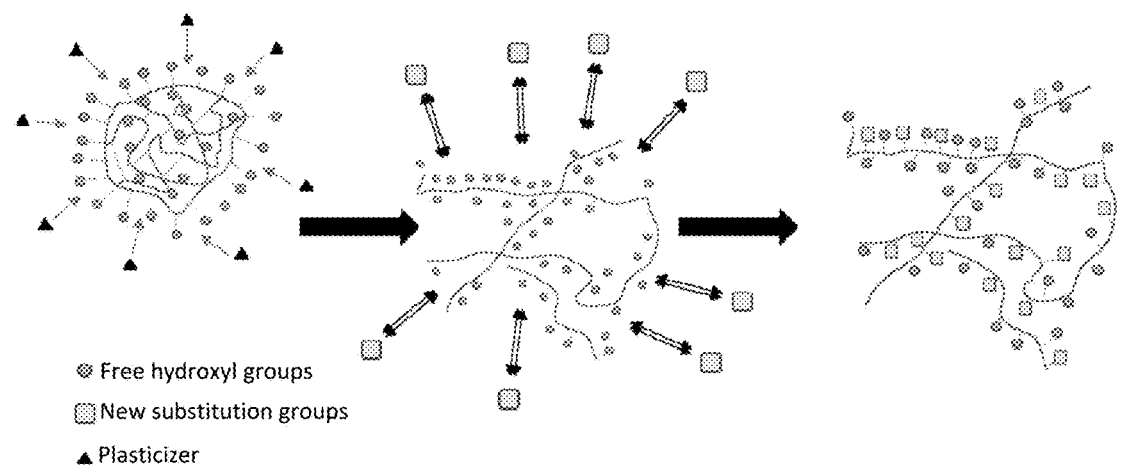
FIG. 1B is a schematic of a homogeneous phase reaction.

In one embodiment, the homogeneous reaction blend contains at least one plasticized biopolymer. The at least one plasticized biopolymer allows for greater access to moieties throughout the biopolymer. In contrast, in a heterogeneous phase reaction (e.g., in which modified biopolymers are synthesized by a coating process, in a diluted suspension, or with a concentrated gel solution) there is a limited amount of moieties (e.g., free hydroxyls) exposed to the reagent as the surface moieties are exposed to the reagent, and the interior moieties are not exposed. The reaction is thus carried out on the surface of the solid granule as shown in FIG. 1A (e.g., by direct conversion of either the semi-crystalline granules in aqueous suspension or as a dry process). FIG. 1B shows an exemplary schematic of a homogeneous phase reaction in which a biopolymer (e.g., starch) is plasticized using at least one plasticizer to obtain thermoplastic behavior. Under the action of thermo-mechanical energy, the starch granule melts. In one embodiment, the at least one plasticizer is adsorbed to the starch by heating the mixture. Destruction of the granular structure of the biopolymer occurs with the introduction of mechanical and heat energy. In the presence of at least one plasticizer, biopolymer granules are transferred to a continuous phase and moieties (e.g., hydroxyl free groups) are available to react with the reagent. In another embodiment, the homogeneous reaction blend aids in distributing a modification (e.g., a charge-modification) along a biopolymer chain and/or more uniformly throughout a biopolymer in contrast to a conventional method, such as, for example, one in which the modification is only achieved at the surface (e.g., at the surface of a solid biopolymer granule).

A catalyst is optionally present in the homogeneous reaction blend. In one embodiment, the catalyst and/or the plasticizer is combined with the biopolymer and the at least one charge-modifying agent to form the homogeneous reaction blend. In another embodiment, the catalyst is present in the homogeneous reaction blend in an amount of about 1% to about 100% or more by weight of at least one biopolymer present in the homogeneous reaction blend.

The catalyst accelerates the charge-modification and/or crosslinking reaction. In one embodiment, the catalyst adjusts the pH to enhance opening of chemical bonds. Exemplary catalysts include, but are not limited to, sodium hypophosphite, sodium bisulfate, sodium bisulfite, and/or caustics (e.g., sodium hydroxide, calcium hydroxide, etc.). In another embodiment, the charge-modification and/or crosslinking reaction is carried out at a pH in a range of about 9 to about 12, about 10 to about 12, about 2 to about 7, or about 2 to about 5.

In one embodiment, the catalyst is an initiator. In another embodiment, the catalyst is a photoinitiator. In yet another embodiment, the biopolymer (e.g., a charge-modified biopolymer) is reacted with at least one crosslinking agent in the presence of an initiator. Exemplary initiators include, but are not limited to, peroxides such as acyl peroxides (e.g., benzoyl peroxide), dialkyl or aralkyl peroxides (e.g., di-t-butyl peroxide, dicumyl peroxide, cumyl butyl peroxide, 1,1-di-t-butylperoxy-3,5,5-trimethylcyclohexane, 2,5-dimethyl-2,5-di-t-butylperoxy hexane, and bis(t-butylperoxyisopropyl)benzene), ketone peroxides (e.g., cyclohexanone peroxide and methylethylketone peroxide), ketones (e.g., 1-hydroxy-cyclohexyl-phenyl-ketone,), sodium methoxide, potassium persulfate, ceric ammonium, sodium hydroxide, and/or azo compounds (e.g., azobisisobutyronitrile).

In one embodiment, the initiator is used for a free radical reaction. In another embodiment, the initiator allows a terminal olefin on a monomer to generate a modified biopolymer. Exemplary monomers include, but are not limited to, styrene, vinyl acetate, acrylic acid, acrylonitrile, butadiene, methyl methacrylate, butyl acrylate, acrylamide, and/or diallyl dimethyl ammonium chloride.

In one embodiment, the initiator is present in the homogeneous reaction blend in an amount of about 1% to about 100% or more by weight of at least one biopolymer present in the homogeneous reaction blend.

In one embodiment, the modified biopolymer is subjected to a foaming process. Foaming induces porosity and/or void size of the modified biopolymer, such as by opening and/or increasing cell porosity. Additionally, foaming aids in increasing fluid, charged species, and/or metal sequestration, binding, absorption, chelation, uptake and/or the like. In another embodiment, the modified biopolymer has open, connected pores, which facilitates mass transfer within the modified biopolymer and access of ions in a fluid to the ionic binding sites of the modified biopolymer. In yet another embodiment, foaming the modified biopolymer modifies (e.g., increases or decreases) viscoelastic properties of the modified biopolymer. In still another embodiment, the amount or degree of modification of the viscoelastic properties varies with the amount of a fluid (e.g., water, carbon dioxide, nitrogen, etc.) absorbed in the modified biopolymer at the time of foaming.

A foaming agent is a chemical agent or a physical agent in one embodiment. Exemplary foaming agents, include, but not are limited to, supercritical nitrogen ($N_2$), calcium carbonate ($CaCO_3$), water (e.g., steam), and/or supercritical carbon dioxide ($CO_2$).

Optional additives used to prepare the modified biopolymer include, but are not limited to, dyes, pigments, organic fillers, inorganic fillers, softening agents (e.g., mineral oils and synthetic oils), flame retardants, crystallization accelerators, stabilizers (e.g., heat and light stabilizers), tie-agents, nucleating agents, other polymers (e.g., non-biopolymers), and/or the like.

Figure 6A:
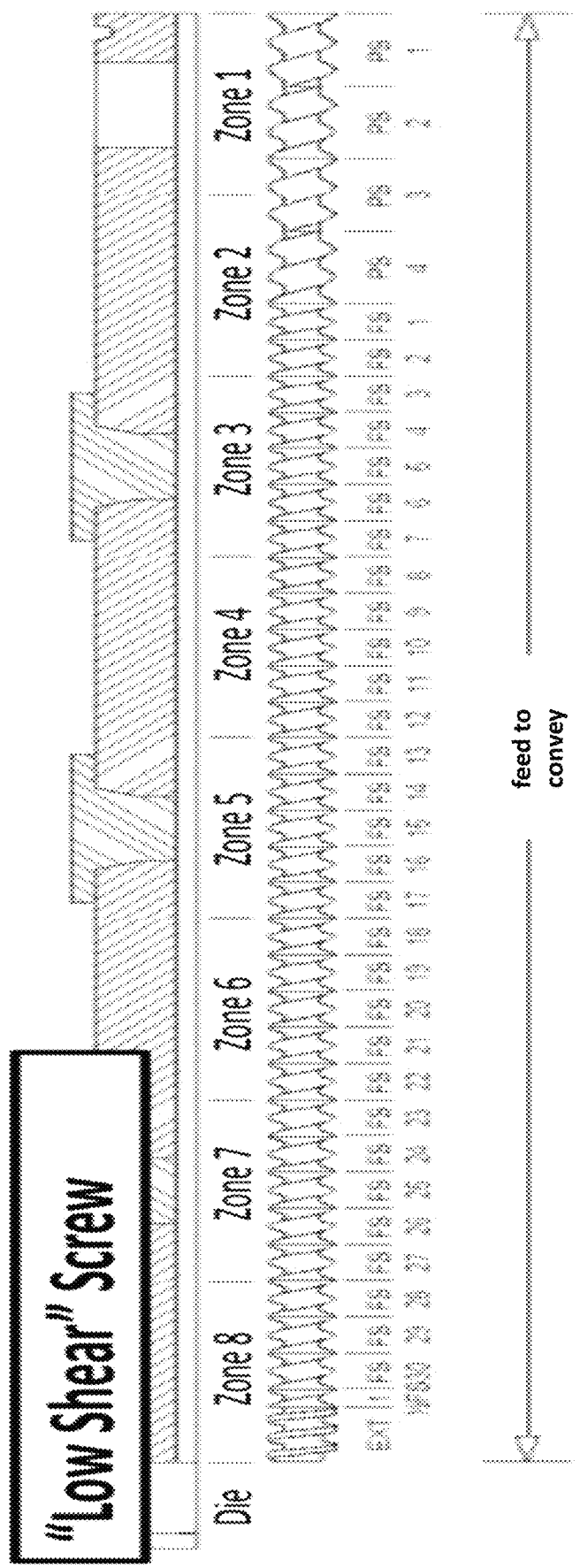
FIG. 6A illustrates exemplary "low shear" screw configurations according to one embodiment of the present invention.
Figure 6B:
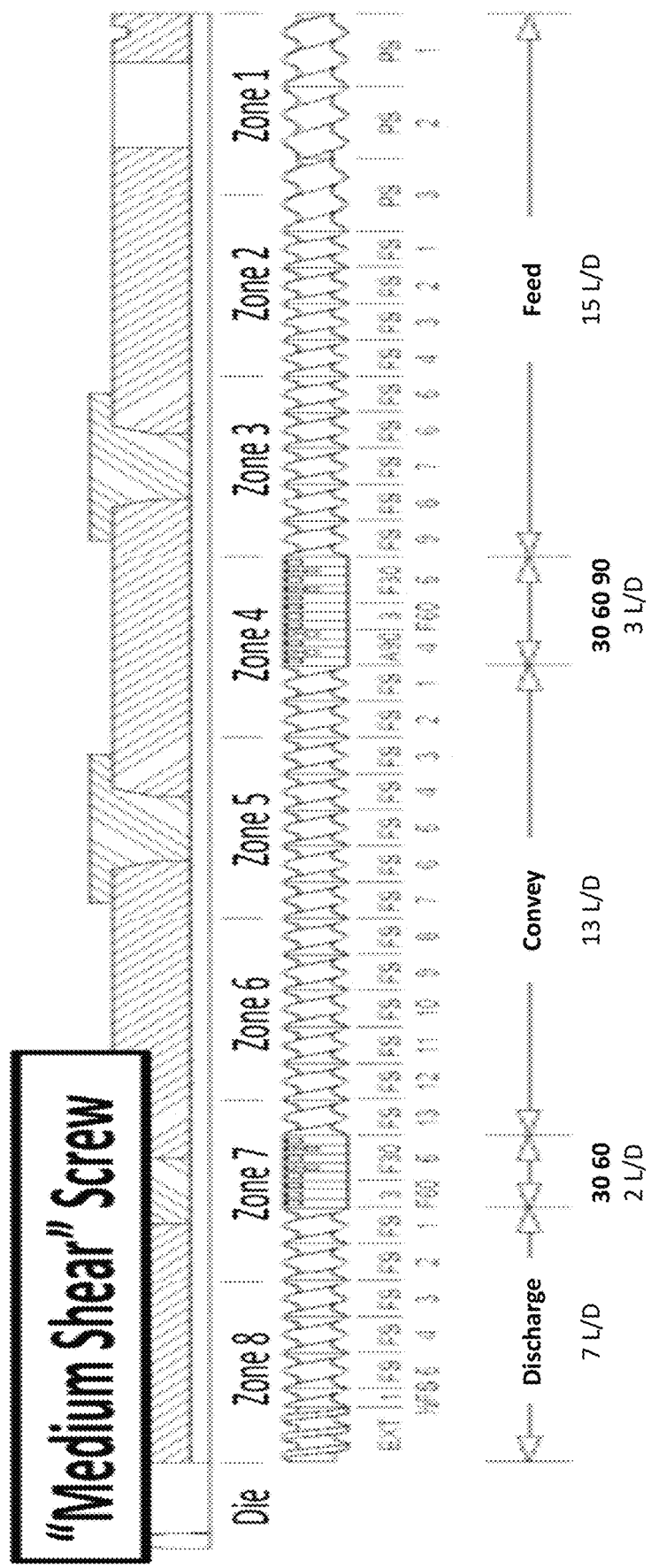
FIG. 6B illustrates exemplary "medium shear" screw configurations according to one embodiment of the present invention.
Figure 6C:
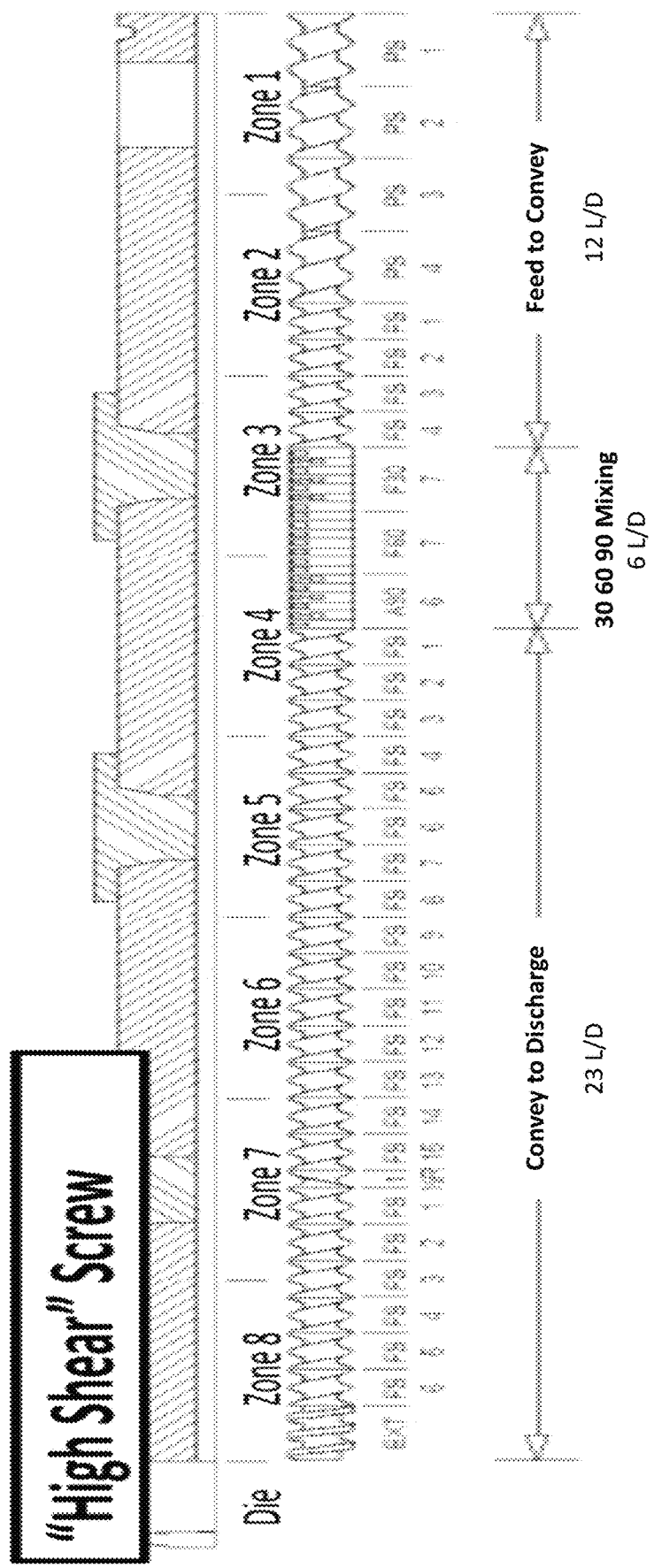
FIG. 6C illustrates exemplary "high shear" screw configurations according to one embodiment of the present invention.

In a preferred embodiment, an extruder is used to carry out the charge-modification and/or the crosslinking reaction. Exemplary devices for carrying out a method of the present invention include, but are not limited to, co-rotational and counter rotational twin screws, thermal kinetic compounders, high shear mixers, paddle mixers, static mixers blenders, open-type mixing mills, closed Banbury mixers, kneaders, single-screw extruders, vented screw extruders, and/or twin-screw extruders (e.g., a parallel or conical twin-screw extruders). FIGS. 6A, 6B, and 6C illustrate examples of exemplary screw configurations. A low shear screw configuration (FIG. 6A) includes a low number of or no shear inducing elements or zones along the screw profile. The shear inducing elements or zones include mixing, kneading, and/or reversing elements or zones which increase the torque or load on the extrusion motor for a given mass flow rate. A medium (FIG. 6B) and/or high shear (FIG. 6C) screw configuration includes an increased number of shear inducing elements or zones compared to a low shear screw configuration.

The charge-modification and/or crosslinking reaction is preferably performed and/or carried out as a single-stage direct extrusion process or a multi-stage extrusion process. In one embodiment, the charge-modification and/or crosslinking reaction includes in-line compounding. In another embodiment, the charge-modification and/or crosslinking reaction is carried out in an extruder with at least two reaction zones and the at least two reaction zones are used for one or more steps in the method for preparing the modified biopolymer. In one example, a biopolymer and at least one charge-modifying agent are reacted at a first reaction zone to form a charge-modified biopolymer and the charge-modified biopolymer is crosslinked at a second reaction zone to form a crosslinked, charge-modified biopolymer.

In one embodiment, the extruder is used as one complete reaction vessel, which allows for the reaction to occur along the entire length of the extruder. When two or more reaction zones are provided, the one or more process conditions (e.g., temperature, shear, etc.) in at least one reaction zone are preferably independent of the one or more process conditions in another reaction zone. In one embodiment, a different temperature and/or screw element is provided in at least one reaction zone compared to another reaction zone. In one example, a mixture of a biopolymer (e.g., starch), a plasticizer, a charge-modifying agent, and a catalyst are introduced into a feed zone in an extruder to form a homogeneous reaction blend in the extruder. Varying the temperature in one or more reaction zones in the extruder modifies (e.g., accelerates and/or slows) the reaction taking place in the extruder. In one embodiment, the reaction is accelerated by increasing the temperature in one or more reaction zones in the extruder. Additionally or alternatively, shear is introduced in one more reaction zones (e.g., zone 3 and/or zone 5 of an extruder) by having intense mixing elements in the screw to facilitate mixing and/or shear induced reaction. In yet another embodiment, the length of different reaction zones and/or the length of the extruder itself (e.g., by moving the injection zone closer to the end of the extruder) is varied or adjusted to modify the degree of reaction. The length of the extruder is generally defined as a length over diameter ratio or L/D.

In one embodiment, the extruder is used as a sequential reactor. In one example, a mixture of a biopolymer (e.g., starch), a plasticizer, and a charge-modifying agent are introduced into a feed zone of an extruder. The mixture is heated as it is transported through one or more reaction zones (e.g., one or more initial reaction zones, such as, e.g., zones 1 and 2) using conveying elements on the screw, and the charge-modifying agent reacts with the biopolymer to form a charge-modified biopolymer. Then, a crosslinking agent is added in either solid or liquid form into one or more reaction zones (e.g., zone 3) to form the crosslinked, charge-modified biopolymer. In another embodiment, following the reaction zone(s) in which the charge-modifying agent was added, an intense mixing screw element is placed on the screw in one or more reaction zones (e.g., in zone 4 and/or 5) to mix the crosslinking agent with the charge-modified biopolymer. In yet another embodiment, the crosslinking reaction is facilitated by different temperatures and/or different screw elements in one or more reaction zones (e.g., zone 4 and/or 5). In still another embodiment, a foaming agent (e.g., water) is injected into the extruder (e.g., in a reaction zone near the end of the extruder, such as, e.g., at zone 6), which causes the crosslinked, charge-modified biopolymer to expand as it exits the die.

In one embodiment, one or more reagents (e.g., the biopolymer) is in powder form when added to an extruder and is not in the form of a liquid or a paste. In another embodiment, the one or more reagents in powder form has a moisture content of about 20% by weight or less. In yet another embodiment, the biopolymer and/or the charged-biopolymer are added to the extruder in powder form and/or one or more additional reagents (e.g., a charge-modifier, a plasticizer, a crosslinker, etc.) are added to the extruder in powder form. The one or more additional reagents are added in the same or a different reaction zone than the biopolymer and/or the charge-modified biopolymer.

In one embodiment, components or reactants for one or more steps are dry mixed together prior to addition to the extruder. Alternately or in addition, two or more feeders (e.g., loss-in-weight feeders) are used that supply the components or reactants to be blended to the extruder. In one embodiment, multiple extruders are used to feed melts of the blend components, such as in co-extrusion. The components, reactants, and/or mixture blends are optionally sized by conventional means such as pelletization, granulation, and/or grinding.

One or more process conditions are modified to provide a particular modified biopolymer (e.g., a superabsorbent, ion exchange resin, etc.) and/or a particular property of a modified biopolymer (e.g., degree of charge modification, crosslinking, etc.). Example processing conditions include, but are not limited to, the type of extruder (e.g., single screw vs. twin screw); screw diameter (D); screw length (L) (L/D is often used to describe an extruder configuration); screw configuration (i.e., specific types of shear inducing sections within an extruder which may range from gentle conveying elements to more shear intensive elements that may be designed to enhance uniform mixing within the extruder and/or accelerate a chemical reaction); temperature (overall and profile along various extruder zones); screw RPM; number of separate extruder zones where both temperature can be changed independent of other zones and different ingredients of the formulation can be added; and feed rate of different formulation elements into different zones. In some embodiments, the combination of one or more independently controlled process variables influence dependent variables of residence time, mechanical energy input (SME) and/or shear. Changes in screw RPM may induce changes in shear, heating and/or residence time in the extruder.

The reacting and/or crosslinking step(s) are preferably carried out and/or performed in a homogeneous reaction blend. In a preferred embodiment, the reacting and/or crosslinking step(s) are carried out and/or performed using a reactive extrusion process. The reacting and/or crosslinking step(s) are preferably carried out at a temperature that avoids degradation of the biopolymer and/or the modified biopolymer. Advantageously, increasing the temperature of the reacting and/or crosslinking steps provides for an increased amount of charge-modification on the biopolymer if the temperature remains below the degradation temperature for the biopolymer. In one embodiment, the reacting and/or crosslinking step(s) are carried out at a temperature in a range of about 80° C. to about 200° C. (e.g., at a temperature in a range of about 80° C. to about 120° C., about 80° C. to about 150° C., about 90° C. to about 120° C., about 100° C. to about 120° C., about 100° C. to about 200° C., about 150° C. to about 180° C., or about 110° C. to about 130° C.). In another embodiment, the reacting and/or crosslinking step(s) are carried out at a temperature of about 140° C. or less. In a preferred embodiment, the reacting step is carried out and/or performed at a temperature in a range of about 100° C. to about 175° C. (e.g., about 120° C. to about 140° C. or about 100° C. to about 150° C.). In another preferred embodiment, the crosslinking steps are carried out and/or performed at a temperature in a range of about 120° C. or more (e.g., about 120° C. to about 175° C. or about 120° C. to about 140° C.).

As previously described, the reacting and/or crosslinking step(s) are preferably carried out in an extruder. In one embodiment, the reacting and/or crosslinking step(s) are carried out in an extruder with a residence time in a range of about 0.1 minutes to about 30 minutes (e.g., in a range of about 0.1 minutes to about 10 minutes, about 0.5 minutes to about 5 minutes, about 1 minute to about 10 minutes, about 1 minute to about 5 minutes, or about 1 minute to about 3 minutes). In another embodiment, the reacting and/or crosslinking step(s) are carried out in an extruder with a residence time of about 5 minutes. In yet another embodiment, increasing the residence time of the reacting and/or crosslinking step(s) provides for an increased amount of charge-modification on the biopolymer.

The extruder preferably has a screw RPM in a range of about 10 to about 500 RPM (e.g., about 10 to about 200 RPM, about 50 to about 200 RPM, about 100 to about 200 RPM, about 125 to 250 RPM, about 100 to about 500 RPM, or about 90 to about 130 RPM). In one embodiment, the reacting and/or crosslinking step(s) are carried out in an extruder having a screw RPM of about 120 RPM.

The extruder preferably has a Specific Mechanical Energy (SME) value of at least about 20 kJ/kg. In one embodiment, the extruder has a SME value in a range of about 20 kJ/kg to about 500 kJ/kg or about 25 kJ/kg to about 250 kJ/kg. The SME value may be measured using methods known to those of skill in the art.

In one embodiment, the modified biopolymer is treated after formation (i.e., a post-treatment). An example of a post-treatment is thermally treating a charge-modified biopolymer and/or crosslinked, charge-modified biopolymer post extrusion. In one embodiment, the post-treatment increases the degree of crosslinking present in the modified biopolymer and/or increases and/or improves charge density and/or charge modification of the modified biopolymer. In another embodiment, the post-treatment decreases a soluble gel fraction in the modified biopolymer. In yet another embodiment, the modified biopolymer in solid form undergoes a post-treatment. In still another embodiment, the post-treatment fine tunes and/or modifies the properties of the modified biopolymer.

In one embodiment, the post-treatment includes heating the modified biopolymer. In another embodiment, the post-treatment includes heating the modified biopolymer at a temperature in a range of about 80° C. to about 180° C. (e.g., about 100° C. to about 150° C. or about 120° C. to about 140° C.) for a period of time in a range of about 0.5 minutes to about 24 hours (e.g., about 5 minutes to about 180 minutes, or about 30 minutes to about 90 minutes). In yet another embodiment, the post-treatment includes heating the modified biopolymer at a temperature of about 110° C. to about 130° C. for a period of time in a range of about 60 minutes to about 120 minutes. In still another embodiment, the post-treatment includes heating the modified biopolymer at a temperature of about 130° C. to about 150° C. for a period of time in a range of about 10 minutes to about 50 minutes.

Unreacted reagents, soluble and/or low molecular weight species, and/or degradation products are preferably removed from the modified biopolymer (e.g., by rinsing, dialyzing, and/or the like the modified biopolymer). In one embodiment, unreacted reagents are removed from the modified biopolymer after a post-treatment. In another embodiment, the modified biopolymer is dried (e.g., at a temperature of about 40° C.).

In one embodiment, the modified biopolymer is further modified by grinding, milling, pelletizing, drawing, compressing, shaping, and/or the like to provide a formed modified biopolymer. The formed modified biopolymer may be of any shape and/or size. In one embodiment, the formed modified biopolymer is of substantially uniform size and/or shape (e.g., varying in size and/or shape by less than about 20%). In another embodiment, the formed modified biopolymer consists of a variety of particle sizes and/or shapes. As used herein, particle size refers to the diameter of particles. In yet another embodiment, the modified biopolymer is in the form of a bead, column, sheet, powder, particle (e.g., nanoparticles, microparticles, etc.), ribbon, fiber, film, pellet, and/or the like. In still another embodiment, the modified biopolymer is in the form of a particle having a diameter in a range of about 1 micron to 2,000 microns (e.g., in a range of about 10 microns to about 1000 microns, about 100 microns to about 1000 microns or about 300 to about 800 microns). In a preferred embodiment, the modified biopolymer has a particle size in a range of about 300 to about 800 microns or less than about 500 microns, which is preferable for use as an absorbent. In another preferred embodiment, the modified biopolymer has a particle size in a range of about 10 to about 150 microns or less than about 100 microns, which is preferable for use as an ion exchange material.

In one embodiment, the modified biopolymer lacks a granular structure and/or morphology. In another embodiment, the modified biopolymer lacks a crystalline structure.

In one embodiment, forming the homogeneous reaction blend includes melt blending at least one biopolymer and at least one charge-modifying agent, optionally with at least one plasticizer, a catalyst (e.g., an initiator), and/or optional additives. In another embodiment, at least one biopolymer, at least one charge-modifying agent, at least one plasticizer, and optionally a catalyst are combined to form a homogeneous reaction blend.

In one embodiment, a charge-modified starch is prepared and/or formed by forming a first homogeneous reaction blend in an extruder. The charge-modified starch is extruded and extrudate is optionally ground into a powder and/or pelletized. In another embodiment, the extrudate is then combined with chitosan, a plasticizer, and optionally a second charge-modifying agent to form a second homogeneous reaction blend.

In one embodiment, a homogeneous reaction blend is formed by combining a starch, at least one charge-modifying agent, optionally at least one plasticizer, and optionally at least one catalyst. The starch and the at least one charge-modifying agent are reacted to form a charge-modified starch. In another embodiment, the at least one charge-modifying agent is an acid, the optional at least one plasticizer is water and/or glycerol, and/or the optional at least one catalyst is sodium hypophosphite. In yet another embodiment, the reacting step includes reacting starch and the charge-modifying agent in a ratio in a range of 0.1:1 to 4:1 (charge-modifying agent: starch) (e.g., in a ratio in a range of 0.5:1 to 2:1 or 1:1 to 3:1).

In one embodiment, the charge-modified starch is crosslinked with another biopolymer, such as, for example, chitosan to form a crosslinked, charge-modified starch-chitosan. In another embodiment, the chitosan is charge-modified (e.g., protonated). In yet another embodiment, a charge-modified starch is combined with chitosan, at least one plasticizer, and optionally a charge-modifying agent. The charge-modified starch and chitosan are then crosslinked. In still another embodiment, a charge-modifying agent is an acid (e.g., acetic acid) and reacts with chitosan to form charge-modified chitosan. In one embodiment, the charge-modified chitosan is crosslinked with the charge-modified starch. In another embodiment, charge-modified chitosan is prepared by reacting chitosan and acetic acid in amount of about 1% to about 40% by weight of the chitosan (e.g., about 2.5% to about 13% or about 20% to about 40% by weight of the chitosan). Acetic acid is preferably added directly to the chitosan without the presence of water.

In one embodiment, the modified biopolymer is used as and/or to prepare consumer products, such as, but not limited to, diapers, hygiene products including feminine hygiene products, and/or a wound dressing. In another embodiment, the modified biopolymer is used as and/or to prepare an ion exchange resin and/or an absorbent. Thus, in one embodiment, the modified biopolymer is an ion exchange resin, ion removal resin, metal chelating and/or adsorbing resin, and/or an absorbent, including high performing absorbents (e.g., a superabsorbent). In yet another embodiment, the modified biopolymer removes contaminants from a fluid and/or absorb a fluid.

Further exemplary industries and/or uses for the modified biopolymer include, but are not limited to, water treatment, such as, for example, single-use ion exchange for water deionization (e.g., for laboratories and/or electronics), potable water desalination, potable water contaminant and heavy metals adsorbents, and an alternative to activated carbon for dechlorination; hygienic superabsorbent polymer (SAP) applications, such as, for example, baby diaper absorbents, adult incontinence absorbents, feminine hygiene absorbents; non-hygienic SAP applications such as, for example, sub-sea cable wraps, re-usable gel/ice packs, liquid waste solidification, pet pads, meat pads, concrete additives, removal of water from oil and/or hydrocarbons, liquid/solid separation, waste lagoon remediation, paint solidification, agricultural and horticultural soil amendments, mortuary absorbents, whole blood or blood mixture absorbents, medical waste solidification and spill control, drug delivery systems, and wound dressings; energy, such as, for example, hydraulic fracturing flowback water treatment or reuse, guar alternative hydraulic fracturing viscosifying agent, hydraulic fracturing friction reducer additive, lost circulation drilling fluid additive, oil refinery water treatment, cooling tower water softening, boiler feed water deionization, coal ash and flu vent remediation, and nuclear isotope removal; mining, such as, for example, metals mining water treatment, metal removal from mining solutions, and coal mining water treatment; environmental, such as, for example, pump and treat water remediation, in situ reactive barrier remediation, and sludge absorption and dewatering; packaging, such as, for example, biobased packaging films and biobased structural packaging; paper such as, for example, pulp and paper strength additives and/or coatings for paper; textiles such as, for example, textile adhesives, starch ester alternative for textile manufacture, and textile non-woven thickening agents; and/or construction, such as, for example, construction adhesive and/or binder in wallboard. In one embodiment, the modified biopolymer is useful in the paper industry, cosmetics, tissue engineering, hydrogels, drug delivery applications, or photonics applications. In another embodiment, the modified biopolymer is used as a flocculant and/or a coagulant.

In a preferred embodiment, the modified biopolymer is a superabsorbent that is incorporated into an absorbent hygiene article (e.g., diaper, incontinence product, feminine hygiene product, wound dressing) used to absorb one or more bodily fluids (e.g., urine, blood, feces, menses). In general, absorbent hygiene articles are constructed with a top layer (e.g., a topsheet layer), a back layer (e.g., a backsheet), and an absorbent core, wherein the absorbent core is located between the top layer and the back layer. In one embodiment, the absorbent core is attached to the top layer and/or the back layer via physical, mechanical, or chemical means. For example, in one embodiment, the absorbent core is attached to the top layer, the back layer, or any intermediate layers via an adhesive. In another embodiment, the absorbent core is attached to the top layer, the back layer, or any intermediate layers directly via stitched, woven, or other method of textile construction.

Structures are, in one embodiment, similar or identical to that of conventional hygiene products yet have the benefits of the materials and elements disclosed herein that provide biocompostability with improved performance and biodegradability compared to prior attempts at biodegradable hygienic articles. Examples of conventional products can be found described in U.S. Pat. No. 9,913,763, to inventors Ryu, et al., which is incorporated herein by reference in its entirety, and which discloses absorbent articles including a liquid-permeable topsheet, a liquid-impermeable backsheet, and an absorbent core located between said topsheet and said backsheet. Another example of a conventional product can be found described in U.S. patent application Ser. No. 15/309,658, to inventors Yu, et al., which is incorporated herein by reference in its entirety, and which discloses an absorbent article with a fluid acquisition layer being positioned between the body facing liner and the backsheet.

The top layer (e.g., topsheet) is the part of the absorbent hygiene article that comes in contact with a wearer's body (e.g., skin, hair). Notably, the top layer is referred to as the topsheet, topsheet layer, top layer, or uppermost layer and is preferably a non-woven layer. The topsheet is designed to allow fluids (e.g., urine, menses) to penetrate through the topsheet and aids in wicking moisture through the article to the absorbent core. The topsheet is generally formed from materials including, but not limited to, at least one woven material, at least one nonwoven material, at least one natural fiber, and/or at least one synthetic fiber, wherein the topsheet is produced via mechanical, chemical, or thermal means. In one embodiment, the topsheet is in contact with and/or is attached to at least one intermediate sheet, such as a transfer layer or an acquisition distribution layer (ADL), wherein the intermediate sheet provides a low-density layer that improves wicking performance. The intermediate layer further improves distribution of fluid within the non-woven core such that fluid is dispersed evenly and/or advantageously across an absorbent core. Advantageous dispersion of fluid, in one embodiment, includes distribution of the fluid to outer areas of an absorbent core, for example via physical structures such as pores, channels, creases, or varying textures. In another embodiment, the advantageous dispersion of fluid includes distribution of the fluid to outer areas and/or to inner or deeper layers of the absorbent core, for example, via physical structures such as pores, channels, creases, or varying textures. In one embodiment, the topsheet, any intermediate layers, and/or the absorbent core are sectionalized or embossed, wherein the absorbent core is constructed and arranged in patterns and shapes (e.g., embossed patterns and shapes) that draw moisture through the hygienic article in a distributed manner, such as compartmentalized triangles, squares, circles, or any variety of linear patterns. In one embodiment, the top layer is constructed from absorbent material and/or is integrated with the absorbent core, wherein the top layer is constructed from a biodegradable polymer. In another embodiment, the topsheet is constructed with the biodegradable materials described herein (e.g., including a biocompostable SAP) and is integrated within a hygienic material similar to the product described in U.S. patent application Ser. No. 15/369,886 to inventor Sookraj, which is incorporated herein by reference in its entirety. In one embodiment, the topsheet is impregnated with an SAP, wherein the SAP is dispersed within the topsheet. Additionally, the topsheet is operable to retain SAP particles via an outer and/or inner layer, wherein the outer and/or inner layer forms a void within the topsheet, and wherein the topsheet is optionally filled with an absorbent material, such as wood pulp fibers, cellulose fluff, or any other absorbent material known in the art of hygienic articles. The outer and/or inner layers are preferably constructed from a same material and are porous to allow wicking of moisture to the ADL and/or the absorbent core. In another embodiment, the topsheet, the ADL, the absorbent core, and/or any other layers include one or more integrated hygienic or aesthetic gels, oils, lotions, creams, or other fluid, such as antibiotic ointments, moisturizers, anti-odor agents, and/or scented products.

In one embodiment, intermediate layers have a higher absorbency than those used in traditional, non-biodegradable disposable diapers. For example, in one embodiment, an ADL has a high to medium absorbency, wherein the high absorbency is combined with an SAP that has a lower absorbency than traditional SAPs used in hygiene products. In another embodiment, the ADL is constructed with multiple sub-layers, wherein at least one layer of the ADL is operable to absorb fluid, and wherein at least one second layer of the ADL is operable to wick and distribute fluid across the absorbent article.

The ADL is, in one embodiment, constructed from nonwoven materials, such as polypropylene, polyethylene, polyethylene terephthalate, or any other standard synthetic used in ADL construction. In another embodiment, the ADL is constructed from woven or non-woven biodegradable or biocompostable materials, including cotton, silk, wool, cellulose, or hemp. For example, in one embodiment, the ADL is constructed from biocompostable wool similar to the materials produced from the process described in U.S. patent application Ser. No. 15/562,983, to inventors Hodgson, et al., for Wool treatment process and products, which is incorporated by reference herein in its entirety. In another embodiment, the ADL is constructed with properties similar to those described in U.S. patent application Ser. No. 15/778,842 to inventors Jackson, et al., which is incorporated by reference herein in its entirety and which describes an acquisition distribution laminate.

Additionally and alternatively, the absorbent article includes a surge layer, as described in U.S. patent application Ser. No. 16/095,403, to inventors Park et al., which is incorporated herein by reference in its entirety, wherein the surge layer rapidly accepts and temporarily holds the liquid prior to releasing the liquid into, for instance, the fluid intake layer and/or the absorbent core. In another embodiment, the absorbent article includes an absorbent layer between a topsheet and an intermediate layer (e.g., an ADL) and includes an absorbent core beneath the intermediate layer, wherein the absorbent core includes a superabsorbent polymer.

In one embodiment, the topsheet and/or the intermediate layers include an evenly distributed superabsorbent polymer (SAP). In another embodiment, the SAP is distributed such that an outer section of the hygienic absorbent article includes a lower concentration of SAP than an inner section. In one embodiment, the SAP is distributed in channels, patterns (e.g., circles, ellipses, lines, rectangles, triangles), and/or any other ideal distribution that provides ideal absorption (e.g., anatomic distribution). In one embodiment, the absorbent article includes both a biocompostable SAP and a non-biocompostable SAP, wherein the biocompostable SAP is distributed towards an outer region of the absorbent core, and wherein the non-biocompostable SAP is distributed towards an inner region of the absorbent core. Preferably, the total SAP distribution is approximately uniform across the absorbent core. In another embodiment, the biocompostable SAP and the non-biocompostable SAP are arranged and integrated within the absorbent core in channels, patterns, and/or shapes in alternating, connected, and/or mixed manner. Alternatively, the biocompostable SAP has a higher distribution towards an inner region of the absorbent core, and a non-biocompostable SAP has a lower distribution towards an outer region of the absorbent core.

In one embodiment, the SAP includes evenly distributed pores throughout the polymer. Preferably, the SAP includes pores that are approximately equal in size. In another embodiment, the SAP includes pores that are randomly distributed. In a further embodiment, the pores are random in size.

In another embodiment, pore size and fiber length of the absorbent core varies according to the material and construction used in addition to the SAP. In one embodiment, the absorbent core is non-porous.

In one embodiment, the absorbent core is constructed from an absorbent material (e.g., fluff or other fibers) and a superabsorbent polymer. In another embodiment, the absorbent core includes an absorbent material, a superabsorbent polymer, and/or one or more intermediate layers that contain the absorbent materials, wick fluid across the absorbent materials, and/or provide surge or additional absorbency in the article. The core is, in one embodiment, constructed with two cores, wherein the cores are positioned laterally, and wherein the cores form a central channel that wicks fluid. In another embodiment, two or more cores are positioned in patterns and shapes to improve absorbency in area and/or to improve fluid acquisition and distribution (e.g., through the formation of channels). In another embodiment, the cores are stacked, wherein channels, intermediate layers, and/or air space provides improved acquisition, distribution, and absorbency. In a further embodiment, the absorbent core is folded one or more times. For example, the core is folded into thirds, wherein the absorbent core forms a central, longitudinal channel. In another embodiment, the core is folded onto itself in a symmetrical or asymmetrical manner, and wherein the core forms a multi-layer core. For example, a left and a right side of the core are each folded multiple times symmetrically upon itself to form a three or six layer core. In another embodiment, the core is folded in half one or more times to create a multi-layer core. Additional folded constructions for an absorbent core can be found in U.S. patent application Ser. No. 14/634,718, to inventors Chmielewski, et al, which is incorporated herein by reference in its entirety. Notably, each of these core constructions include a superabsorbent polymer that is integrated, contained, and/or layered above, on, and/or within the absorbent core, wherein the superabsorbent polymer is preferably biocompostable and/or biodegradable.

The backsheet prevents fluids (e.g., urine, menses) from passing through the absorbent hygiene article and leaking (e.g., onto clothing, skin, etc.). The backsheet is formed from materials including, but not limited to, at least one woven material, at least one nonwoven material, and/or a polymeric and/or a thermoplastic film (e.g., polyethylene, polypropylene). In one embodiment, one or more of the at least one nonwoven material is a film-coated nonwoven material. The backsheet is generally designed to allow water vapor and air to permeate (i.e., "breathable") without allowing fluids to pass through the backsheet. In one embodiment, the backsheet is attached to the topsheet via, for example, an adhesive, stitching, or any other mechanical, physical, or chemical means known in the art. In another embodiment, the absorbent core is attached to the backsheet via any similar mechanical, physical, or chemical means.

The absorbent core absorbs and traps the fluids. The absorbent core is formed from materials including, but not limited to, cellulose fluff pulp, wood pulp fibers, and/or at least one superabsorbent material. In one embodiment, these materials are constructed into a core matrix, wherein the core matrix comprises a network of fibers, and wherein the fibers are constructed from natural or synthetic material. The absorbent core is, in one embodiment, constructed with a natural fluff material, such as cellulose fluff or cotton. In another embodiment, the absorbent core is constructed with synthetic fluff material, such as polyester, polyethylene, or polypropylene. In a further embodiment, the core matrix is constructed from "fluffless" or alternative non-woven materials, including a web of fabric with natural or synthetic materials, which is often used in feminine hygiene products. In one embodiment, the fabric is similar to the materials disclosed in U.S. Pat. No. 5,445,777 to inventor Noel, et al., which is incorporated herein by reference in its entirety. In one embodiment, between 0% and 50% of the core matrix includes an adhesive, a bonding agent, and/or a superabsorbent polymer. Bonding agents in one embodiment include resins, latex emulsions, and/or thermoplastic fibers.

"Curly" fibers are also considered as components of a fluffless core according to one embodiment of the present invention. Curly fibers are modified cellulose fibers, and are described in U.S. Pat. No. 6,780,201 to inventors Sun et al., which is incorporated herein by reference in its entirety.

In one embodiment, the topsheet, the backsheet, the absorbent core, and/or any intermediate layers are constructed from viscose, including fibers derived from wood pulp, bamboo, cotton, wool, silk, or any synthetic materials, including nylon, polyester. In another embodiment, the layers are constructed from rayon, spandex, Modal, or Micromodal material.

Preferably, the SAP is integrated into absorbent and distributing material, wherein the core is constructed with pores and channels that both trap any received fluid and direct the fluid to SAP particles. In a preferred embodiment, the article includes wood pulp fibers with distributed superabsorbent materials. In one embodiment, the absorbent core includes at least one absorbent foam (e.g., polyurethane foam, high internal phase emulsion (HIPE) foam). Preferably, the absorbent core is biodegradable, compostable, and/or recyclable. In one embodiment, the absorbent core includes absorbent and/or barrier layers between a superabsorbent material. Particle sizes of the superabsorbent materials are important to comfort, wherein a size, distribution, and shape of the particles affect the article perceived softness and the point at which a fluid is felt before an absorbent core is saturated. For example, a size of the particle is preferably hard enough to have sufficient structure without allowing any fluid to be felt by a wearer until the article is between 90% and 100% saturated. In one embodiment, the particle sizes are between approximately 100 and 850 micrometers. In another embodiment, the particle sizes are between approximately 150 and 650 micrometers. In one embodiment, at least 50% of the particle sizes are between 100 and 850 micrometers. In another embodiment, at least 85% of the particle sizes are between 100 and 850 micrometers. In yet another embodiment, at least 85% of the particle sizes are between 100 and 650 micrometers. In another embodiment, at least about 99.5% of the particle sizes are between 150 to 850 micrometers, with about 30% to about 35% of the particles being between about 500 micrometers to about 850 micrometers, about 25% to about 30% of the particles being between about 350 micrometers to about 500 micrometers, and about 150 micrometers to about 355 micrometers.

Particle sizes balance gel strength with absorption. For example, a large particle size generally corresponds to a high gel strength but a low rate of absorption, whereas a small particle size generally corresponds to a lower gel strength but a higher rate of absorption.

In another embodiment, SAPs of the present invention are combined with non-biodegradable, non-biocompostable, non-biorenewable, and/or non-recyclable SAPs. In one embodiment, biodegradable, biocompostable, biorenewable, and/or recyclable SAPs are between 10% and 100% of the SAPs used. In another embodiment, they are between 25% and 75% of the SAPs used. In yet another embodiment, they are between approximately 25% and approximately 40% of the SAPs used. In other embodiments, they are between approximately 30% to 40% of the SAPs used. In a further embodiment, they are approximately 50% of the SAPs used. In yet another embodiment, biodegradable, biocompostable, biorenewable, and/or recyclable SAPs make up between approximately 20% and 30% of the total SAPs in the absorbent core of the absorbent article. However, the biodegradable, biocompostable, biorenewable, and/or recyclable SAPs are operable to be any percentage of the SAPs in the core by weight, depending on the application of the core including the SAP. Biodegradable, biocompostable, biorenewable, and/or recyclable SAPs are, in one embodiment, distributed towards an outer or an inner section of the absorbent core. In another embodiment, the biodegradable, biocompostable, biorenewable, and/or recyclable SAPs are included in a secondary absorbent core layer, wherein the secondary absorbent core is positioned above or below a first absorbent core, and wherein the first absorbent core includes a non-biodegradable, non-biocompostable, non-biorenewable, and/or a non-recyclable SAP. In one embodiment, the absorbent cores are attached mechanically, physically, or chemically, such as through stitching, weaving, pinning, adhering, or any other method of attachment known in the art of hygienic products. In one embodiment, intermediate layers are positioned between a secondary and a first absorbent core, wherein the intermediate layers aid in wicking fluid between each of the cores according to an absorbency rate of each of the SAPs or cores as a whole. In another embodiment, the intermediate layers separate and/or surround the absorbent cores, wherein SAPs between a secondary and first core are prevented from mixing and/or interacting.

Mixtures of SAPs exhibit increased biodegradability with modified performance metrics. For example, in one acquisition time under load (ATUL) embodiment, a mixture of 25% biocompostable SAP (any of the modified biopolymers described in Examples 11-12 below) and 75% non-biocompostable SAP exhibits an acquisition time between 50 and 200 seconds for each of three equal dosing volumes of 0.9 wt % saline solution between 75 ml and 85 ml, and a rewet absorbency exhibits between 0% and 25% residual/release uptake of the dosing volume for each of the three doses. Rewet under load according to the present invention is performed at 0.70 psi. In another embodiment, a mixture of 50% biocompostable SAP (any of the modified biopolymers described in Examples 11-12 below) and 50% non-biocompostable SAP exhibits an acquisition time between 50 and 250 seconds for each of three dosing volumes between 75 ml and 85 ml, and a rewet absorbency exhibits between 0% and 50% residual/release uptake of the dosing volume for each of the three doses. In another embodiment, the biodegradable SAP alone exhibits an acquisition time between 50 and 500 for each of three dosing volumes between 75 ml and 85 ml, and a rewet absorbency exhibits between 0% and 75% residual/release uptake of the dosing volume for each of the three doses.

In another ATUL embodiment, a mixture of 25% biocompostable SAP (any of the modified biopolymers described in Examples 11-12 below) and 75% non-biocompostable SAP exhibits an acquisition time between 50 and 200 seconds for each of three equal dosing volumes between 75 ml and 85 ml, and a rewet absorbency exhibits between 0% and 5%, between 0% and 5%, and between 0% and 25% residual/release uptake of the dosing volume for each of the three doses, respectively. In another embodiment, a mixture of 50% biocompostable SAP (any of the modified biopolymers described in Examples 11-12 below) and 50% non-biocompostable SAP exhibits an acquisition time between 50 and 250 seconds for each of three dosing volumes between 75 ml and 85 ml, and a rewet absorbency exhibits between 0% and 5%, between 0% and 10%, and between 0% and 50% residual/release uptake of the dosing volume for each of the three doses, respectively. In another embodiment, the biodegradable SAP alone exhibits an acquisition time between 50 and 500 for each of three dosing volumes between 75 ml and 85 ml, and a rewet absorbency exhibits between 0% and 5%, between 0% and 25%, and between 0% and 75% residual/release uptake of the dosing volume for each of the three doses, respectively.

In another ATUL embodiment, a mixture of 25% biocompostable SAP (any of the modified biopolymers described in Examples 11-12 below) and 75% non-biocompostable SAP exhibits an acquisition time between 50 and 200 seconds for each of three equal dosing volumes between 75 ml and 85 ml, and a rewet absorbency exhibits between 0 ml and 5 ml, between 0 ml and 5 ml, and between 0 ml and 22 ml residual/release uptake of the dosing volume for each of the three doses, respectively. In another embodiment, a mixture of 50% biocompostable SAP (any of the modified biopolymers described in Examples 11-12 below) and 50% non-biocompostable SAP exhibits an acquisition time between 50 and 250 seconds for each of three dosing volumes between 75 ml and 85 ml, and a rewet absorbency exhibits between 0 ml and 5 ml, between 0 ml and 10 ml, and between 0 ml and 30 ml residual/release uptake of the dosing volume for each of the three doses, respectively. In another embodiment, the biodegradable SAP alone exhibits an acquisition time between 50 and 500 for each of three dosing volumes between 75 ml and 85 ml, and a rewet absorbency exhibits between 0 ml and 5 ml, between 0 ml and 22 ml, and between 0 ml and 65 ml residual/release uptake of the dosing volume for each of the three doses, respectively.

Figure 11A:
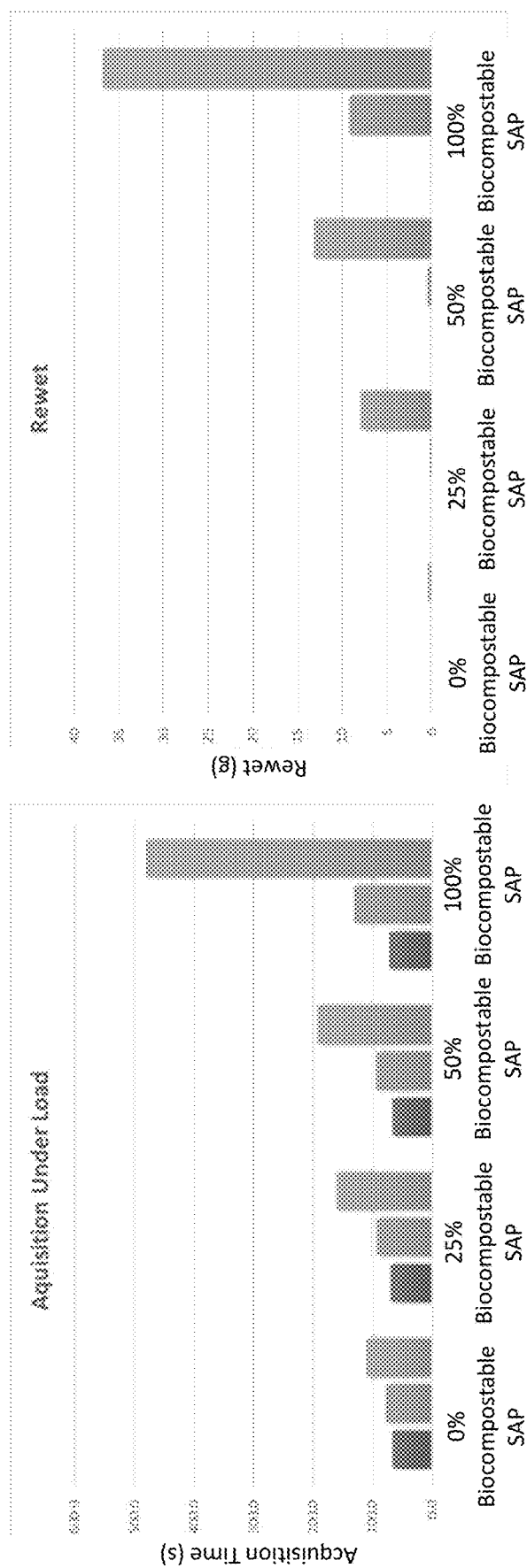
FIG. 11A is a pair of graphs illustrating acquisition under load and rewet absorbency for absorbent core constructs made with blends of superabsorbent polymers according to one embodiment of the present invention.

In one embodiment, the acquisition time is approximately within +/−10 seconds of Table A1, wherein each row of the chart corresponds to a dosing volume of 80 ml of 0.9 wt % saline. In another embodiment, the acquisition time is approximately equal to the data identified in FIG. 11A, wherein each column of the graph corresponds to a dosing volume of 80 ml of 0.9 wt % saline for a first, second, and third dose, respectively, for each combination of biocompostable and non-biocompostable SAP. In one embodiment, the non-biodegradable SAP in FIG. 11A, in TABLE A1, or in any of the above mixture examples has a CRC of 34 and an AUL of 23.

TABLE A1

Acquisition Time Under Load (ATUL)

| | 25% Biocompostable SAP | 50% Biocompostable SAP | 100% Biocompostable SAP |
|---|---|---|---|
| Dose 1 Acquisition Time (s) | 70 | 70 | 70 |
| Dose 2 Acquisition Time (s) | 95 | 95 | 120 |
| Dose 3 Acquisition Time (s) | 165 | 195 | 490 |

Figure 11B:
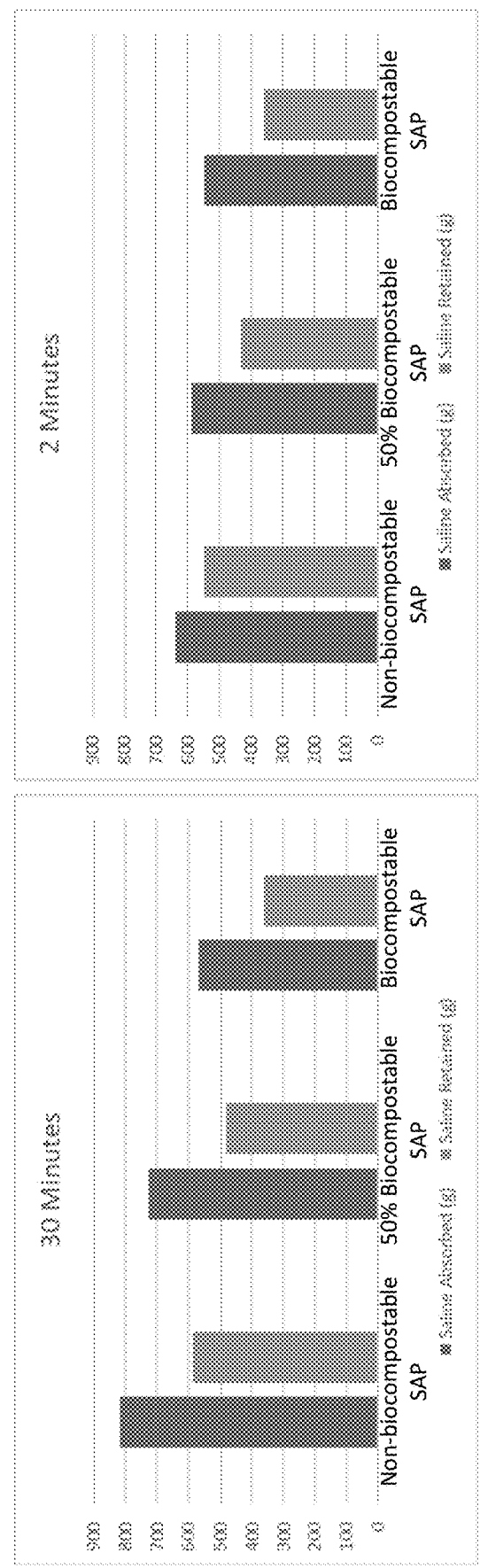
FIG. 11B is a pair of graphs illustrating a comparison of saline acquisition for absorbent core constructs made with blends of superabsorbent polymers according to one embodiment of the present invention.

FIG. 11B illustrates a comparison of saline absorbency at 30 minutes and 2 minutes for blends of non-biocompostable and biocompostable SAPs (any of the modified biopolymers described in Examples 11-12 below). In one embodiment, the absorption and retention is approximately within +/−5 grams of TABLE A2 and TABLE A3 below.

TABLE A2

Absorption and Retention (2 minutes)

| | 50% Biocompostable SAP | 100% Biocompostable SAP |
|---|---|---|
| Saline Absorbed (g) | 595 | 550 |
| Saline Retained (g) | 430 | 365 |

TABLE A3

Absorption and Retention (30 minutes)

| | 50% Biocompostable SAP | 100% Biocompostable SAP |
|---|---|---|
| Saline Absorbed (g) | 710 | 570 |
| Saline Retained (g) | 495 | 360 |

In one embodiment, absorption capacity of a baby diaper product containing a biocompostable SAP (any of the modified biopolymers described in Examples 11-12 below) submerged in approximately 0.9 wt % saline solution over 30 minutes is between approximately 500 ml and 800 ml.

The above ATUL and absorbency examples are, in one embodiment, exhibited in samples including an absorbent core with a total of 12 grams of SAP and 10 grams of wood pulp fluff and/or approximately a 55:45 ratio of SAP to fluff material as well as a non-woven film of approximately 25 gsm (grams per square meter), wherein an overall density of the absorbent core is approximately 0.2 g/cm$^3$. Rewet absorbency of the residual/release is preferably measured with filter paper.

In one embodiment, a biocompostable SAP has a maximum absorbency that is between 70% and 115% of a non-biocompostable SAP alone. In another embodiment, a mixture of 50% biocompostable SAP and 50% non-biocompostable SAP has a maximum absorbency that is between 80% and 115% of the non-biocompostable SAP alone. In one embodiment, the absorbency of the biocompostable SAP is less than or equal to that of the non-biocompostable SAP, yet the biocompostable SAP is operable to reach maximum capacity in a shorter range of time compared to the non-biocompostable SAP.

In one embodiment, a core used in the above examples was formed from a combination of wood pulp fluff and superabsorbent powder and was approximately 10 cm by 40 cm. The core was constructed and tested via the following procedures. A core former provided a vacuum of approximately 3 inches H$_2$O (approximately 0.108 psi) and created air flow through a rectangular chamber to form cores on a screen that were approximately 10 cm by 40 cm. A bristle brush was used to feed wood pulp fluff and the superabsorbent powder through a screen at an end of the core former to create a fine mix of wood pulp fluff and superabsorbent powder. Approximately six (6) additions of the superabsorbent and fluff mixture were added to the core former. In one embodiment, the ratio of superabsorbent to fluff is approximately 12 g of superabsorbent to 10 g of fluff. In another embodiment, the ratio of superabsorbent to fluff is approximately 55:45. Alternatively, the ratio of superabsorbent polymer to fluff is approximately 60:40. In other embodiments, the ratio of superabsorbent polymer to fluff is approximately 10:90, 20:80, 30:70, 40:60, 50:50 70:30, 80:20, 90:10, or any other ratio including all ratios falling between these ratios, depending on the application of the core. Resulting core material was deposited on a nonwoven film on a top of the screen. The non-woven used in these tests were approximately 25 g/m$^2$. After a core was formed, it was mechanically pressed (e.g., via a CLICKER PRESS). The resulting core was approximately 0.2 g/cm$^3$. The cores of the above tests were placed in commercially available chassis, including a backsheet, topsheet, and any intermediate layers (e.g., an ADL), wherein a core of the commercially available chassis was removed. All layers except for an original absorbent core remained in place and/or were reattached and/or re-adhered.

Absorption capacity of the above disclosed product was determined by submerging the fully assembled absorbent article in 0.9 wt % saline solution for 30 minutes. The absorbent article was then removed and allowed to drain for 5 minutes before being weighed. The absorption capacity was calculated by subtracting a dry weight of the absorbent article from a wet weight of the absorbent article. After a wet weight was measured, the wet absorbent article was placed into a vacuum box and covered with a thin rubber bladder. The article was compressed with a pressure of 14.5 inches of water (0.5233 psi) for 10 minutes, which removed any loose water from the article. The absorbent was article was again weighed to determine the retention weight, and the retention capacity was calculated by subtracting the dry weight of the diaper from the retention weight.

Acquisition time and rewet of the above disclosed product was determined by forming the product into a curved shape by attaching forward and rear tabs of the article together, resulting in a shape that mimicked the product in use. The absorbent article was placed in a plastic bowl for stabilization. 80 ml of 0.9 wt % saline was supplied to an inside absorbent region of the diaper via a 4.7 cm inner diameter tube. Acquisition time was determined by an amount of time elapsed between when supply was initiated and when fluid from the tube was completely absorbed. After determining acquisition time, the tube was removed, and the diaper was allowed to rest for 10 minutes. Multiple sheets of dry filter paper were placed on the absorbent region of the product for 2 minutes and a weight rested on the filter paper, resulting in a pressure of approximately 0.7 psi. The sheets of filter paper were removed and weighed, and rewet was calculated by subtracting the dry weight of the sheets of filter paper from the wet weight of the sheets of filter paper. The acquisition time and rewet tests were repeated twice more with a dose of 80 ml of 0.9 wt % saline.

In one embodiment, the absorbent core and/or any other secondary cores or intermediate layers are removable, such that a biodegradable, biocompostable, and/or recyclable core is easily removed from the hygienic article. For example, in one embodiment, the absorbent core is removably attached, adhered, and/or retained to a top layer, wherein the top layer is openable or removable, and wherein the absorbent core is operable to be removed independently or in conjunction with the other layers. In another embodiment, the absorbent core is operable to be inserted into at least one sleeve, at least one pouch, and/or at least one retaining element, wherein the absorbent core is easily removable. In a further embodiment, the topsheet, the absorbent core, and/or one or more intermediate layers are attached, adhered, or retained as a single removable piece. For example, in one embodiment, the absorbent core is removable, wherein an elastic retaining element holds a removable absorbent core by corners or edges of the absorbent core.

As previously described, the absorbent core preferably includes at least one superabsorbent material. The at least one superabsorbent material is a poly(meth)acrylate, a polyacrylamide, and/or a modified biopolymer as described herein. In one embodiment, the at least one superabsorbent material includes at least 5%, at least 10%, at least 15%, at least 20%, at least 25%, at least 30%, at least 40%, at least 50%, at least 60%, at least 70%, at least 80%, or at least 90% of a modified biopolymer. The modified biopolymer advantageously allows for the hygienic article to be biodegradable, biocompostable, recyclable, and/or environmentally friendly with increased performance compared to previous articles that are biodegradable.

In one embodiment, the absorbent hygiene article includes at least one fastener. In one embodiment, the at least one fastener includes hook tape and/or loop tape. In another embodiment, the at least one fastener includes at least one adhesive. In one embodiment, the at least one adhesive is protected with a removable paper prior to use. In yet another embodiment, the absorbent hygiene article includes wings (e.g., menstrual pad) or side cuffs (e.g., diaper).

Preferably, the absorbent hygiene article includes at least one element that is biodegradable, compostable, and/or recyclable, wherein the at least the absorbent core is biodegradable, compostable, and/or recyclable. In one embodiment, the absorbent core is biodegradable by way of being constructed with bioderived polymers that are easily broken down by natural biodegradable or compostable processes, such as bacterial anaerobic or aerobic digestion, and wherein byproducts of the breakdown processes are non-toxic to humans. The absorbent core includes, in one embodiment, biocompostable elements, wherein the elements of the absorbent core meet ASTM standards for biocompostability, such as biocompostability as tested according to ASTM 5338, wherein 90% of the polymer in the absorbent core degrades within 180 days in standard aerobic composting conditions. In another embodiment, the absorbent core is between 60% and 100% biocompostable. In another embodiment, each element of the hygiene article is biocompostable according to a similar range as the absorbent core. In a further embodiment, each element of the hygiene article is biocompostable except for a backsheet and/or adhesive or liquid impermeable materials. Whereas in the prior art, biodegradability was not feasible due in part to inefficiencies in materials and economic non-viability, the claimed invention advantageously integrates the biodegradable material disclosed above into a hygienic article with further biodegradable, compostable, and/or recyclable elements to ensure an environmentally friendly product that will disintegrate into non-toxic products.

In an alternative embodiment, the hygienic article is constructed into biocompatible or biocompostable materials for additional feminine hygiene applications, such as tampons. For example, in one embodiment, a tampon includes an outer wicking layer and a core impregnated with an SAP, including a biocompostable SAP as disclosed herein. In another embodiment, the hygienic article is an alternative feminine incontinence product, such as a fin, as described in U.S. Pat. No. 10,143,772 to inventor Berryman, which is incorporated herein by reference in its entirety, and wherein the feminine incontinence product includes a biocompostable SAP as disclosed herein. Alternatively, the hygienic article includes a biodegradable tampliner. In other embodiments, the hygienic article includes wound care products such as biodegradable wound care dressings including a protective backing, an absorbent core with an integrated SAP, a nonwoven layer, and a wound contact layer.

Figure 12:
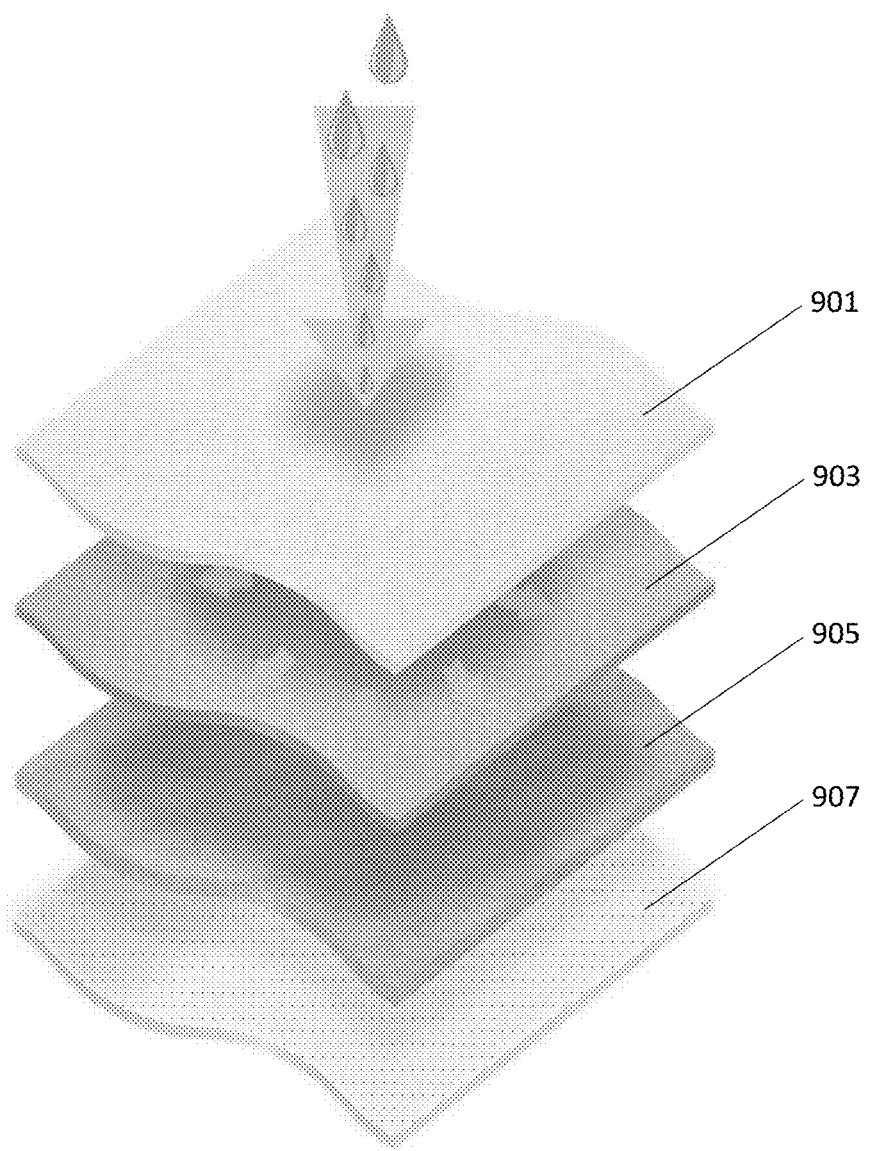
FIG. 12 illustrates layers of a sanitary absorbent article, including a topsheet, acquisition distribution layer, absorbent core, and backsheet according to one embodiment of the present invention.

FIG. 12 illustrates one embodiment of a layer distribution for the hygienic article, including a topsheet 901, an acquisition/distribution layer (ADL) 903, an absorbent core 905, and a backsheet 907. The absorbent core 905 preferably is impregnated with SAP particles for increased absorption. Advantageously, an absorbent core 905 includes at least a biocompostable and/or biodegradable SAP. In another embodiment, the absorbent core 905, includes biodegradable and/or biocompostable fluff and/or additional layers. In an alternative embodiment, the topsheet 901, the backsheet 907, and/or any intermediate layers are biodegradable, biocompostable, and/or recyclable.

Figure 13:
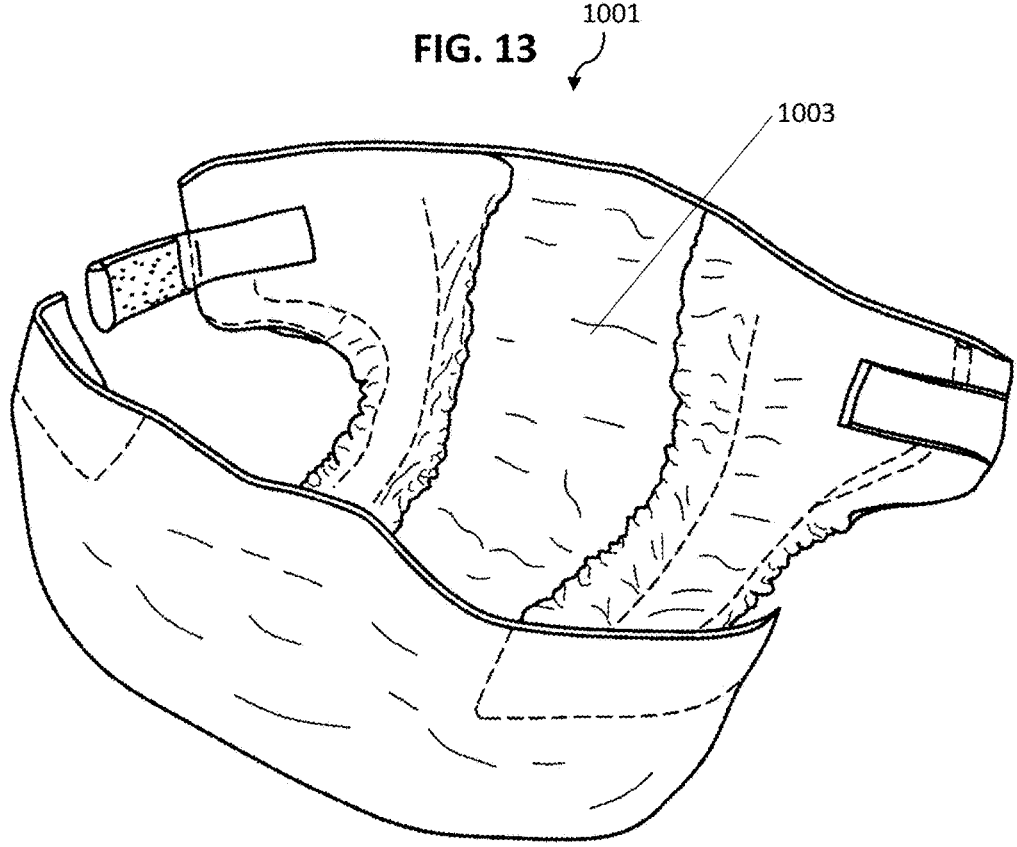
FIG. 13 illustrates a baby diaper with biocompostable, absorbent properties according to one embodiment of the present invention.

FIG. 13 illustrates on embodiment of a baby diaper 1001 including an absorbent area 1003, wherein the baby diaper 1001 is constructed with each the layers illustrated in FIG. 12. In one embodiment, the baby diaper 1001 does not include an ADL layer but only includes a topsheet, absorbent core with SAP particles, and a backsheet. In another embodiment, the diaper is modified for application to adult incontinence products. For example, the absorbent area 1003 is constructed with a smaller shape and is anatomically contoured to female or male genitalia and junctional areas.

Figure 14:
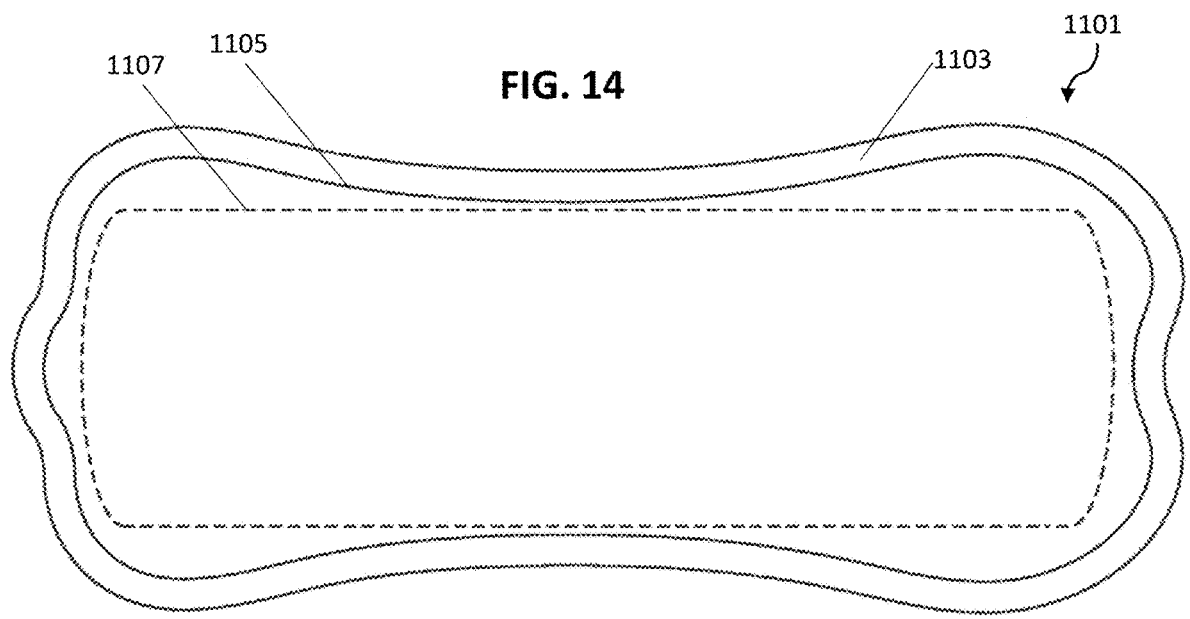
FIG. 14 illustrates a menstrual pad with biocompostable, absorbent properties according to one embodiment of the present invention.

FIG. 14 illustrates one embodiment of a female hygienic pad 1101 for menstrual hygiene, wherein the pad is constructed with a backsheet 1103, topsheet 1105, and absorbent core 1107 (demonstrated by hidden lines), wherein the absorbent core 1107 is positioned between the backsheet 1103 and topsheet 1105. In one embodiment, a rear of the hygienic pad 1101 includes an adhesive for attachment to a clothing article. Preferably, the adhesive is biodegradable, compostable, and/or recyclable, such as a soy or starch-based adhesive.

Figure 15:
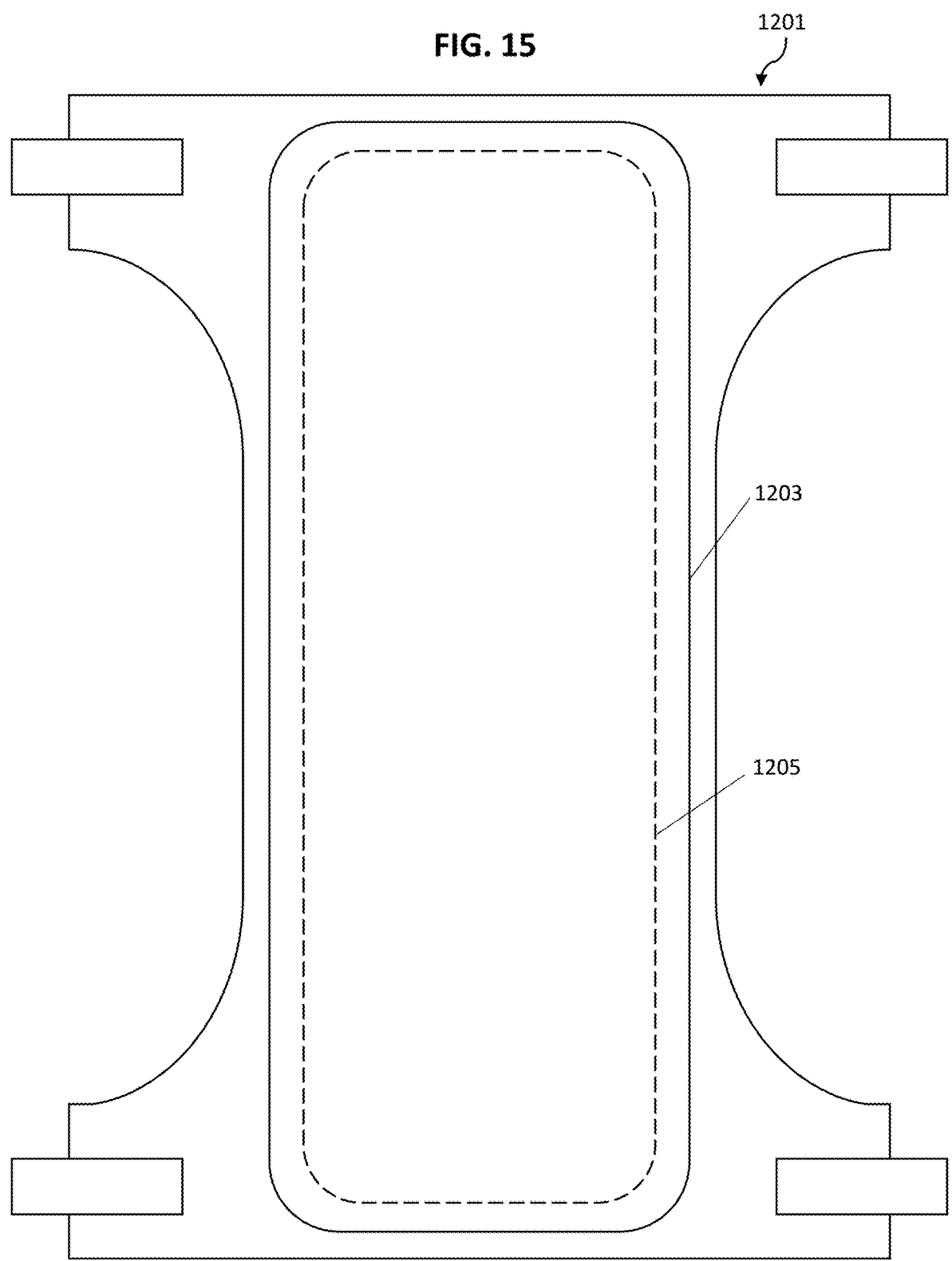
FIG. 15 illustrates an incontinence product with biocompostable, absorbent properties according to one embodiment of the present invention.

FIG. 15 illustrates another embodiment of an incontinence article 1201, wherein the incontinence article includes a topsheet 1203 and an absorbent core 1205. In this embodiment, the incontinence article 1201 does not include an acquisition distribution layer. The absorbent core is, in one embodiment, constructed with fluff and includes a biodegradable, compostable, and/or recyclable superabsorbent polymer.

A core forming apparatus is utilized in one embodiment of the present invention to create biocompostable absorbent sanitary cores with varying properties to mimic compositions run on commercial feminine hygiene lines. Variables manipulated include core weight, density, SAP/Fluff Ratio, fluff type, SAP type, and the components used in the prototype such as top sheet, ADL, and secondary core. Cores are formed using the core former and then tested according to the present invention by pressing a core using a hydraulic press to achieve the desired density, cutting them to size, and creating a hand laid pad consisting of a 2-mil polyethylene back sheet, the core, and a hydrophilic nonwoven top sheet adhered with adhesive spray. Specifically, cores are assembled based on their desired composition by inputting layers of fluff and SAP into the forming apparatus. Vacuum suction pulls the contents onto a forming drawer with a nonwoven present at the base as support. The core is weighed after the addition of all inputs to assess relative to the target weight where adjustments will be made if needed. After the target weight is reached, the core is pressed using a hydraulic press to achieve the target density within +/−0.01 g/cm$^3$. Preferably, dimensions for a core are 40 cm×10 cm; however, cores are operable to be smaller. Smaller cores are created from the 40 cm×10 cm core by cutting via a bandsaw, rolling die press, or any other method known in the art. After formed, supplemental test methods are utilized to verify the SAP distribution, SAP content, and SAP: Fluff ratio to further validate processing.

The prototype is assembled according to the present invention by laying down a 2-mil polyethylene sheet as a base layer and placing the core on top of the polyethylene sheet. In one embodiment, an additional fluff core which does not include superabsorbent is placed on top of the core. Additionally and/or alternatively, an acquisition distribution layer (ADL) is placed on top of the core or the additional fluff core to assist with fluid management. A hydrophilic top sheet is then adhered to the base layer with adhesive and the edges are trimmed to complete the prototype.

The core and the prototype are operable to be tested separately under the present invention. In some embodiments, cores are tested by using five circles cut out from cores or two 20 cm×8 cm pads out of each 40 cm×10 cm core. The free swell capacity (FSC), centrifuge retention capacity (CRC), absorption capacity, wicking, strikethrough time, acquisition time under load (ATUL), and rewet under load (RUL) of the core are operable to be tested.

FSC/CRC of Core Punchouts

To test the FSC and CRC of the core, the core circles or "punchouts" are placed in 4 inch by 4 inch MONETEREY BAY FILL YOUR OWN TEA BAGS "Tea Pot Size" tea bags and submerged in a reservoir of 0.9 wt. % NaCl or a menses simulant for a duration of 30 minutes. Following swelling, a 10-minute free hanging period occurs allowing gravity to remove extra fluid that transferred from the reservoir. At the end of the free hanging period, the weight of each sample is recorded, and the free swell is calculated on a gram per gram basis. The samples are then placed in a spin dryer and undergo 3 minutes of centrifuging at approximately 1300 RPMS. The weight of each sample is taken following the centrifuge component of the test and the centrifuge retention capacity is calculated on a gram per gram basis.

Liquid Absorption Capacity of Core Punchouts

To test the absorption capacity of core punchouts, cores are cut to 5 cm×5 cm squares and weighed prior to a submersion period. Samples are submerged in 0.9 wt. % NaCl or a menses simulant for a duration of 10 minutes followed by a 2-minute free hang. The weight of the sample is then recorded and the liquid absorption capacity is determined as the percentage of weight increase of the submerged and hung core punchout compared to the original core punchout.

Wicking

Wicking assesses the capillarity, or rate at which liquid is transported into the prototype core at a 30-degree incline. The core is weighed and placed on an inclined tray with a mesh grate suspending the core in the test liquid. After a duration of 30 minutes, the distance the liquid has permeated is measured using a ruler affixed to the tray. The core is then weighed to determine the total absorption.

Strikethrough Time/Rewet Under Load (RUL)

A fully assembled prototype including the core, the base layer, the top sheet, and optionally an ADL and/or a secondary core, is tested to determine the strikethrough time and rewet under load (RUL). These tests assess the time it takes the feminine hygiene prototype to uptake subsequent insults and retain the uptake when subjected to a pressure simulating the pressure applied to a feminine hygiene product in use. Prototypes are operable to be tested flat or curved and will undergo three doses of 7 mL of dyed 0.9 wt. % NaCl or a menses simulant, depending on the specifications for testing.

A 20 cm×7 cm plate with a 4.25 cm opening in the center is placed on top of the prototype prior to testing. The specified insult is dosed through a high-pressure peristaltic pump attached to a ring stand over the course of 30 seconds while a stopwatch and a timer set to 10 minutes 0 seconds are simultaneously started. As the insult is absorbed by the prototype, the fluid is visibly be engulfed below the opening in the plate. When this occurs, the stopwatch is stopped, and the time is recorded as the Strikethrough time (ST). At the conclusion of the remaining 10 minutes, a stack of qualitative 20-25 μm nominal pore size, 90 mm filter paper is placed on the insult point, dosed, and a 0.5 PSI weight is placed overtop for a duration of two minutes. The first dose includes a 10 mL dose, the second dose, includes a 15 mL dose, and the third dose includes a 20 mL dose, with each dose being part of a separate test. At the conclusion of the two minutes, the filter paper is weighed and the difference between the original weight of the filter paper and the weight of the filter paper after two minutes of being subjected to the 0.7 PSI weight is referred to as the rewet under load (RUL). This procedure is repeated two additional times for a total of three doses and three rewet measurements.

Incontinence pads are also operable to be constructed according to the method described above for feminine hygiene pads. The incontinence pads are operable to be tested for any performance metric as feminine hygiene pads. Additionally, the incontinence pads are operable to be tested for acquisition time under load free swell (ATULFS), rewet under load free swell (RULFS), acquisition time under load weighted swell (ATULWS), and rewet under load weighted swell (RULWS).

For testing of ATULWS and RULWS, prototype incontinence pads are tested flat or curved and undergo two doses of 30 mL of dyed 0.9 wt. % NaCl. A plate 20 cm×7 cm in dimension with a 4.25 cm opening in the center is placed on top of the prototype prior to testing. The specified insult is dosed through separatory funnel while a stopwatch and a timer set to 10 minutes 0 seconds are simultaneously started. As the insult is absorbed by the prototype, the fluid is visibly engulfed below the opening in the plate. When this occurs, the stopwatch is stopped, and the time is recorded as the acquisition time under load free swell (ATULFS). At the conclusion of the remaining 10 minutes, a stack of qualitative 20-25 μm nominal pore size, 90 mm filter paper and a dose is placed on the insult point, and a 0.5 PSI weight is placed overtop for a duration of two minutes. At the conclusion of the two minutes, the filter paper is weighed and the difference is referred to as the rewet under load Free Swell (RULFS). This procedure is repeated with the load and different doses. The first dose is approximately 10 mL, the second dose is approximately 15 mL, and the third dose is approximately 20 mL.

To obtain the acquisition time under load weighted swell (ATULWS) and the rewet under load weighted swell (RULWS), a plate 20 cm×7 cm in dimension with a 4.25 cm opening in the center is placed on top of the prototype followed by a stainless steel 0.5 PSI weight of the same dimensions. The specified insult is dosed through separatory funnel while a stopwatch and a timer set to 10 minutes 0 seconds are simultaneously started. As the insult is absorbed by the prototype, the fluid is visibly engulfed below the opening in the plate. When this occurs, the stopwatch is stopped, and the time is recorded as the acquisition time under load weighted swell (ATULWS). At the conclusion of the remaining 10 minutes, a stack of qualitative 20-25 μm nominal pore size, 90 mm filter paper and a dose is placed on the insult point and a 0.5 PSI weight is placed overtop for a duration of two minutes. At the conclusion of the two minutes, the filter paper is weighed and the difference is referred to as the rewet under load weighted swell (RULWS). This procedure is repeated with the load and different doses. The first dose is approximately 10 mL, the second dose is approximately 15 mL, and the third dose is approximately 20 mL.

The present invention is explained in greater detail in the following non-limiting Examples.

EXAMPLES

Example 1.1: Extruded Charge-Modified Biopolymer (Example of Citric Acid Grafted on to Starch at ~2 mm Scale)

A twin screw conical extruder manufactured by DSM, a parallel twin screw extruder manufactured by Leistritz, and a parallel twin screw extruder manufactured by Wegner were used to prepare charge-modified starch. The extruder properties are provided in Table 1. Various extruders listed here allow for demonstration of scalability from lab scale to production-relevant scale. Furthermore, multiple extruders allow for transposition of process parameters across a range of extruder configurations and size.

Additionally, the parallel twin screw extruders manufactured by Lestritz and Wegner supported multiple reactions zones, allowing for increased capabilities, including: temperature, screw, and injection profiles. Examples of temperature and injection profiles are found in Examples 1.2, 5.1, and 7, below.

TABLE 1

Extruder properties for a range of extruder configurations and sizes

| | Extruder Manufacturer | | | |
|---|---|---|---|---|
| | DSM | Thermo Fisher | Leistritz | Wegner |
| Extruder Model | Xplore | Process 11 | N/A | TX-52 |
| Residence Time | 0.25-10 mins | 0.25-5 mins | ~3 mins | ~3 mins |
| Screw Size (Screw Diameter) | 3 cm | 11 mm | 18 mm | 52 mm |
| L/D | 5 | 40 | 40 | 27 |
| Die Size | 1-2 mm | 0.5-11 mm | 1 mm & 4.5 mm | 2-4 mm |
| Rotation | Co-rotating screws | Co-rotating screws | Co-rotating screws | Co-rotating screws |
| Throughput | 0.05-0.2 kg/hr | 0.1-5 kg/hr | 0.5-8 kg/hr | 3-30 kg/hr |
| Type of heating | Electric | Electric | Electric | Electric |
| Number of heating zones | 1 | 8 | 8 | 1 |
| Type of Die | Single hole/circular | Single hole/circular | Single holes | 1 or 2 holes |

TABLE 1-continued

Extruder properties for a range of extruder configurations and sizes

| | Extruder Manufacturer | | | |
|---|---|---|---|---|
| | DSM | Thermo Fisher | Leistritz | Wegner |
| Additive zones | One | 8 | 3 feed ports | 2 feed ports, 1 extra for foaming agent |
| Type of cooling | Water | Water | Air | Water |

In preparing the charge-modified starch, the following parameters were varied: temperature, screw RPM, and amount of citric acid using each extruder. Table 2 sets forth the ranges for the temperature, screw RPM, and amount of citric acid tested using each extruder.

TABLE 2

Parameter ranges for charge-modified starch for each extruder

| Parameter | Range (DSM) | Range (Leistritz) | Range (Wegner) |
|---|---|---|---|
| Temperature Ranges (° C.) | 90-150 | 100-120 | 100-125 |
| RPM Ranges (RPM) | 60-200 | 120-200 | 120-200 |
| Citric Acid Ranges (wt % relative to starch) | 50-100 | 50-100 | 50-100 |

Starch (Native Corn Starch, Item 18321, Batory Foods, Des Plaines Ill.), citric acid (Item 756707, Univar, Downers Grove, Ill.) as a charge modifier and plasticizer, and sodium hypophosphate (SHP) (Item S1320, Spectrum Chemical, New Brunswick, N.J.) as a catalyst were combined and hand mixed in powder form. Powder mixtures were loaded into custom powder injectors and input into the extruder feed port. Various amounts of citric acid were added to the mixture as provided in Table 2. The resulting mixture was added to the extruder as a powder at varying extrusion conditions as provided in Table 2. The powder mixture was melt-blended in the extruder to form a homogeneous blend reaction in which the citric acid was grafted onto the starch to form a charge-modified starch, termed starch citrate. In some runs, this charge-modified starch was utilized as a precursor polymer to subsequently crosslink to another biopolymer as described in Example 5. Select samples underwent a thermal post treatment following extrusion by way of vacuum oven at 120° C. for 90 mins.

Table 3 provides specific parameters tested on the DSM extruder with responses described in Table 4 and described below. Each sample was titrated to determine its charge density, and analyzed via FTIR (at wavelengths of 1720 cm$^{-1}$) to determine each sample's relative carboxyl content via methods described below. Additionally, parameters such as DI uptake, and % extractables were measured as qualitative gauges of material performance.

TABLE 3

Process parameters for preparing charged-modified starch on a DSM extruder

| | Sample # | | | | |
|---|---|---|---|---|---|
| | Sample 1.1A | Sample 1.1B | Sample 1.1C | Sample 1.1D | Sample 1.1E |
| Temperature (° C.) | 140 | 140 | 100 | 140 | 125 |
| RPM | 120 | 120 | 120 | 120 | 120 |
| Post Treatment | Yes | No | Yes | Yes | Yes |
| Citric Acid (wt % relative to starch) | 150 | 150 | 50 | 50 | 75 |
| SHP (wt % relative to starch) | 20 | 20 | 20 | 20 | 20 |

Fourier Transform Infrared Spectroscopy (FTIR) is a measure of a samples' absorbance/transmittance of wavelengths in the IR spectrum. The intensity of absorbed IR radiation at a given wavelength can be correlated to particular covalent bonds. When data is normalized to the C—O stretch peak (~1000 cm$^{-1}$), relative peak intensities are used to estimate the amount characteristic groups on the polymer, where decreasing transmittance or, inversely, increasing absorbance indicates an increased degree of reagent grafting.

Alternatively, degree of substitution is preferably quantified utilizing titration, with FITR data being utilized to verify whether substitution occurred. In one embodiment of conductivity titration for calculating degree of substitution, a sample is dissolved in deionized $H_2O$ and acidified to pH<2 with HCl to ensure all charge modifier groups are present in the acid form (R—$CO_2H$). This solution is titrated with an NaOH solution. Electrical conductivity measured as titrant is added first decreases, then remains constant, then increases, producing two endpoints—the first corresponding to the neutralization of excess HCl and the second corresponding to the conversion of all charge modifier groups to the sodium salt form (R—$CO_2Na$). The degree of substitution (DS) is calculated using Eqn. 1

$$DS = \frac{A \times n_{CO2H}}{m_{ds} - (B \times n_{CO2H})} \quad (1)$$

where A is the molecular weight of the unsubstituted monomer, B is the molecular weight of the substituent, $m_{ds}$ is the mass of dry sample obtained by Eqn. 2

$$m_{ds} = \text{Moisture content (in decimal form)} \times \text{sample weight (grams)} \quad (2)$$

and $n_{CO2H}$ is the moles of anionic moieties obtained by Eqn. 3

$$n_{CO2H} = \frac{V2 - V1}{1000} x C_{NaOH} \quad (3)$$

where $V_2$ and $V_1$ are the volumes of titrant (in mL) corresponding to the second and first endpoints, respectively, and $C_{NaOH}$ is the concentration of the NaOH solution (in M).

Bonds of interest for biopolymers modified with citric acid (e.g., starch citrate) include the carboxyl (R—CO$_2$H) bond at ~1713 cm$^{-1}$, where decreasing transmittance or, inversely, increasing absorbance indicates an increased degree of charge density.

Back titration is a measure of charge density in anionic, charge-modified biopolymer samples. The results of this measurement technique scale with the FUR data. As described here in Example 1.1, along with Examples 1.2, 1.3, 2.1, 3.1, 3.2, and 3.3, 0.2-0.3 g of sample was exposed to 50 mL of 0.05 M NaOH solution for 1 hr. One drop of phenolphthalein (Item 3241N80, Thomas Scientific, Swedesboro, N.J.) was added and mixed into solution to act as a visual indication, approximating neutrality of the solution. A pH probe was used to monitor acid/alkaline nature of the solution during mixing and titration. The solution was then titrated with 0.05M HCl at, ~0.05 mL/second. The volume of HCl required to reach pH neutrality was recorded and assumed to be equivalent to the number of moles needed to neutralize excess NaOH in solution. The difference between the recorded moles and initial moles was then normalized to the original sample weight to yield a mol/g or meq/g charge density unit.

DI uptake is a measure of a sample's degree of swelling (i.e., its absorbency by weight under given conditions). DI uptake was measured by inserting ~0.25 g sample/cm in 33 mm diameter, of 12-14 kD dialysis tubing (Item 684219, Carolina Biological, Burlington, N.C.). The ends of tubing were sealed and labeled, then exposed to 20 mL DI water per gram of sample for 72 hours. DI water was replaced every 2-3 hours over the course of a 72 hr period. Samples were then removed from the dialysis tubing and weighed. Changes in weight between the initial and final (wet) measurements were normalized to initial mass to grams of DI water absorbed per gram of sample (g/g).

Samples were then dried using a forced air oven and/or a freeze dryer. Weight loss between dried sample and initial sample weight (pre dialysis) was used to calculate extractables as a % of initial sample (inverse of yield). These extractables reflect a measure of the amount of sample that elutes upon initial contact with water. This parameter qualitatively measures the mass fraction of unreacted moieties, plasticizer, and/or degraded polymeric products in a given sample.

TABLE 4

Properties of the charged-modified starch

| Sample # | FTIR (% Trans) | Titration (meq/g) | DI Uptake (g/g) | Extractables (%) |
|---|---|---|---|---|
| 1.1A | 36 | 5.9 | 3.4 | 89 |
| 1.1B | 96 | 1.9 | 2.8 | 87 |

TABLE 4-continued

Properties of the charged-modified starch

| Sample # | FTIR (% Trans) | Titration (meq/g) | DI Uptake (g/g) | Extractables (%) |
|---|---|---|---|---|
| 1.1C | 59 | 2.8 | 2.7 | 37 |
| 1.1D | 48 | 4.2 | 3.1 | 30 |
| 1.1E | 49 | 3.8 | 5.4 | 49 |

As can be seen from Tables 3 and 4, charge-modified starch was produced in the process example of reactive extrusion described here. % Transmittance as measured via FTIR is shown to decrease significantly below that of starch (94.5%) while titration values are shown to increase significantly over that of starch (0 meq/g).

Temperature and citric acid (charge modifying agent) concentration are the parameters where increasing inputs show increased charge density. Furthermore, inclusion of a thermal post treatment after extrusion also shows increasing charge density. Relative similarity and relatively low values of DI uptake parameters across indicate a lack of crosslinking. Extractable values are indicative of excess reagent and generally trend with charge modifier concentration. FTIR transmittance values achieved ranged from approximately 35-98% while charge density values achieved ranged from approximately 1 to 6.5 meq/g.

Example 1.2: Extruded Charge-Modified Biopolymer (Example of Citric Acid Grafted on to Starch at 18 mm Scale)

Figure 2:
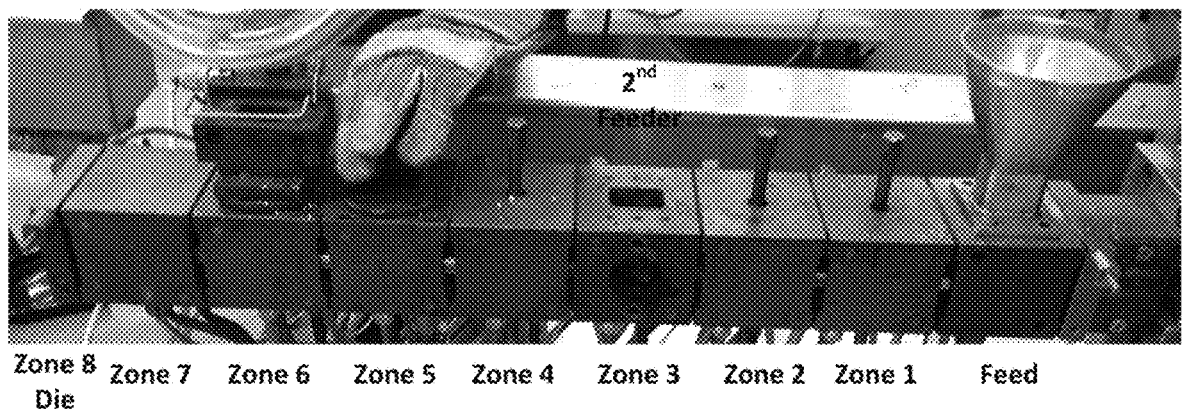
FIG. 2 illustrates a parallel twin screw extruder with multiple injection and reaction zones according to embodiments of the present invention.

A parallel twin screw extruder with multiple injection and reaction zones manufactured by Leistritz was also used to prepare charge-modified starch citrate. These experiments were performed to determine scalability and behavior of materials through varied reaction zones. The extruder properties are provided in Table 1 above. FIG. 2 illustrates the 8-zone extruder with injection ports in this configuration located prior to zone 1 and at zone 3.

Raw materials were prepared in a similar manner to extrusion as described above in Example 1.1. However, samples were mixed in 1 kg units and fed using gravimetric powder feeders manufactured by Brabender (Duisburg, Germany) to account for scale. Studies below utilized multiple injection and reaction zones to simulate full-scale extrusion processes. Screw profile utilized is described in FIG. 6B (medium shear screw). Powder samples of each of the following components: starch, citric acid, and SHP were fed into the primary injection zone (prior to zone 1) where the mixture was allowed to react at 120° C. Without wishing to be bound to any particular theory, at this temperature the citric acid dehydrates to yield an anhydride that reacts faster with the free hydroxyl groups. Temperature profiles for each zone are detailed in Table 5 below. Extrusion and composition parameters for starch citrate were varied as described in Table 6 below. In some runs, extruded samples in solid form were post-treated by placing the charge-modified starch in an oven at 120° C. for 90 minutes. Specific examples of process parameters and resulting responses are shown in Tables 7 & 8 below, respectively.

TABLE 5

Temperature and injection parameters for charge-modified starch via parallel twin-screw extruder

| Zone | | 1 | 2 | 3 | 4 | 5 | 6 | 7 | 8 |
|---|---|---|---|---|---|---|---|---|---|
| Temperature (° C.) | | 100 | 105 | 115 | 120 | 120 | 120 | 120 | 115 |
| Injection | Starch + Reagents | N/A | N/A | N/A | N/A | N/A | N/A | N/A | N/A |

TABLE 6

Parameter ranges for charge-modified starch via 18 mm, parallel twin-screw extruder

| | |
|---|---|
| Temperature Ranges (° C.) | 100-120 (see Table 5) |
| RPM Ranges (RPM) | 120-200 |
| Citric Acid Ranges (wt % relative to starch) | 50-100 |

TABLE 7

Process parameters for preparing charged-modified starch via 18 mm, parallel twin-screw extruder

| | Sample # | | | |
|---|---|---|---|---|
| | Sample 1.2A | Sample 1.2B | Sample 1.2C | Sample 1.2D |
| Temperature (° C.) | 100-120 (multiple zones) | 100-120 (multiple zones) | 100-120 (multiple zones) | 100-120 (multiple zones) |
| RPM | 100 | 160 | 100 | 170 |
| Post Treatment | Yes | Yes | Yes | Yes |
| Citric Acid (wt % relative to starch) | 100 | 50 | 75 | 75 |
| SHP (wt % relative to starch) | 20 | 20 | 20 | 20 |

TABLE 8

Properties of the charged-modified starch

| Sample # | FTIR (% Trans) | Titration (meq/g) | DI Uptake (g/g) | Extractables (%) |
|---|---|---|---|---|
| 1.2A | 35 | 6.55 | 1.7 | 32 |
| 1.2B | 53 | 2.10 | 1.1 | 10.5 |
| 1.2C | 54 | 2.0 | 1.8 | 45 |
| 1.2D | 43 | 5.8 | 1.3 | 10 |

As can be seen from Tables 7 and 8, this work demonstrated the feasibility of producing a charge-modified starch via a reactive extrusion process. % Transmittance as measured via FTIR is shown to decrease significantly below that of starch (94.5%) while titration values are shown to increase significantly over that of starch (0 meq/g). Furthermore, it should be noted that titration and FTIR values have a positive correlation. Increased RPM in this method improves the degree of charge modification as a response to increased shear.

Example 1.3: Extruded Charge-Modified Biopolymer (Example of Citric Acid Grafted on to Starch at 52 mm Scale)

A parallel twin screw extruder manufactured by Wegner was used to prepare charged-modified starch and to further demonstrate scaling. The extruder properties are provided in Table 1.1 above. Screw profile utilized largely conforms to a purely conveying screw as described in FIG. 6A (low shear screw).

Raw materials for charge-modified starch were prepared in a similar manner to the extrusion processes described above. However, samples were mixed and injected in ~2 kg units to account for the larger scale and continuous nature of this extruder. Extrusion and composition parameters for starch citrate were varied as described in Table 9 below. Specific examples of process parameters and resulting responses are shown respectively in Tables 10 and 11 below, respectively. In some runs, extruded samples in solid form were post-treated by placing the charge-modified starch in an oven at 120° C. for 90 minutes.

TABLE 9

Parameter ranges for charge-modified starch via 52 mm, parallel twin-screw extruder

| | |
|---|---|
| Temperature Ranges (° C.) | 100-125 |
| RPM Ranges (RPM) | 120-200 |
| Citric Acid Ranges (wt % relative to starch) | 50-100 |

TABLE 10

Process parameters for preparing charged-modified starch via 52 mm, parallel twin screw extruder

| | Sample # | |
|---|---|---|
| | Sample 1.3A | Sample 1.3B |
| Temperature (° C.) | 110 | 120 |
| RPM | 120 | 100 |
| Post Treatment | Yes | Yes |
| Citric Acid (wt % relative to starch) | 66 | 66 |
| SHP (wt % relative to citric acid) | 20 | 20 |

TABLE 11

Properties of the charged-modified starch

| Sample # | FTIR (% Trans) | Titration (meq/g) | DI Uptake (g/g) | Extractables (%) |
|---|---|---|---|---|
| 1.3A | 65 | 2.9 | N/A | 64 |
| 1.3B | 69 | 2.4 | N/A | 68 |

This work demonstrated the feasibility of producing charge-modified starch via a reactive extrusion process. % Transmittance as measured via FTIR is shown to decrease significantly below that of starch (94.5%) while titration values are shown to increase significantly over that of starch (0 meq/g). Examples 1.1E, 1.2C and 1.3 are used to compare samples at similar processing conditions. It is concluded from the similar responses that parameters listed in these examples are transposable across a significant range of extruder sizes (representing from laboratory benchtop to commonly-used industrial sizes).

Example 2.1: Extruded Charge-Modified Biopolymer (Examples of Additional Anionic Charge Modifiers Grafted on to Starch)

In addition to citric acid, additional anionic charge modifiers are demonstrated in the example below. Starch was charged modified using maleic anhydride (Item 63200-500G-F, Sigma-Aldrich, MO, St. Louis) a catalyst (NaOH, Reagent ACS, Item 630, GFS Chemicals, Powell Ohio), and plasticizer to form an anionic starch. Table 12 sets forth the ranges for the temperature, screw RPM, and amount of reagent tested using a Process 11, 11 mm parallel twin screw extruder as described in Example 1.1, above. Screw profile utilized is described in FIG. 6B (medium shear screw). Specific examples of process parameters and resulting responses are shown in Tables 13 and 14 below, respectively. In some runs, extruded samples in solid form were post-treated by placing the charge-modified starch in an oven at 120° C. for 90 minutes.

In addition to charge density (measured via titration), solubility of each sample was also studied. Here, purified samples (as described in the dialysis process above) are used. 0.25 g of sample is mixed into in a beaker with 25 mL of DI water at 60° C. Beaker with mixture is set stirring on hotplate and held at 60° C. for 15 mins. Mixture is then centrifuged at 250 g (1800 RPM & 7 cm radius) for 20 mins to separate solid fraction from the liquid fraction, including dissolved solids. A pipette is then used to decant the liquid layer and discarded. Aluminum weigh pans stored in a desiccator and with predetermined weights are used to collect remaining solids. Weigh pans and solids are then dried in a forced air oven for 48 hrs at 40° C. Weigh pans and samples are removed from the forced air oven and immediately weighed. Sample weights as a fraction of initial weights are recorded as a % Solubility.

TABLE 12

Parameter ranges of the anionic-modified starch on an 11 mm, parallel twin screw extruder

| | |
|---|---|
| Temperature Ranges (° C.) | 85-140 |
| RPM Ranges (RPM) | 10-500 |
| Maleic Anhydride Ranges (wt % relative to starch) | 5-120 |
| Catalyst (NaOH) Ranges (wt % relative to starch) | 2-60 |
| Plasticizer Ranges (wt % relative to starch) | Water, Glycerol, & Water/Glycerol mixes at 40% |

TABLE 13

Process parameters for preparing anionic-modified starch via 11 mm, parallel twin screw extruder

| | Sample # | |
|---|---|---|
| | Sample 2.1A | Sample 2.1B |
| Temperature (° C.) | 110 | 110 |
| RPM | 50 | 50 |
| Post Treatment | No | No |
| Maleic Anhydride Ranges (wt % relative to starch) | 30 | 60 |
| Catalyst (NaOH) Ranges (wt % relative to starch) | 12 | 24 |
| Plasticizer (wt % relative to starch) | Water (40%) | Water (40%) |

TABLE 14

Properties of the Anionic Modified Starch

| Sample # | FTIR (% Trans) | Titration (meq/g) | Solubility (%) |
|---|---|---|---|
| 2.1A | 83 | 3.26 | 76 |
| 2.1B | 73 | 5.11 | 84 |

Data indicated that a charge-modified starch was produced via a reactive extrusion process. % Transmittance as measured via FTIR is shown to decrease significantly below that of starch (94.5%) while titration and solubility values are shown to increase significantly over that of starch (0 meq/g and 7%, respectively). Ranges of charge density varied from 1.3-6.3 meq/g, and solubility varied from 27-86%. The level of charge modification of the starch increased with increasing reagent concentration. Data are further confirmed via increasing solubility with increasing charge density.

Example 2.2: Extruded Charge-Modified Biopolymer (Examples of Cationic Charge Modifiers Grafted on to Starch)

In addition to anionic charges, starch was charge-modified to form a cationic starch. The cationic charge-modified starch was prepared by varying the following parameters: temperature, screw RPM, amount of charge modifying reagent (glycidyltrimethylammonium chloride [Sigma Aldrich Item 50053-1L]), catalyst (Sodium Hydroxide), and plasticizer content. Table 15 sets forth the ranges for the studied parameters in the Leistritz, 11 mm extruder.

TABLE 15

Parameter ranges of the anionic-modified starch on an 11 mm, parallel twin screw extruder

| | |
|---|---|
| Temperature Ranges (° C.) | 85-140 |
| RPM Ranges (RPM) | 10-500 |
| Glycidyltrimethylammonium chloride (wt % relative to starch) | 5-150 |
| Catalyst (NaOH) Ranges (wt % relative to starch) | 2-60 |
| Plasticizer Ranges (wt % relative to starch) | Water, Glycerol, & Water/Glycerol mixes at 40% |

Starch powder was mixed with a catalyst (NaOH) in powder form. Plasticizer was then added to the mixture containing the starch and catalyst and mixed well by hand. The mixture was then input into the extruder.

Table 16 provides specific parameters tested with test responses described in Table 17. Note, temperature settings were set to apply a uniform temperature for all heating zones. Although temperature profiles were utilized in other experiments, they are not detailed here. Screw profile utilized is described in FIG. 6B (medium shear screw). Each sample was tested to determine its charge density (degree of substitution) via elemental analysis (measuring nitrogen).

Elemental analysis is used to measure charge density for cationic charge-modified biopolymer samples, whereas titration is used to measure charge density for anionic charge-modified biopolymer samples. Elemental analysis was carried out by means of Perkin Elmer 2400 CHNS Analyzer: The Perkin Elmer 2400 was used to determine total elemental carbon, nitrogen, hydrogen, or sulfur by total combustion. The Degree of Substitution (DS) was determined by nitrogen and calculated according to Equation (4) below:

$$DS = 162.15 \times \frac{\% N}{1401} - 151.64 \times \% N, \quad \text{Equation (4)}$$

where DS is the degree of substitution and % N is the measured nitrogen content. Furthermore, % N is nearly 0% but a non-zero number (e.g., 0.002). It is subtracted from all measurements for precision. Please check and confirm Equation 4. This seems to yield a negative number. You're subtracting what value from what measurements for precision?

TABLE 16

Process and formulation parameters for preparing cationic charge-modified starch

| | Sample # | | | |
|---|---|---|---|---|
| | Sample 2.2A | Sample 2.2B | Sample 2.2C | Sample 2.2D |
| Temperature (° C.) | 90 | 120 | 90 | 90 |
| Plasticizer (wt % relative to starch) | Water (40%) | Water (40%) | Water (40%) | Water (40%) |
| RPM | 100 | 120 | 50 | 50 |
| Post Treatment | No | No | No | Yes |
| Glycidyltrimethylammonium chloride (wt % relative to starch) | 4 | 85 | 30 | 30 |
| NaOH (wt % relative to starch) | 1.2 | 24 | 12 | 12 |

TABLE 17

Properties of the cationic charged-modified starch

| Sample # | Degree of Substitution* | Solubility (%) |
|---|---|---|
| 2.2A | 0.035 | 28 |
| 2.2B | 0.12 | 68 |
| 2.2C | 0.19 | 76 |
| 2.2D | 0.21 | 13 |

*Degree of substitution as measured by nitrogen content

Once again, a charge-modified starch was produced in this reactive extrusion process. Degree of substitution and solubility values were significantly greater than that of starch (0 DS, and 0.4% solubility, respectively) and demonstrate charge modification of a cationic starch via reactive extrusion. A range of DS values are produced. The DS values achieved here are significantly higher than previously reported values of DS for cationic starch produced via reactive extrusion.

In example 2.2D, inclusion of post treatment shows increased degree of substitution with simultaneous reduction in solubility indicating presence of crosslinking as discussed in later examples.

Example 3.1: Extruded Charge-Modified Biopolymer (Demonstration of Charge Grafting onto Hemicellulose)

In addition to starch, additional biopolymers were utilized to demonstrate charge modification. Hemicellulose (Xylan from Beechwood>=90%, Item X4252, Sigma Aldrich, St. Louis Mo.) was charge-modified with citric acid to form an anionic hemicellulose using the DSM extruder described in Example 1.1. In preparing the charge-modified hemicellulose, the following parameters were varied: temperature, screw RPM, and amount of citric acid. Table 18 sets forth the ranges for the temperature, screw RPM, and amount of citric acid tested using the twin screw conical extruder.

TABLE 18

Parameter ranges for charge-modified hemicellulose via twin screw conical extruder

| Temperature Ranges (° C.) | 90-150 |
|---|---|
| RPM Ranges (RPM) | 50-200 |
| Citric Acid Ranges (wt % relative to hemicellulose) | 40-150 |

Figure 3:
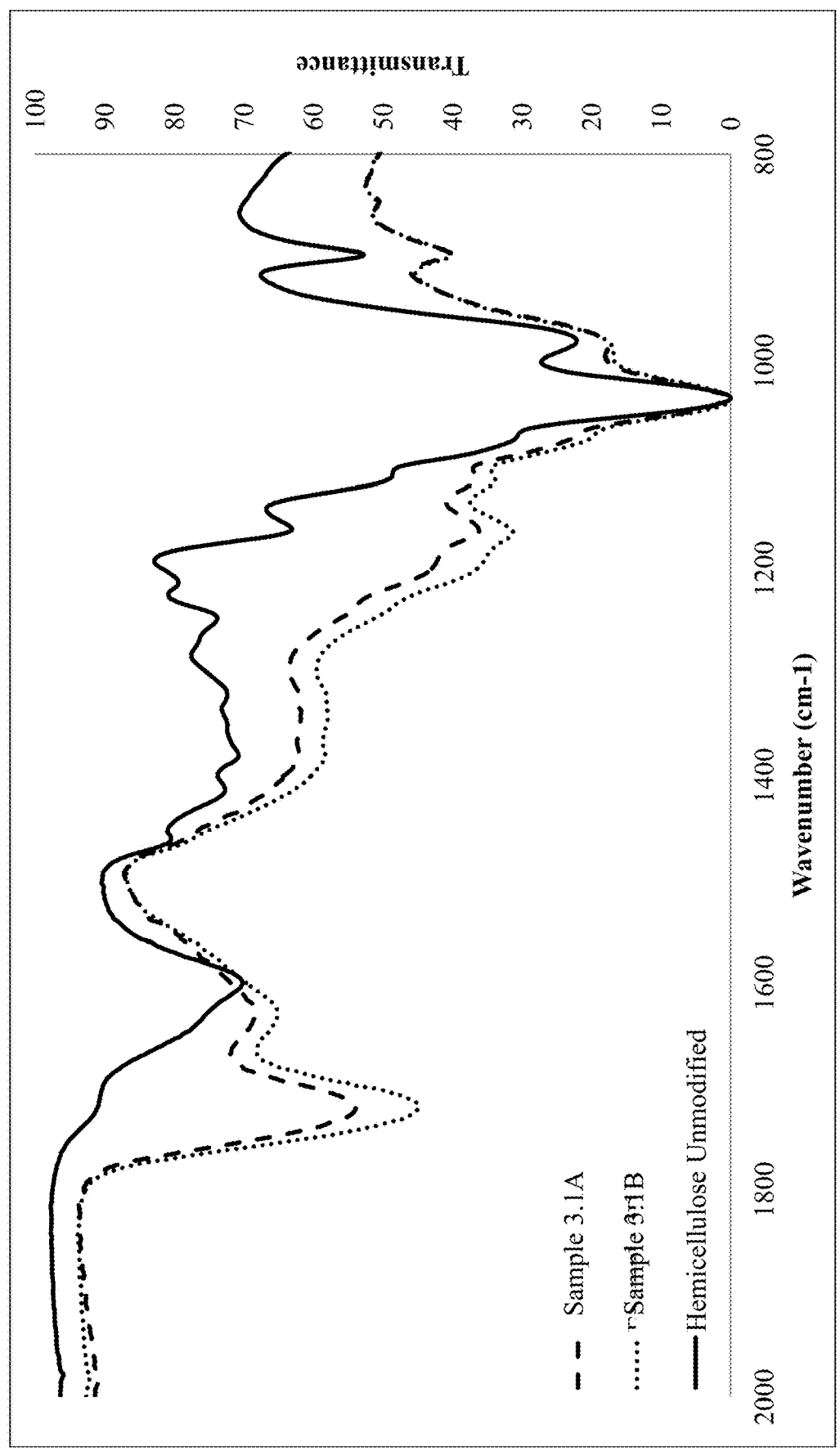
FIG. 3 illustrates Fourier-Transform Infrared Spectroscopy (FTIR) spectra for unmodified hemicellulose and charge-modified hemicellulose according to embodiments of the present invention.

Reagents in powder form were hand mixed in 50 g batches, loaded into the extruder using custom powder injectors, and fed into the extruder at feed rates determined to be relatively and qualitatively consistent. Table 19 provides specific parameters tested with test responses described in Table 20. The FTIR spectra for the charge-modified hemicellulose and for unmodified hemicellulose is provided in FIG. 3. Charge density values are reported according to the titration method described in Example 1.1. It should be noted that in this example, charge density values of the raw materials are measured and then subtracted from measured values to show a degree of change in charge density above that of the raw biopolymer.

TABLE 19

Process and formulation parameters for preparing charge-modified hemicellulose

| | Sample # | |
|---|---|---|
| | Sample 3.1A | Sample 3.1B |
| Temperature (° C.) | 140 | 140 |
| RPM | 120 | 120 |
| Post Treatment | No | Yes |
| Citric Acid (wt % relative to hemicellulose) | 150 | 150 |
| SHP (wt % relative to citric acid) | 20 | 20 |

TABLE 20

Properties of the charge-modified hemicellulose

| Sample # | FTIR (% Trans) | Titration (meq/g) |
|---|---|---|
| 3.1A | 81.4 | 1.66 |
| 3.1B | 53.4 | 4.68 |

A charge-modified hemicellulose was produced via reactive extrusion. FTIR analysis shows % Transmission values significantly lower than that of unmodified hemicellulose (91%) and titration values significantly greater than that of unmodified hemicellulose (0 meq/g), indicating charge modification of the hemicellulose.

Example 3.2: Extruded Charge-Modified Biopolymer (Demonstration of Charge Grafting onto Pectin)

Pectin (Item 76282, Sigma Aldrich, St. Louis, Mo.) was charge-modified to increase the anionic property of pectin by grafting additional carboxylic acid groups onto pectin using the DSM extruder described in Example 1.1. Experimental methods followed those in Example 3.1. Table 21 sets forth the ranges for the temperature, screw RPM, and amount of citric acid tested using the twin screw conical extruder.

TABLE 21

Parameter ranges for charge-modified pectin via twin screw conical extruder

| Temperature Ranges (° C.) | 90-150 |
|---|---|
| RPM Ranges (RPM) | 50-200 |
| Citric Acid Ranges (wt % relative to pectin) | 40-150 |

Figure 4:
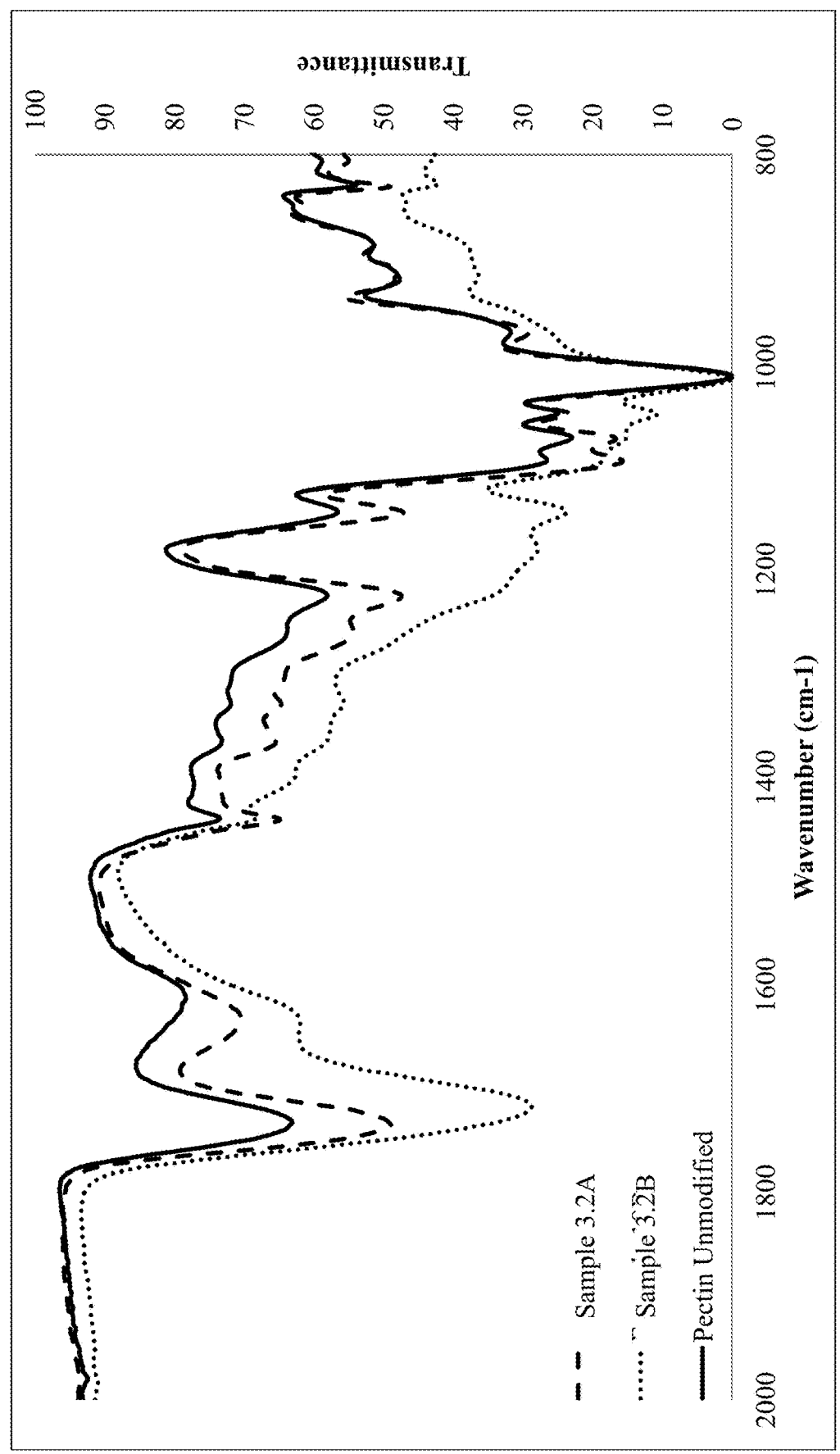
FIG. 4 illustrates FTIR spectra for unmodified pectin and charge-modified pectin according to embodiments of the present invention.

Table 22 provides specific parameters tested with test responses described in Table 23. If the sample underwent a post treatment, then the sample was placed in a vacuum oven at 120° C. for 90 mins. Each sample was tested to determine its charge density (meq/g), and absorbance/transmittance via Fourier Transform Infrared Spectroscopy (FTIR) at 1720 cm$^{-1}$. The FTIR spectra for the charge-modified pectin and for unmodified pectin is provided in FIG. 4. Charge density values are reported according to the titration method described in Example 1.1. It should be noted that in this example, charge density values of the raw materials are measured and then subtracted from measured values to show a degree of change in charge density above that of the raw biopolymer.

TABLE 22

Process and formulation parameters for preparing charge-modified pectin

|  | Sample # | |
| --- | --- | --- |
|  | Sample 3.2A | Sample 3.2B |
| Temperature (° C.) | 140 | 140 |
| RPM | 120 | 120 |
| Post Treatment | No | Yes |
| Citric Acid (wt % relative to pectin) | 150 | 150 |
| SHP (wt % relative to citric acid) | 20 | 20 |

TABLE 23

Properties of the charged-modified pectin

| Sample# | FTIR (% Trans) | Titration (meq/g) |
| --- | --- | --- |
| 3.2A | 59.1 | 4.96 |
| 3.2B | 26.6 | 5.72 |

A charge-modified pectin was produced via reactive extrusion. FTIR analysis shows % Transmission values significantly lower than that of unmodified pectin (63%) and titration values significantly greater than that of unmodified pectin (0 meq/g), indicating charge modification of the pectin.

Example 3.3: Extruded Charge-Modified Biopolymer (Demonstration of Charge Grafting onto Soy Protein)

Soy protein was charge-modified to form an anionic soy protein using the DSM extruder described in Example 1.1. In preparing the charge-modified soy protein, Experimental methods followed those in Example 3.1. Table 24 sets forth the ranges for the temperature, screw RPM, and amount of citric acid tested using the twin screw conical extruder.

TABLE 24

Parameter ranges for charge-modified soy protein via twin screw conical extruder

| Temperature Ranges (° C.) | 90-150 |
| --- | --- |
| RPM Ranges (RPM) | 50-200 |
| Citric Acid Ranges (wt % relative to soy protein) | 40-150 |

Figure 5:
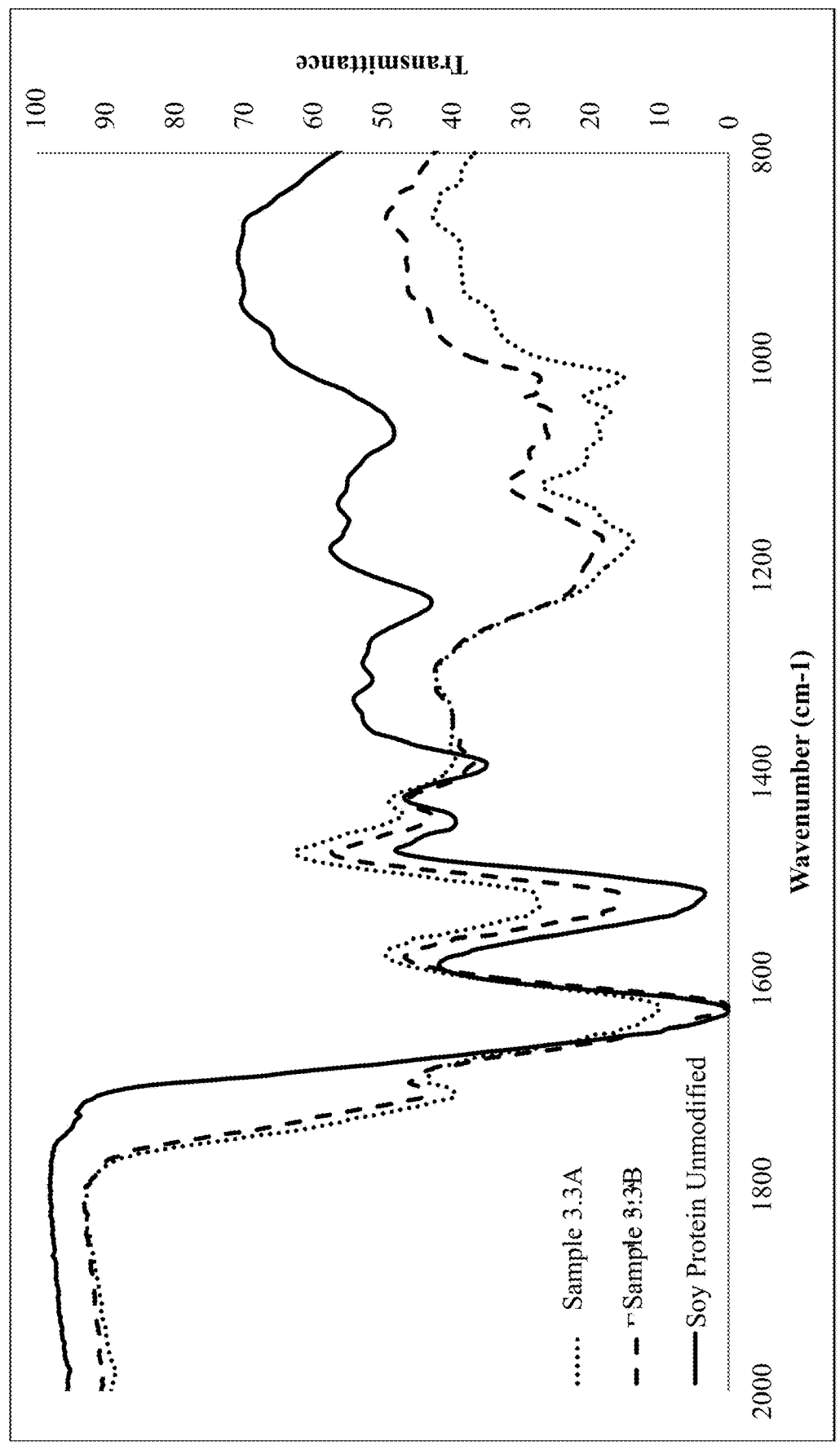
FIG. 5 illustrates FTIR spectra for unmodified soy protein and charge-modified soy protein according to embodiments of the present invention.

Table 25 provides specific parameters tested with test responses described in Table 26. If the sample underwent a post treatment, then the sample was placed in a vacuum oven at 120° C. for 90 mins. Each sample was tested to determine its charge density (meq/g), and absorbance/transmittance via Fourier Transform Infrared Spectroscopy (FTIR) at 1720 cm$^{-1}$. The FTIR spectra for the charge-modified soy protein and for unmodified soy protein is provided in FIG. 5. Charge density values are reported according to the titration method described in Example 1.1. It should be noted that in this example, charge density values of the raw materials are measured and then subtracted from measured values to show a degree of change in charge density above that of the raw biopolymer.

TABLE 25

Process and formulation parameters for preparing charge-modified soy protein

|  | Sample # | |
| --- | --- | --- |
|  | Sample 3.3A | Sample 3.3B |
| Temperature (° C.) | 140 | 140 |
| RPM | 120 | 120 |
| Post Treatment | No | Yes |
| Citric Acid (wt % relative to hemicellulose) | 150 | 150 |
| SHP (wt % relative to soy protein) | 20 | 20 |

TABLE 26

Properties of the charged-modified soy protein

| Sample # | FTIR (% Trans) | Titration (meq/g) |
| --- | --- | --- |
| 3.3A | 68.4 | 1.66 |
| 3.3B | 42.8 | 4.68 |

A charge-modified soy protein was produced via reactive extrusion. FTIR analysis shows % Transmission values significantly lower than that of unmodified soy protein (93%) and titration values significantly greater than that of unmodified pectin (0 meq/g), indicating charge modification of the soy protein. Charge modification was enhanced by thermal post treatment.

Example 4.1: Extruded Crosslinked Biopolymer (Demonstration of Starch Modified with a Range of Crosslinkers)

In addition to charge modifiers, crosslinkers were utilized to form a crosslinked starch using the DSM extruder described in Example 1.1. In preparing the crosslinked starch, experimental methods followed those in Example 1.1. The following parameters are varied: temperature, screw RPM, and the amount of crosslinker. In this example, water was used as the plasticizer at the level of 40 wt % relative to starch. Crosslinkers included: Epichlorohydrin (EPI, >=99% (GC), Item 45340, Sigma-Aldrich, St. Louis, Mo.), Poly(ethylene glycol) diglycidyl ether (PEDGE, Avg. MN 500, Item 475696, Sigma-Aldrich, St. Louis, Mo.), and Poly(propylene glycol) diglycidyl ether (PPDGE, Avg. CA. 640, Item 406740, Sigma-Aldrich, MO, St. Louis) with sodium hydroxide as catalyst. Table 27 sets forth the ranges for the temperature, screw RPM, and amount of crosslinker tested using the twin screw conical extruder. Table 28 provides specific parameters tested with test responses described in Table 29.

TABLE 27

Process and formulation ranges for preparing crosslinked starch

| Temperature (° C.) | 80-110 |
| --- | --- |
| RPM | 50-120 |
| Crosslinker | Epichlorohydrin, PEDGE, and PPDGE |

TABLE 27-continued

Process and formulation ranges for preparing crosslinked starch

| | |
|---|---|
| Crosslinker (wt % relative to starch) | 0.01-0.1 |
| NaOH (wt % relative to starch) | 0.005-0.2 |

TABLE 28

Process and formulation parameters for preparing crosslinked starch

| | Sample # | | |
|---|---|---|---|
| | Sample 4.1A | Sample 4.1B | Sample 4.1C |
| Temperature (° C.) | 90 | 90 | 90 |
| RPM | 120 | 120 | 120 |
| Post Treatment | No | No | No |
| Crosslinker | EPI | PEDGE | PPDGE |
| Crosslinker (wt % relative to starch) | 0.1 | 0.1 | 0.1 |
| NaOH (wt % relative to starch) | 0.2 | 0.2 | 0.2 |
| Plasticizer (40% relative to starch) | Water | Water | Water |

TABLE 29

Properties of crosslinked starch

| Sample # | Solubility (%) | Swelling (g/g) |
|---|---|---|
| Sample 4.1A | 1.6 | 0.35 |
| Sample 4.1B | 2.53 | 2.67 |
| Sample 4.1C | 4.07 | 3.15 |

Here, crosslinked biopolymers were produced via a reactive extrusion process. Reactive extrusion of starch with crosslinkers show: as crosslinker chain length (molecular weight) is increased (EPI<PEDGE<PPDGE), swelling values improve beyond that of uncrosslinked starch (0.4 g/g) and solubility values approach that of uncrosslinked starch (7%).

Example 4.2: Extruded, Crosslinked, Charge-Modified Biopolymer (Demonstration of Cationic Starch Modified with Various Crosslinkers)

Charge-modified starch was utilized to form a crosslinked, charge-modified starch using the DSM extruder described in Example 1.1. In preparing the crosslinked, charge-modified starch, experimental methods followed those in Example 4.1. Aquaflocc 330 AW, manufactured by Aquasol Corp (Rock Hill, S.C.) was used as the cationic starch in this example. Additional commercially-available cationic starches, as well as cationic starches as described in Example 2.2 were also utilized. The following parameters are varied: temperature, screw RPM, amount of crosslinker, and plasticizer. Crosslinkers included: Epichlorohydrin, Poly(ethylene glycol) diglycidyl ether, and Poly(propylene glycol) diglycidyl ether with sodium hydroxide as catalyst. Table 30 sets forth the ranges for the temperature, screw RPM, and amount of crosslinker tested using the twin screw conical extruder. Table 31 provides specific parameters tested with test responses described in Table 32.

TABLE 30

Process and formulation ranges for preparing crosslinked, cationic starch

| | |
|---|---|
| Temperature (° C.) | 80-160 |
| RPM | 10-300 |
| Crosslinker (wt % relative to starch) | 0.0001-10 |
| NaOH (wt % relative to starch) | 0.001-20 |
| Plasticizer (%) | Water, Glycerol (20-50%) |

TABLE 31

Process and formulation parameters for preparing crosslinked, cationic starch

| | Sample # | | |
|---|---|---|---|
| | Sample 4.2A | Sample 4.2B | Sample 4.2C |
| Temperature (° C.) | 90 | 90 | 90 |
| RPM | 120 | 120 | 120 |
| Post Treatment | No | No | No |
| Crosslinker | EPI | PEDGE | PPDGE |
| Crosslinker (wt % relative to starch) | 0.1 | 0.1 | 0.1 |
| NaOH (wt % relative to starch) | 0.2 | 0.2 | 0.2 |
| Plasticizer (% relative to starch) | Water (40%) | Water (40%) | Water (40%) |

TABLE 32

Properties of crosslinked cationic starch

| Sample # | Solubility (%) | Swelling (g/g) |
|---|---|---|
| Sample 4.2A | 12.6 | 1.9 |
| Sample 4.2B | 39.9 | 11.2 |
| Sample 4.2C | 40.3 | 14.7 |

Here, crosslinked, charge-modified biopolymers were created via reactive extrusion. Solubility results show values significantly lower than that of the raw material (84%). Here, decreasing solubility indicates increased a degree of crosslinking. Swelling results may be higher or lower than that of the raw material (4.4 g/g) depending on degree of crosslinking.

Example 5.1: Extruded Crosslinked, Charge-Modified Biopolymer (Demonstration of Crosslinking Multiple Biopolymers Using 2-Step, in Line Method)

To demonstrate crosslinking two charge-modified biopolymers, crosslinked, charge-modified starch citrate chitosan was prepared using a 2-step inline process using the Leistritz, 18 mm extruder as described in Example 1.1. Grafting citric acid onto starch provides an anionic charge, which changes the degree of charge as can be measured using back titration (meq/g). Acetic acid protonates chitosan upon mixing, thereby providing a cationic charge on the chitosan. The charge-modified chitosan is assumed to be partially (i.e., 50% or more) or fully (100%) protonated due to its solubility in water.

Furthermore, the extruder having multiple zones as shown in FIG. 2, allows for implementation of temperature and injection profiles. Extrusion and composition parameters for preparing crosslinked, charge-modified starch citrate chitosan were varied as described in Table 33. Here, powder samples of starch, citric acid, and SHP were fed into the initial injection zone (Step 1), while chitosan (Trading Resources, Cocoa Beach, Fla.), acetic acid (Sigma Aldrich, Item #A6283, St. Louis, Mo.), and plasticizers were simultaneously added in at injection zone 3 (Step 2) as shown in Table 34 below. Reactions zones 1-2 were used for charge modification, while reaction zones 3-8 were used for crosslinking the charge-modified starch to charge-modified chitosan. Temperature profiles for each zone are provided in Table 34 below. Screw profile utilized largely conforms to the medium shear screw as described in FIG. 6B (medium shear screw). After the graft reaction of citric acid onto starch, the temperature was decreased to 100° C. to allow for the injection of protonated chitosan inside the extruder in zone 3 before raising the temperature to 105° C. and 110° C. in zones 4 and 5, respectively, to initiate the crosslinking reaction between the starch carboxylate and the free amine groups on the backbone of chitosan. In some runs, extruded samples in solid form were post-treated by placing the charge-modified, crosslinked polymer in an oven at 120° C. for 90 minutes. The simultaneous injection of two mixtures demonstrated below is defined as a 2-step, inline reaction.

TABLE 33

Parameter ranges for crosslinked starch citrate chitosan via parallel twin screw extruder

| | |
|---|---|
| Temperature Ranges (° C.) | 100-120 (see Table 34) |
| RPM Ranges (RPM) | 140-170 |
| Chitosan Ranges (wt % relative to starch) | 100 |
| Acetic Acid Ranges (wt % relative to chitosan) | 33 |
| Starch Citrate Ranges (wt % relative to chitosan) | 100 |
| Plasticizer Types | Citric Acid |
| Plasticizer Ranges (wt % relative to chitosan) | 90-140 |

TABLE 34

Example of temperature and injection profile for charge-modified starch crosslinked to another biopolymer via parallel twin-screw extruder

| Zone | 1 | 2 | 3 | 4 | 5 | 6 | 7 | 8 |
|---|---|---|---|---|---|---|---|---|
| Temperature (° C.) | 120 | 120 | 100 | 105 | 110 | 110 | 110 | 105 |
| Injection | Starch + Reagents | N/A | N/A | Chitosan + Reagents | N/A | N/A | N/A | N/A | N/A |

Specific examples of process parameters and resulting responses are shown in Tables 35 and 36 below, respectively. The methods for determining the measured responses (e.g., solubility, DI uptake, and extractables) are described in Example 1. For FTIR analysis, bonds of interest for charged-modified starch, crosslinked to chitosan system include the Amide-Carbonyl (R—CO—CNH—R) stretch at ~1650 cm$^{-1}$.

TABLE 35

Process parameters for preparing crosslinked, charge-modified starch citrate chitosan

| | Sample # | | |
|---|---|---|---|
| | Sample 5.1A | Sample 5.1B | Sample 5.1C |
| Temperature (° C.) | 100-120 (multiple zones) | 100-120 (multiple zones) | 100-120 (multiple zones) |
| RPM | 140 | 140 | 170 |
| Post Treatment | Yes | No | Yes |
| Reaction Type | 2-step inline | 2-step inline | 2-step inline |
| Plasticizer Type | Citric Acid | Citric Acid | Citric Acid |
| Plasticizer (wt % relative to chitosan) | 75 | 75 | 75 |
| Starch Citrate (wt % relative to chitosan) | 100 | 100 | 100 |
| Acetic Acid (wt % relative to chitosan) | 33 | 33 | 33 |

TABLE 36

Properties of the crosslinked, charge-modified starch citrate chitosan

| Sample # | Solubility (%) | FTIR (% Trans) | DI Uptake (g/g) | Extractables (%) |
|---|---|---|---|---|
| 5.1A | 4.1 | 67.5 | 2.6 | 19 |
| 5.1B | 2.4 | 65.4 | 9.5 | 69 |
| 5.1C | 4.1 | 68.2 | 1.9 | 19 |

As described in Example 2, charge-modified polymers without crosslinking show increasing solubility with increasing charge density (>5% and up to 100%). Due to the presence of charge-modified starch and charge-modified chitosan, solubility values<5% indicate presence of crosslinking. FTIR analysis confirms presence of the amide-carbonyl stretch where a modified and unmodified chitosan shows transmission values of 26% and modified and unmodified starch shows values of 5%. % Transmission values above 26% indicate presence of charge-modified starch crosslinked to charge-modified chitosan, confirming the ability to form a charge-modified biopolymer cross-linked to another biopolymer in a 2-step, in-line method.

Example 5.2: Extruded Crosslinked, Charge-Modified Biopolymer (Demonstration of Crosslinking Multiple Biopolymers Using 2-Step, 2-Pass Method)

To demonstrate a method where charged-modified biopolymers are produced and subsequently crosslinked to another biopolymer, charged-modified starches as prepared in Example 1.1 were crosslinked with chitosan by mixing powdered starch citrate (i.e., the citric acid-modified starch) with acetic acid, chitosan, and plasticizer so that the mixture was in powdered form. To obtain the powdered charge-modified starch, the charge-modified starch was ground using a blender to sugar/starch consistency where there were no visible chunks/inconsistencies in the powder mixtures. At least one plasticizer selected from: glycerol [Item #0854, Amresco, Solon, Ohio], citric acid, and polyethylene glycol [molecular weights of 400, 800, 20,000, Sigma Aldrich, St. Louis, Mo.] was added to the mixture including starch citrate, acetic acid, chitosan, and plasticizer to induce melt blending during the extrusion process. The resulting powder mixture was added to the extruder described in Example 1.1 in a method resembling the process for preparing charge-modified starch as described in Example 1.1. Extrusion parameters and compositions were modified according to Table 37 below.

TABLE 37

Parameter ranges for crosslinked, charge-modified starch citrate chitosan via twin screw conical extruder

| | |
|---|---|
| Temperature Ranges (° C.) | 90-130 |
| RPM Ranges (RPM) | 60-200 |
| Chitosan Ranges (wt % relative to starch) | 50-150 |
| Acetic Acid Ranges (wt % relative to chitosan) | 5-100 |
| Starch Citrate Ranges (wt % relative to chitosan) | 150-250 |
| Plasticizer Types | Glycerol, Citric Acid, Water |
| Plasticizer Ranges (wt % relative to chitosan) | 120-275 |

Completion of the reaction in two steps is defined here as a "2-step, 2-pass" reaction. Examples of process parameters for crosslinked, charge-modified starch citrate chitosan and measured responses are shown in Tables 38 and 39, respectively below. The charge-modified starch used to prepare the crosslinked, charge-modified starch citrate chitosan had previously been prepared as described in Example 1 according to parameters described in sample 1.1A.

Each sample was analyzed via FTIR to characterize chemical identity, determine its deionized water (DI) uptake, and to measure extractables (inverse of yield) following the methods described in Example 1.

TABLE 38

Process parameters for preparing crosslinked, charge-modified starch citrate chitosan

| | Sample # | |
|---|---|---|
| | Sample 5.2A | Sample 5.2B |
| Extruder | DSM | DSM |
| Temperature (° C.) | 100 | 110 |
| RPM | 120 | 120 |
| Post Treatment | No | No |
| Reaction Type | 2-step, 2-pass | 2-step, 2-pass |
| Plasticizer Type | Citric Acid | Citric Acid |
| Plasticizer (wt % relative to chitosan) | 175 | 175 |
| Starch Citrate (wt % relative to chitosan) | 100 | 250 |
| Acetic Acid (wt % relative to chitosan) | 33 | 33 |

TABLE 39

Properties of the crosslinked starch citrate chitosan

| Sample # | FTIR (% Trans) | DI Uptake (g/g) | Extractables (%) |
|---|---|---|---|
| 5.2A | 59.4 | 2.7 | 73 |
| 5.2B | 62.6 | 1.5 | 61 |

As described in Example 5.1, a citric acid modified starch crosslinked to chitosan shows the amide-carbonyl (R—CO—CNH—R) stretch at ~1650 cm$^{-1}$ when subjected to FTIR analysis. FTIR analysis confirms presence of the amide-carbonyl stretch where a modified and unmodified chitosan shows transmission values of 26% and modified and unmodified starch shows values of 5%. Here, % Transmission values of 59 and 62% (>26%) indicate presence of charge-modified starch crosslinked to charge-modified chitosan and confirming the ability to form a charge-modified biopolymer crosslinked to another biopolymer in a 2-step, 2-pass method.

Example 5.3: Extruded Crosslinked, Charge-Modified Biopolymer (Demonstration of Crosslinking Multiple Biopolymers Using all-in-One Method)

To demonstrate simultaneous charge modification and crosslinking via reactive extrusion, all raw materials (i.e., starch, citric acid, SHP, chitosan, acetic acid, and plasticizer as described in Examples 5.1 and 5.2) were injected simultaneously in powder form to induce charge modification and crosslinking reactions in one injection through multiple extruders (defined here as an "all-in-one" reaction). Here, the mixture of all raw materials was added to the extruder described in Example 1.1 and 1.3 in a method resembling the process for preparing charge-modified starch as described in Example 1.1 and 1.3. Extrusion parameters and compositions were modified according to Table 40 below. Examples of process parameters for preparing crosslinked, charge-modified starch citrate chitosan are shown in Table 41 below with measured responses provided in Table 42. The methods for determining the measured responses are provided in Examples 1 and 2.

TABLE 40

Parameter ranges for crosslinked, charge-modified starch citrate chitosan via twin screw conical extruder and 52 mm, parallel twin screw extruder

| | | |
|---|---|---|
| Extruder | DSM | Wegner TX-52 |
| Temperature Ranges (° C.) | 90-130 | 105-130 |
| RPM Ranges (RPM) | 60-200 | 120-250 |
| Chitosan Ranges (wt % relative to starch) | 50-150 | 50-75 |
| Acetic Acid Ranges (wt % relative to chitosan) | 5-100 | N/A |
| Starch Ranges (wt % relative to chitosan) | 150-250 | 100 |
| Plasticizer Types | Glycerol, Citric Acid, Poly Ethylene Glycol, Water | Citric Acid, Water |
| Plasticizer Ranges (wt % relative to chitosan) | 120-275 | 100-130 |

TABLE 41

Process parameters for preparing crosslinked, charge-modified starch citrate chitosan

| | Sample 5.3A | Sample 5.3B | Sample 5.3C | Sample 5.3D |
|---|---|---|---|---|
| Extruder | DSM | DSM | Wegner TX-52 | Wegner TX-52 |
| Temperature (° C.) | 100 | 133 | 120 | 110 |
| RPM | 120 | 120 | 120 | 200 |
| Post Treatment | No | No | No | No |
| Reaction Type | All-in-one | All-in-one | All-in-one | All-in-one |
| Plasticizer Type | Citric Acid | Glycerol | Citric Acid | Citric Acid |
| Plasticizer (wt % relative to chitosan) | 175 | 175 | 100 | 100 |
| Starch (wt % relative to chitosan) | 150 | 100 | 150 | 150 |
| Citric Acid (wt % relative to starch) | 66 | 66 | N/A | N/A |
| SHP (wt % relative to starch) | 20 | 20 | 20 | 20 |
| Acetic Acid (wt % relative to chitosan) | 33 | 33 | N/A | N/A |

TABLE 42

Properties of the crosslinked, charge-modified starch citrate chitosan

| Sample # | FTIR (% Trans) | DI Uptake (g/g) | Extractables (%) |
|---|---|---|---|
| 5.3A | 58.8 | 4.3 | 58 |
| 5.3B | 66.9 | 4.9 | 54 |
| 5.3C | 67.2 | N/A | 67 |
| 5.3D | 65.3 | N/A | 65 |

As described in Example 5.1 and 5.2, a citric acid modified starch crosslinked to chitosan shows the Amide-Carbonyl (R—CO—CNH—R) stretch at ~1650 cm$^{-1}$ when subjected to FTIR analysis. The presence of carbonyl groups indicates citric acid charge modification on starch, and the presence of the Amide-carbonyl group indicates crosslinking. FTIR analysis confirms presence of the Amide-carbonyl stretch where a modified and unmodified chitosan shows transmission values of 26% and modified and unmodified starch shows values of 5%. Here, % Transmission values of >26% indicate simultaneous charge modification and cross-linking of charge-modified starch crosslinked to chitosan to form a charge-modified biopolymer crosslinked to another biopolymer in an all-in-one method.

Example 6: Example of Modified Biopolymer for IEX Application (Demonstration of Salt/Heavy Metal Uptake)

To demonstrate ion removal capabilities of a charge-modified, crosslinked biopolymer, citric acid-modified starch crosslinked to chitosan were prepared according to Examples 5.1, 5.2, and 5.3. Samples were tested for their salt uptake capacity measured by conductivity and ash content post exposure to a saline solution.

Ash content testing is a measure of residual inorganic material in a sample upon exposure to high temperatures. 0.3 g of samples was exposed to a 10% saline (NaCl) solution for 5 minutes, then squeezed by hand to remove absorbed liquids. Samples were then transferred to clean, dry, glass vials whose weights were previously recorded. Samples were then exposed to high temperatures in a muffle furnace (Vulcan, Model 3-550), for 4 hours at 575° C. following TAPPI Standard: T211 om-02—"Ash in wood, pulp, paper and paperboard, combustion at 525° C." (2002), which is incorporated herein by reference in its entirety. To determine the ash content, the vial weight was subtracted from the final recorded weight of vial and ash. Final ash weight was assumed to be residual captured salts where the final ash weight is divided by the initial sample weight to normalize data to a g NaCl/g sample (g/g) format.

Conductivity is a measure of ionic mobility in a given solution. Reductions in conductivity are attributed to captured ions, changes in system energy (i.e., temperature, pressure, etc.), and/or potential of dissolved ions (i.e., pH changes in presence of acids/bases). Samples (0.3 g) were exposed to 25 mL of 10% NaCl solution where initial conductivity (Metler-Toledo conductivity instrument [model #51302530]) was measured to be 142 mS/cm with a standard deviation of 3.7. Final conductivity measurements were assumed to be attributed to ion capture and was therefore used to calculate a percent difference in conductivity (captured salt). The uptake of salt was correlated to the resulting decrease in conductivity by the following formula:

Salt Uptake=(volume in mL*salinity*% Δ)/sample weight, where % Δ is the % change in conductivity. The % change in conductivity is attributed to a reduction in mass of NaCl in solution and is normalized to samples weight. The resulting measurement parameter yields salt uptake as g NaCl/g sample.

TABLE 43

Salt removal properties of a charge-modified and crosslinked biopolymer system

| Sample # | Salt Uptake - Conductivity (g/g) | Salt Uptake - Ash Content (g/g) |
|---|---|---|
| 5.1A | 0.24 | 0.98 |
| 5.1B | 0.22 | 1.1 |
| 5.1C | 0.16 | 0.69 |
| 5.2A | 0.13 | N/A |
| 5.2B | 0.13 | N/A |
| 5.3A | N/A | 0.1 |
| 5.3B | 0.25 | 0.74 |
| 5.3C | 0.2 | N/A |
| 5.4D | 0.24 | N/A |

Here, salt uptake results of a crosslinked biopolymer (crosslinked cationic starch as prepared via the method found in Example 4.2) as measured by conductivity show values of 0 g/g. The presence of amphoteric charge (including both cationic and anionic charge simultaneously) is expected to improve the polymer's interaction with free ions in solution and is shown in Table 43. Data demonstrated the ability of charge-modified and crosslinked biopolymers to remove ions from solution at a greater rate than a crosslinked biopolymer. Salt uptake is further demonstrated through ash content measurements as shown in Table 43 above.

Example 7: Example of Modified Biopolymer for SAP Application (Demonstration of Charge-Modified Starch (Cationic) Crosslinked to Form Superabsorbent A superabsorbent polymer was prepared using a commercially available charged cationic starch (AquaFlocc 330AW) and a catalyst on the P11 extruder described in Example 1.1. The extruder having multiple zones similar to that shown in FIG. 2, allows for implementation of temperature and injection profiles. Screw profile utilized is described in FIG. 6B (medium shear screw). Extrusion and composition parameters for preparing a material for superabsorbent material were varied as described in Table 44. In preparing the superabsorbent polymer, powder cationic starch (Aquafloc 330AW) and sodium hydroxide were fed into the initial injection zone via volumetric powder feeder (Volumetric MiniTwin Feeder for Process 11, Typ 567-7660, Thermo Electron/Thermo Fisher Scientific, Germany), while plasticizer (glycerol) was simultaneously added in at injection zone 2 via liquid injector and peristaltic pump (Masterflex P/S Peristaltic Pump, Model No 1300-3600-0004, Thermo Fisher Scientific, USA) with corresponding peristaltic pump head (Masterflex P/S Easy Load II, Model No 955-0000, Thermo Fisher Scientific, USA). In some runs, extruded samples in solid form were post-treated by placing the modified cationic polymer in an oven at 120° C. for 90 minutes. The simultaneous injection of two mixtures demonstrated below is defined as a 2-step, inline reaction.

In preparing the absorbent polymers, the following parameters were varied: temperature, screw RPM, plasticizer, plasticizer concentration, and amount of catalyst. Table 44 sets forth the ranges for the temperature, screw RPM, and amount of catalyst tested using the 11 mm, parallel twin screw extruder.

Samples were tested as absorbents using the EDANA/INDA method WSP 240.2.R3: Free swell capacity in saline by gravimetric determination in order to measure the fluid uptake of samples (2012), which is incorporated herein by reference in its entirety. For the gravimetric method, 0.2 g of sample was sealed in a 2"×2" teabag. The teabag/sample packet was submerged in a solution for 1 hr, then hanged to dry for 10 mins. Solutions were prepared according to an industrially relevant application (0.9% NaCl). Weight measurements were recorded pre- and-post submerging and normalized for a teabag control sample undergoing the same conditions. The calculation was as follows:

$$FSC = \frac{W_w - W_b - W_i}{W_i}$$

where $W_w$ is the wet weight of the teabag/sample, $W_b$ is the wet weight of the teabag alone, and $W_i$ is the initial weight of the teabag/sample.

TABLE 44

| Parameter ranges absorbent polymers via twin screw conical extruder | |
|---|---|
| Temperature Ranges (° C.) | 80-160 |
| RPM Ranges (RPM) | 50-200 |
| Plasticizer | Water, Glycerol, PEG |
| Plasticizer (wt % relative to cat. starch) | 20-60% |
| NaOH (wt % relative to cat. starch) | 0-30% |

Table 45 provides specific parameters tested with specific temperature profiles shown in Table 46 and test responses described in Table 47. Each sample was tested to determine its swelling capacity according to the method described above, and solubility according to the method in example 2. Temp Profile 7 in Table 45 is equal to the temperatures listed in Table 46

TABLE 45

Process and formulation parameters for absorbent polymers

| | Sample # | |
|---|---|---|
| | Sample 7A | Sample 7B |
| Temperature (° C.) | Temp Profile 7 | Temp Profile 7 |
| RPM | 150 | 80 |
| Post Treatment | Yes | Yes |
| Plasticizer (wt % relative to cat. starch) | Glycerol (25%) | Glycerol (25%) |
| NaOH (wt % relative to cat. starch) | 7.5% | 7.5% |

TABLE 46

Temperature and injection profiles for samples 7A and 7B: charge-modified starch via 11 mm, parallel twin-screw extruder

| Sample # | Zone | 1 | 2 | 3 | 4 | 5 | 6 | 7 | 8 | Die |
|---|---|---|---|---|---|---|---|---|---|---|
| | Temp Profile 7 (° C.) | Unheated | 70 | 75 | 80 | 95 | 110 | 100 | 100 | 100 |
| | Injection | Cat. Starch + NaOH | Glycerol | N/A | N/A | N/A | N/A | N/A | N/A | N/A |
| 7A | Feed Rate (RPM) | 50 | 5.9 | N/A | N/A | N/A | N/A | N/A | N/A | N/A |
| 7B | Feed Rate (RPM) | 25 | 2.4 | N/A | N/A | N/A | N/A | N/A | N/A | N/A |

TABLE 47

Properties of the absorbent polymers

| Sample # | Free Swell Capacity (g/g) | Solubility (g/g) |
|---|---|---|
| 7A | 31.6 | 4.5 |
| 7B | 28.8 | 2.0 |

As shown by results in Table 47, reactive extrusion is used to make a biopolymer material that is useful for absorbing liquids in industrially relevant applications.

Example 8: Example of Modified Biopolymer for Biosorbent Application

Additionally, samples as described in Example 7 were tested as absorbents for other fluids using a modified the EDANA/INDA method WSP 240.2.R3: free swell capacity in saline by gravimetric determination in order to measure the fluid uptake of samples. Here, alternative solutions are used as shown in Table 48, in place of the specified 0.9% NaCl (saline). Instant Ocean Sea Salt was used as a sea water stimulant. Canola oil, conventional motor oil, and synthetic motor oil were used as oil references. Gasoline and diesel fuel were used as fuel references, and whole bovine blood was used as a blood reference. The results demonstrated an improved performance for crosslinked, charge-modified biopolymers of the present invention relative to conventional superabsorbent materials: Sodium Polyacrylate (NaPoly, Item 432784, Sigma-Aldrich, St. Louis, Mo.) in Table 48 below.

TABLE 48

Biosorbent properties of a crosslinked, charge-modified biopolymer of the present invention ("Modified Biopolymer") relative to commercially available superabsorbent polymers (NaPoly)

| Solution | Sample | Uptake (g/g) |
|---|---|---|
| Instant Ocean (Sea Water) | Modified Biopolymer | 29 |
| | Na Poly | 19 |
| Canola Oil | Modified Biopolymer | 18 |
| | Na Poly | 2.2 |
| Motor Oil (Conventional) | Modified Biopolymer | 5.3 |
| | Na Poly | 1.7 |
| Motor Oil (Synthetic) | Modified Biopolymer | 9.2 |
| | Na Poly | 2.3 |
| Gasoline | Modified Biopolymer | 3.9 |
| | Na Poly | 0.8 |
| Diesel | Modified Biopolymer | 4.7 |
| | Na Poly | 3.4 |
| Blood | Modified Biopolymer | 16.6 |
| | Na Poly | 1.48 |

As shown by results in Table 48, reactive extrusion is used to make a biopolymer material that is useful for absorbing liquids in a range of industrially relevant applications.

Example 9: Example of Modified Biopolymer Showing Comparative Homogeneity (Homogeneity Analysis)

A JEOL JSM-6010LA scanning electron microscopy (SEM) with a solid state EDS detector was used to characterize and compare samples. Samples were adhered to a mount using double sided carbon tape and analyzed at 20 kV. Micrographs were collected along with corresponding EDS scans of the target area.

Indications of homogeneity were derived from the comparison of commercially available cationic starch to an extruded cationic starch of the present invention (Example 2.2C). AquaFlocc 330AW manufactured by Aquasol Corp (Rock Hill, S.C.) represented the commercially available starch. It is believed that the commercially available cationic starch is modified in a dry process, which maintains starch in granular form and allows only for surface modification of the starch. In contrast, the extrusion process is believed to completely destroy the granular structure of the biopolymer (e.g., starch).

As can be seen in FIGS. 7A and 7B, which are SEM images of commercially available starch, the commercially available starch retains the starch's characteristic granular structure. In contrast, as can be seen in FIGS. 7D and 7E, which are SEM images of extruded cationic starch prepared according to methods of the present invention, starches extruded according to embodiments of the present invention exhibit complete destruction of the granular structure and morphology arises only from topology in sample preparation. This can be seen by comparing FIGS. 7A and 7B with FIGS. 7D and 7E.

Furthermore, when exposed to water and dried, the commercially available starches showed the presence of insoluble materials. These insoluble materials indicate uncharged or lowly charged regions, which are a product of inhomogeneous processing. These results were confirmed via Energy-Dispersive X-ray Spectroscopy (EDS of EDXS), which was used to map the elemental composition of the SEM image for the commercially available starch (FIG. 7C) and the extruded cationic starch prepared according to methods of the present invention (FIG. 7F). As can be seen in FIG. 7C, a clear/defined dark region is present where the discrete particles are imaged. This indicates that these particles are different in composition (lacking chlorine) compared to the surrounding region. In contrast, as can be seen in FIG. 7F, EDS scans of the extruded starch show a gradual change in contrast towards the bottom right of the image. This change correlates to a sloping region on the SEM image towards the bottom right. However, the top left of the image in FIG. 7F also shows a sloping region in the SEM image, with little change in the EDS map. Thus, it can be concluded that any contrast here is from a shadowing effect, rather than a compositional effect and the sample is therefore homogeneous.

Example 10: Interior Crosslinked Modified Starch Prepared with Modified Carboxymethyl Starch Produced Via Reactive Extrusion A modified starch was produced via reactive extrusion. The extrudate was solubilized in water and adjusted with a crosslinking agent. The isolated modified starch was then dried to remove excess water. Subsequently, the isolated modified starch was thermally treated. Crosslinking parameters are displayed in Table 49 while crosslinking outputs are displayed in Table 50.

Notably, the isolated crosslinked modified starch particles are biocompostable according to ASTM D5338 guidelines. No alcohol was used as a reagent during the charge modification step of the extrusion process.

This formulation is one formulation which does not include surface crosslinking or any meaningful amount of surface crosslinking, and is referred to as a formulation for modified biopolymer 1 throughout the present specification. The material was milled and screened to ensure the particle size met distribution guidelines (between about 150 microns and about 850 microns).

TABLE 49

Interior Crosslinking Parameters
Parameters

| Crosslinker | Crosslinker 1 |
|---|---|
| Crosslinker Concentration Relative to Modified Starch | 0.3 wt. % |

Example 11: Surface Crosslinked & Interior Crosslinked Modified Starch Prepared Using Preferred Crosslinkers The interior crosslinked modified starch was prepared in the manner described in Example 10. In separate procedures, solutions containing crosslinkers were added to the surface of interior crosslinked modified starch. Once the material was coated, it was thermally treated. The dried material was screened to ensure the particle size meets distribution guidelines.

The resulting surface-crosslinked modified starch properties are detailed in Table 50. According to ASTM D6866-18 Biobased content testing, the surface crosslinked charge modified starch particles produced have at least 75% biobased carbon content as a percent of total organic carbon. Each of the surface crosslinked modified starches notably has a CRC of at least about 14 g/g, at least about 15 g/g, between about 14 g/g and about 19 g/g, or between about 15 g/g and about 19 g/g. Each of the surface crosslinked modified starches notably has an AUL at 0.7 psi of at least about 8 g/g, at least about 9 g/g, between about 8 g/g and about 12 g/g, between about 8 g/g and about 11 g/g, between about 9 g/g and about 12 g/g, or between about 9 g/g and about 11 g/g.

Notably, the modified biopolymers which utilize these crosslinkers are biocompostable, i.e. the modified biopolymers degrade by at least 90% relative to an analytical grade cellulose control in less than 180 days according to the modified ASTM D5338 described above. The modified biopolymers also have at least 80% biobased carbon content as a percent of total organic carbon according to the ASTM D6866 Carbon 14 Test. The modified biopolymers are biodegradable.

Advantageously, the modified biopolymers are particularly suitable for hygiene applications as they exhibit no cytotoxicity and are not dermal irritants. Cytotoxicity of the modified biopolymers was tested according to ISO 10993-5, using the fully swollen hydrogel form in Minimum Essential Medium (MEM) solution in direct contact with cultures of mouse fibroblast L929 cells for 48 hours. The viability of the exposed cells was assessed directly surrounding the test article, with no biological reactivity of the modified biopolymers with exposed cells. The modified biopolymers are considered to have no cytotoxic effect (Grade 0). Cytotoxicity of the modified biopolymers was tested according to ISO 10993-5, 2009, Biological Evaluation of Medical Devices—Part 5: Tests for In Vitro Cytotoxicity, using extractions obtained of the swollen hydrogel form exposed to cultures of mouse fibroblast L929 cells for 48 hours. The viability of the cells after exposure was assessed using standard MTT assay. The extracts of the modified biopolymers were found to have no biological reactivity with exposed cells, and the modified biopolymers are considered to have no cytotoxic effect (Grade 0). Dermal irritation of the modified biopolymers was tested according to OECD 439, Organization for Economic Cooperation and Development (OECD). Guidelines for the Testing of Chemicals, "In Vitro Skin Irritation: Reconstructed Human Epidermis Test Method", adopted July 2013, using extractions obtained from the swollen hydrogel form exposed to in vitro skin tissue model EpiDerm™. The viability of the cells after exposure was assessed using standard MTT assay. The viability of the cells exposed to the modified biopolymers exceeded 100% and the modified biopolymers are considered non-irritating. This testing was conducted by Toxikon Corporation, Bedford Mass., in compliance with current U.S. Food and Drug Administration 21 CFR, Part 58 Good Laboratory Practices for Nonclinical Laboratory Studies. As chemicals such as epichlorohydrin are known carcinogens in animals, and are reasonably anticipated to be carcinogens in humans, these chemicals are preferably not used as crosslinkers in hygiene applications due to concerns about cytotoxicity and/or dermal irritation.

Additionally, the primary irritation potential of the modified biopolymers was determined using a 48 hour patch test. The modified biopolymers were added in powder form to saline solution in the ratio of 1.0 g of modified biopolymer per 34 g of saline solution or 3.0 g of modified biopolymer per 100 g of saline solution. The solution was mixed well and allowed to rest for at least 10 minutes, but not more than 24 hours, to form a gel-like test material for testing. Approximately 0.2 g of the test material was applied to a 0.75 inch by 0.75 inch absorbent pad portion of an adhesive dressing, which was secured to an appropriate treatment site to form an occlusive patch. The test material remained in contact with the skin for a total of 2 days, and the site was evaluated for gross changes. Absence of any visible skin change was assigned a zero value. There was no visible skin reaction in any of 100 subjects of both male and female genders whose ages ranged from 18 to 79. There were no adverse events, no amendments, and no deviations. Accordingly, the test material indicated no potential for dermal irritation.

These formulations utilize both internal crosslinking and surface crosslinking, and are referred to as formulations for modified biopolymer 2 throughout the present specification.

TABLE 50

| Sample | FSC (g/g) (Saline) | CRC (g/g) (Saline) | AUL (g/g) at 0.7 psi (Saline) |
|---|---|---|---|
| Sample #1 | 40 | 32 | 5.5 |
| Sample #2 | 32 | 19 | 9.6 |
| Sample #3 | 31 | 17 | 11 |
| Sample #4 | 30 | 15 | 11 |
| Sample #5 | 31 | 17 | 10.3 |
| Sample #6 | 34 | 19 | 11 |
| Sample #7 | 30 | 16 | 11 |
| Sample #8 | 33 | 18 | 10 |
| Sample #9 | 31 | 17 | 12 |

Example 12: Surface Crosslinked & Interior Crosslinked Modified Starch Prepared Using Alternative Crosslinkers The interior crosslinked modified starch was prepared in the manner described in Example 10. In separate procedures, solutions of the crosslinkers listed in Table 51 below were added to the surface of interior crosslinked modified starch in order to obtain the coatings in the percentages listed in Table 51 below. Once the material was coated, it was thermally treated. The dried material was screened to ensure the particle size meets distribution guidelines.

The resulting surface-crosslinked modified starch properties are detailed in Table 51. These formulations utilize both internal crosslinking and surface crosslinking, and are referred to as formulations for modified biopolymer 2 throughout the present specification. Advantageously, these modified biopolymers have at least 75% biobased carbon content as a percent of total organic carbon.

TABLE 51

| 1st Surface Crosslinker | 2nd Surface Crosslinker | FSC (g/g) (Saline) | CRC (g/g) (Saline) | AUL at 0.7 psi (g/g) (Saline) |
|---|---|---|---|---|
| First crosslinker | Second crosslinker | 34 | 18 | 10 |
| First crosslinker | Second crosslinker | 32 | 15 | 10 |
| First crosslinker | Second crosslinker | 26 | 12 | 12 |
| First crosslinker | NONE | 32 | 18 | 6 |
| First crosslinker | NONE | 35 | 20 | 7 |
| First crosslinker | NONE | 38 | 26 | 7 |
| First crosslinker | NONE | 36 | 24 | 6 |
| First crosslinker | Second crosslinker | 32 | 17 | 10 |
| First crosslinker | Second crosslinker | 30 | 14 | 10 |
| First crosslinker | NONE | 33 | 17 | 8 |
| First crosslinker | NONE | 35 | 19 | 8 |
| First crosslinker | Second crosslinker | 33 | 20 | 7 |
| First crosslinker | Second crosslinker | 34 | 19 | 6 |
| First crosslinker | Second crosslinker | 34 | 20 | 7 |
| First crosslinker | Second crosslinker | 33 | 17 | 10 |
| First crosslinker | Second crosslinker | 35 | 16 | 11 |
| First crosslinker | Second crosslinker | 32 | 18 | 10 |
| First crosslinker | Second crosslinker | 28 | 16 | 10 |
| First crosslinker | Second crosslinker | 32 | 16 | 10 |
| First crosslinker | Second crosslinker | 30 | 15 | 11 |
| First crosslinker | NONE | 35 | 19 | 7 |
| First crosslinker | NONE | 32 | 17 | 6 |
| First crosslinker | NONE | 34 | 17 | 5 |
| First crosslinker | NONE | 41 | 35 | 5 |
| First crosslinker | Second crosslinker | 31 | 16 | 13 |
| First crosslinker | Second crosslinker | 31 | 17 | 13 |
| First crosslinker | Second crosslinker | 31 | 16 | 11 |
| First crosslinker | Second crosslinker | 30 | 15 | 13 |
| First crosslinker | Second crosslinker | 28 | 14 | 15 |
| First crosslinker | Second crosslinker | 29 | 14 | 12 |
| First crosslinker | NONE | 38 | 24 | 7 |
| First crosslinker | NONE | 35 | 22 | 6 |
| First crosslinker | NONE | 35 | 21 | 7 |
| First crosslinker | Second crosslinker | 34 | 18 | 8 |
| First crosslinker | Second crosslinker | 36 | 19 | 8 |
| First crosslinker | NONE | 37 | 24 | 6 |
| First crosslinker | NONE | 35 | 16 | 11 |
| First crosslinker | NONE | 29 | 14 | 14 |
| First crosslinker | NONE | 30 | 15 | 13 |
| First crosslinker | NONE | 36 | 20 | 9 |
| First crosslinker | NONE | 29 | 13 | 13 |
| First crosslinker | Second crosslinker | 31 | 17 | 13 |
| First crosslinker | Second crosslinker | N/A | 15 | 12 |
| First crosslinker | Second crosslinker | 30 | 15 | 12 |
| First crosslinker | Second crosslinker | N/A | 15 | 12 |
| First crosslinker | NONE | 33 | 19 | 11 |
| First crosslinker | NONE | 34 | 18 | 9 |
| First crosslinker | NONE | 30 | 16 | 7 |
| First crosslinker | NONE | 29 | 16 | 8 |
| First crosslinker | NONE | 31 | 16 | 7 |
| First crosslinker | NONE | 31 | 15 | 9 |

Example 13: Surface Crosslinked & Interior Crosslinked Modified Starch Prepared Using Other Alternative Crosslinkers The interior crosslinked modified starch was prepared in the manner described in Example 10. In separate procedures, crosslinkers were added to the surface of interior crosslinked modified starch. Once the material was coated, it was thermally treated. The dried material was screened to ensure the particle size meets distribution guidelines.

The resulting surface-crosslinked modified starch properties are detailed in Table 52. Properties of the surface-crosslinked modified starch were tested in saline and defibrinated sheep's blood according to a modified FSC ran with defibrinated sheep's blood and a modified CRC ran with defibrinated sheep's blood.

These formulations utilize both internal crosslinking and surface crosslinking, and are referred to as formulations for modified biopolymer 2 throughout the present specification. Advantageously, these modified biopolymers have at least 75% biobased carbon content as a percent of total organic carbon.

TABLE 52

| Bulk crosslinker | Surface crosslinker | Avg FSC (g/g) (Saline) | Avg CRC (g/g) (Saline) | Avg FSC (g/g) (Defibrinated Sheep's Blood) | Avg CRC (g/g) (Defibrinated Sheep's Blood) |
|---|---|---|---|---|---|
| First crosslinker | Second crosslinker | 32 | 19 | 23 | 16 |
| First crosslinker | Second crosslinker | 36 | 30 | 13 | 12 |
| First crosslinker | Second crosslinker | 35 | 18 | 18 | 14 |
| First crosslinker | Second crosslinker | 40 | 30 | 6 | 5 |

Example 14: Surface Crosslinked & Interior Crosslinked Modified Starch Prepared Using Alternate Crosslinkers The interior crosslinked modified starch was prepared in the manner described in Example 10. In separate procedures, a first and second crosslinker were added to the surface of the interior crosslinked modified starch. Once the material was coated, it was thermally treated. The dried material was screened to ensure the particle size meets distribution guidelines.

The resulting surface-crosslinked modified starch properties are detailed in Table 53.

These formulations utilize both internal crosslinking and surface crosslinking, and are referred to as formulations for modified biopolymer 2 throughout the present specification.

TABLE 53

| 1st Surface Crosslinker relative wt. % | 2nd Surface Crosslinker relative wt. % | FSC (g/g) (Saline) | CRC (g/g) (Saline) | AUL at 0.7 psi (g/g) (Saline) |
|---|---|---|---|---|
| First crosslinker | Second crosslinker | 34 | 20 | 7 |
| First crosslinker | Second crosslinker | 32 | 16 | 9 |
| First crosslinker | Second crosslinker | 32 | 16 | 13 |
| First crosslinker | Second crosslinker | 37 | 21 | 7 |
| First crosslinker | Second crosslinker | 40 | 26 | 6 |
| First crosslinker | Second crosslinker | 31 | 15 | 3 |

TABLE 53-continued

| 1st Surface Crosslinker relative wt. % | 2nd Surface Crosslinker relative wt. % | FSC (g/g) (Saline) | CRC (g/g) (Saline) | AUL at 0.7 psi (g/g) (Saline) |
|---|---|---|---|---|
| First crosslinker | Second crosslinker | 25 | 12 | 1 |
| First crosslinker | NONE | 34 | 17 | 6 |
| First crosslinker | NONE | 33 | 16 | 4 |
| First crosslinker | NONE | 34 | 20 | 6 |
| First crosslinker | NONE | 33 | 16 | 7 |
| Crosslinker A | Crosslinker B | 32 | 18 | 14 |

A range of pre-thermal treatment mixing times were tested. After mixing, the now coated interior crosslinked modified starch was thermally treated with a range of curing times. The dried material was screened to ensure the particle size meets distribution guidelines.

The resulting surface-crosslinked modified starch properties are detailed in Table 54. These formulations utilize both internal crosslinking and surface crosslinking, and are referred to as formulations for modified biopolymer 2 throughout the present specification.

TABLE 54

| 1st Surface Crosslinker | 2nd Surface Crosslinker | Mixing Time (Minutes) | Cure Time (Minutes) | FSC (g/g) (Saline) | CRC (g/g) (Saline) | AUL at 0.7 psi (g/g) (Saline) |
|---|---|---|---|---|---|---|
| Crosslinker A | Crosslinker B | Mixing Time A | Cure Time A | 36 | 23.6 | 8.5 |
| Crosslinker A | Crosslinker B | Mixing Time B | Cure Time A | 36 | 23.5 | 8.6 |
| Crosslinker A | Crosslinker B | Mixing Time C | Cure Time A | 37 | 24.0 | 8.7 |
| Crosslinker A | Crosslinker B | Mixing Time D | Cure Time A | 35 | 23.1 | 9.0 |
| Crosslinker A | Crosslinker B | Mixing Time E | Cure Time A | 36 | 23.3 | 8.0 |
| Crosslinker A | Crosslinker B | Mixing Time F | Cure Time A | 37 | 24.0 | 7.9 |
| Crosslinker A | Crosslinker B | Mixing Time G | Cure Time A | 36 | 22.9 | 10.4 |
| Crosslinker A | Crosslinker B | Mixing Time H | Cure Time A | 34 | 22.5 | 11.4 |
| Crosslinker A | Crosslinker B | Mixing Time I | Cure Time A | 35 | 23 | 9.7 |
| Crosslinker A | Crosslinker B | Mixing Time J | Cure Time A | 35 | 23.9 | 9.5 |
| Crosslinker A | Crosslinker B | Mixing Time I | Cure Time B | 35 | 21.8 | 11.5 |
| Crosslinker A | Crosslinker B | Mixing Time I | Cure Time C | 32 | 18.1 | 14.4 |

Example 15: Surface Crosslinked & Interior Crosslinked Modified Potato Starch Prepared Using Crosslinkers Potato starch having an amylose content of approximately 80% and an amylopectin content of approximate 20% was extruded. The extrudate was solubilized in water and amounts of a first crosslinker and a second crosslinker were added in varying amounts. The SAP was then separated from solution and cured.

The resulting performance of each of the modified biopolymers is presented in Table 55 below. These formulations utilize internal crosslinking only, and are referred to as formulations for modified biopolymer 1 throughout the present specification.

TABLE 55

| Crosslinker Mix | FSC (g/g) (Saline) | CRC (g/g) (Saline) | AUL at 0.7 psi (g/g) (Saline) |
|---|---|---|---|
| Crosslinker Mix A | 25 | 16 | 6 |
| Crosslinker Mix B | 24 | 15 | 7 |
| Crosslinker Mix C | 21 | 13 | 10 |
| Crosslinker Mix D | 30 | 20 | 6 |
| Crosslinker Mix E | 30 | 25 | 5 |
| Crosslinker Mix F | 33 | 25 | 6 |
| Crosslinker Mix G | 28 | 20 | 5 |
| Crosslinker Mix H | 27 | 19 | 7 |
| Crosslinker Mix I | 27 | 17 | 8 |
| Crosslinker Mix J | 27 | 17 | 7 |

Example 16: Surface Crosslinked & Interior Crosslinked Charge Modified Starch Blended with Commercially Available Non-Biobased SAP A range of blends between the surface crosslinked and interior crosslinked charge modified starch synthesized using Crosslinker A or Crosslinker B, and a commercially available SAP, were prepared and absorbance properties measured. Additionally, a range of blends between the charge modified starch synthesized just using Crosslinker C and a commercially available SAP, were tested. The results of these tests are detailed below in Table 56.

TABLE 56

| SAP Blend | Blends with SAP A FSC (g/g) | Blends with SAP A CRC (g/g) | Blends with SAP B FSC (g/g) | Blends with SAP B CRC (g/g) | Percent SAP A w/w or SAP B N/A | Percent Commercial non-biobased SAP N/A | CRC Delta N/A |
|---|---|---|---|---|---|---|---|
| 100% SAP A or SAP B w/w | 30.9 | 18.2 | 36.3 | 23.3 | 100% | 0% | 28% |
| 100% Commercially Available Non-Biobased SAP w/w | 57.7 | 33.9 | 57.7 | 33.9 | 0% | 100% | N/A |
| 60% SAP A or SAP SAP B w/w | 41.6 | 24.5 | 44.8 | 27.6 | 60% | 40% | 13% |
| 50% SAP A or SAP B w/w | 44.3 | 26.0 | 47.0 | 28.6 | 50% | 50% | 10% |
| 45% SAP A or SAP B w/w | 45.7 | 26.8 | 48.1 | 29.1 | 45% | 55% | 9% |

TABLE 56-continued

| SAP Blend | Blends with SAP A FSC (g/g) | Blends with SAP A CRC (g/g) | Blends with SAP B FSC (g/g) | Blends with SAP B CRC (g/g) | Percent SAP A w/w or SAP B N/A | Percent Commercial non-biobased SAP N/A | CRC Delta N/A |
|---|---|---|---|---|---|---|---|
| 40% SAP A or SAP B w/w | 47.0 | 27.6 | 49.1 | 29.7 | 40% | 60% | 7% |
| 35% SAP A or SAP B w/w | 48.3 | 28.4 | 50.2 | 30.2 | 35% | 65% | 6% |
| 25% SAP A or SAP B w/w | 51.0 | 30.0 | 52.4 | 31.3 | 25% | 75% | 4% |
| 20% SAP A or SAP B w/w | 52.4 | 30.8 | 53.4 | 31.8 | 20% | 80% | 3% |

A further range of blends of SAP A and SAP C blended with a commercial non-biobased SAP were tested. SAP A has a FSC of 30.9 g/g, a CRC of 18.4 g/g and an AUL of 8.4 g/g, SAP C has a FSC of 22.2 g/g, a CRC of 15.6 g/g and an AUL of 7.6 g/g, and the commercial non-biobased SAP has a FSC of 57.7 g/g, a CRC of 33.9 g/g and an AUL of 22.2 g/g. The results of the tests of these blends are detailed below in Table 57.

TABLE 57

| SAP Blend | SAP A FSC (g/g) | SAP A CRC (g/g) | SAP C FSC (g/g) | SAP C CRC (g/g) | Percent SAP A or SAP C w/w N/A | Percent Comm SAP N/A | CRC Delta N/A |
|---|---|---|---|---|---|---|---|
| 100% SAP A or SAP C w/w | 30.9 | 18.2 | 22.2 | 15.6 | 100% | 0% | -14% |
| 100% commercial non-biobased SAP | 57.7 | 33.9 | 57.7 | 33.9 | 0% | 100% | |
| 60% SAP A or SAP B w/w | 41.6 | 24.5 | 36.4 | 22.9 | 60% | 40% | -6% |
| 50% SAP A or SAP B w/w | 44.3 | 26.0 | 40.0 | 24.7 | 50% | 50% | -5% |
| 45% SAP A or SAP B w/w | 45.7 | 26.8 | 41.7 | 25.7 | 45% | 55% | -4% |
| 40% SAP A or SAP B w/w | 47.0 | 27.6 | 43.5 | 26.6 | 40% | 60% | -4% |
| 35% SAP A or SAP B w/w | 48.3 | 28.4 | 45.3 | 27.5 | 35% | 65% | -3% |
| 30% SAP A or SAP B w/w | 49.7 | 29.2 | 47.1 | 28.4 | 30% | 70% | -3% |
| 25% SAP A or SAP B w/w | 51.0 | 30.0 | 48.8 | 29.3 | 25% | 75% | -2% |
| 20% SAP A or SAP B w/w | 52.4 | 30.8 | 50.6 | 30.2 | 20% | 80% | -2% |

Example 17: Surface Crosslinked & Interior Crosslinked Charge Modified Starch Prepared Using Crosslinker A and Crosslinker B The surface crosslinked and interior crosslinked charge modified starch synthesized from Crosslinker A and Crosslinker B, was also taken and mixed with a commercially available non-biobased SAP in ratios of 40:60, 45:55, and 50:50 by weight. An additional surface crosslinked and interior crosslinked charge modified starch superabsorbent was also made.

The resulting performance of each SAP blend is presented in Table 58 below.

TABLE 58

| Superabsorbent Used | FSC of Pure SA, (g/g) | CRC of Pure SA (g/g) |
|---|---|---|
| 35/65 SAP A w/w/ commercial non-biobased SAP | 48.3 | 28.4 |
| 40/60 SAP B w/w/ commercial non-biobased SAP | 49.1 | 29.7 |
| 45/55 SAP B w/w/ commercial non-biobased SAP | 48.1 | 29.1 |
| 50/50 SAP B w/w/ commercial non-biobased SAP | 47.0 | 28.6 |

Example 18: First Surface Crosslinked & Interior Crosslinked Charge Modified Starch and Surface Crosslinked & Second Interior Crosslinked Charge Modified Starch In an alternate synthesis path, the surface crosslinked and interior crosslinked charge modified starch from Table 54, synthesized from Crosslinker A and Crosslinker B w/w, was synthesized and mixed with commercial non-biobased SAP in ratios of 35:65, 30:70, and 25:75 by weight. An additional superabsorbent blend was made using a 35:65 ratio of the surface crosslinked and interior crosslinked charge modified starch synthesized using just Crosslinker A and commercial non-biobased SAP.

The resulting performance of each blend type is presented in Table 59 below.

TABLE 59

| Superabsorbent Used | FSC of Pure SA, g/g | CRC of Pure SA, g/g |
|---|---|---|
| 35/65 SAP A w/w/ commercial non-biobased SAP | 48.3 | 28.4 |
| 35/65 SAP C w/w/ commercial non-biobased SAP | 45.3 | 27.5 |
| 30/70 SAP C w/w/ commercial non-biobased SAP | 47.1 | 28.4 |
| 25/75 SAP C w/w/ commercial non-biobased SAP | 48.9 | 29.3 |

Example 19: Surface Crosslinked and Interior Crosslinked Charge Modified Starch Synthesized Using Crosslinker A or B Used in the Creation of a Feminine Hygiene Pad A surface crosslinked interior crosslinked charge modified starch was taken and mixed with wood pulp fluff in a 25:75 ratio of SAP to fluff to create a superabsorbent core. The superabsorbent core was then then layered with a 22 grams per square meter top sheet and a 2 Mil polyethylene back sheet to create a feminine hygiene pad.

The physical properties of the feminine hygiene pad are presented in Table 60.

TABLE 60

| SAP:Fluff Ratio | SAP (g) | Fluff (g) | Pad Dimensions (cm) | Avg. Thickness (mm) | Density (+/−0.01) | Grams per Square Meter |
|---|---|---|---|---|---|---|
| 25:75 | 1 | 3 | 20 × 8 | 2.6 | 0.15 | 250 |

The feminine hygiene pad made with this surface cross-linked and interior crosslinked charge modified starch was then taken and tested against pads made in similar fashion but containing commercially available polyacrylic based SAPs, or SAP extracted from diaper cores to determine the strikethrough capacity of different liquids. The diaper used for SAP extraction was a Huggies Diaper made by Kimberly-Clark. Additionally, two other synthetic SAPs were tested, along with another modified biopolymer made according to the present invention. The liquids used were saline solution and the menses analogs FDA solution, defibrinated sheep's blood, and processed swine blood. To test the strikethrough capacity of these liquids, a plate with a circular cutout with a diameter of 4.25 cm in the center was placed over pad under analysis. Seven milliliters of menses simulant was introduced through a buret onto the pad being tested in the region of pad exposed by the cutout in the plate, and the time the pad took to fully absorb this amount in the area allotted by the tube was measured. This was repeated three times each time adding more simulant to the same area for a total of 21 mL being absorbed after the third test.

Tables 61 through 64 display the ability of each tested liquid to strikethrough, or penetrate, the analyzed pads.

TABLE 61

| SAP | Liquid Used | First Strikethrough (s) | Second Strikethrough (s) | Third Strikethrough (s) |
|---|---|---|---|---|
| Polyacrylic acid A | Defibrinated Sheep's Blood | 31 | 42 | 42 |
| Polyacrylic acid B | | 33 | 41 | 47 |
| SAP A | | 31 | 43 | 43 |
| Diaper extracted | | 33 | 38 | 41 |
| Synthetic SAP 1 | | 30 | 39 | 42 |
| Synthetic SAP 4 | | 31 | 43 | 43 |
| Modified biopolymer | | 30.3 | 43.6 | 49.6 |

TABLE 62

| SAP | Liquid Used | First Strikethrough (s) | Second Strikethrough (s) | Third Strikethrough (s) |
|---|---|---|---|---|
| Polyacrylic acid C | Processed Swine Blood | 43 | 55 | 99 |
| Diaper Extracted | | 55 | 61 | 78 |
| SAP A | | 50 | 120 | 130 |

TABLE 63

| SAP | Liquid Used | First Strikethrough (s) | Second Strikethrough (s) | Third Strikethrough (s) |
|---|---|---|---|---|
| Polyacrylic acid B | FDA | 33 | 51 | 65 |
| Polyacrylic acid A | | 37 | 56 | 79 |

TABLE 63-continued

| SAP | Liquid Used | First Strikethrough (s) | Second Strikethrough (s) | Third Strikethrough (s) |
|---|---|---|---|---|
| Commercial non-biobased SAP | | 35 | 49 | 65 |
| Diaper Extracted | | 37 | 47 | 57 |
| SAP A | | 37 | 58 | 68 |

TABLE 64

| SAP | Liquid Used | First Strikethrough (s) | Second Strikethrough (s) | Third Strikethrough (s) |
|---|---|---|---|---|
| Polyacrylic acid C | Saline | 30 | 32 | 37 |
| Polyacrylic acid A | | 30 | 30 | 30 |
| Commercial non-biobased SAP | | 30 | 30 | 30 |
| Diaper Extracted | | 30 | 31 | 31 |
| SAP A | | 30 | 31 | 34 |

A rewet under load test was also performed for each pad, using the same liquids as in the above tables. The pad under analysis was placed onto the base of a ring stand with an affixed ring clamp. Tubing was run from a peristaltic pump to the ring clamp affixed to the ring stand and placed inside the ring clamp. A scoopula was attached to the end of the tubing to keep the ring clamp from compressing the tubing and preventing liquid flow. Seven mL of the desired liquid was then pumped by the peristaltic pump from its own container and through the tubing so that it landed in the center of the feminine hygiene pad under analysis. A second absorbent article of known mass was then placed onto the saturated pad and a weight was placed on top of both articles. The weight was placed in a way to apply a pressure of 0.5 PSI over the second absorbent cloth. The second absorbent article was then massed to determine the amount of liquid taken from the feminine hygiene pad under analysis. In other words, tests were performed according to INDA Standards *NWSP 070.7.R2 and 070.8.R1, modified as necessary for the fluids described herein.

Tables 65-68 display the rewet properties of the analyzed pads

TABLE 65

| SAP | Liquid Used | First Rewet Under Load (g) | Second Rewet Under Load (g) | Third Rewet Under Load (g) |
|---|---|---|---|---|
| Polyacrylic acid A | Defibrinated Sheep's Blood | 1.7 | 3.0 | 3.8 |
| Commercial non-biobased SAP | | 2.0 | 3.5 | 4.1 |
| SAP A | | 2.0 | 3.2 | 4.2 |
| Diaper extracted | | 1.98 | 3.12 | 4.23 |
| Synthetic SAP 1 | | 2.47 | 3.41 | 4.39 |
| Synthetic SAP 4 | | 2.09 | 3.39 | 4.51 |

TABLE 65-continued

| SAP | Liquid Used | First Rewet Under Load (g) | Second Rewet Under Load (g) | Third Rewet Under Load (g) |
|---|---|---|---|---|
| Modified biopolymer | | 1.81 | 3.24 | 4.14 |

TABLE 66

| Pad | Liquid Used | First Rewet Under Load (g) | Second Rewet Under Load (g) | Third Rewet Under Load (g) |
|---|---|---|---|---|
| Polyacrylic acid C | Processed Swine Blood | 1.52 | 3.04 | 4.11 |
| Diaper Extracted | | 1.27 | 2.79 | 3.46 |
| SAP A | | 1.53 | 3.30 | 4.22 |

TABLE 67

| Pad | Liquid Used | First Rewet Under Load (g) | Second Rewet Under Load (g) | Third Rewet Under Load (g) |
|---|---|---|---|---|
| Polyacrylic acid C | FDA | 1.66 | 3.87 | 4.95 |
| Polyacrylic acid A | | 1.84 | 3.87 | 4.95 |
| Commercial non-biobased SAP | | 2.47 | 4.06 | 5.49 |
| Diaper Extracted | | 2.71 | 4.68 | 5.36 |
| SAP A | | 2.56 | 4.71 | 5.55 |

TABLE 68

| Pad | Liquid Used | First Rewet Under Load (g) | Second Rewet Under Load (g) | Third Rewet Under Load (g) |
|---|---|---|---|---|
| Polyacrylic acid C | Saline | 0.02 | 0.37 | 4.24 |
| Polyacrylic acid A | | 0.05 | 0.68 | 3.09 |
| Polyacrylamide A | | 1.28 | 3.72 | 4.29 |
| Diaper Extracted | | 0.05 | 2.35 | 4.16 |
| SAP A | | 0.06 | 2.19 | 4.3 |

In order to assess the ability of the absorbent article to wick blood, an inclined wicking test was performed on feminine hygiene pads utilizing a variety of the polymers as adsorbents and both defibrinated sheep's blood and menses analogs to FDA solution. In this test, the absorbent article is held on a board placed at a 30-degree tilt. The edge of the board is then dipped into approximately 400-500 ml of each menses simulant. The respective feminine hygiene pads were allowed to absorb for 30 minutes before measurements were collected. Measurements include the amount of total liquid absorbed during the time period as well as the distance the liquid traveled up the pad from the contact point of the liquid. Results for the respective polymers can be found in Table 74. Presented results are averages of 4 pads.

TABLE 69

| SAP Used | Defibrinated Sheep's Blood | | FDA Formulation | |
|---|---|---|---|---|
| | Wicking Distance (cm) | Wicking Absorption (g) | Wicking Distance (cm) | Wicking Absorption (g) |
| Polyacrylic acid A | 4.1 | 10.4 | 5.2 | 20.4 |
| Polyacrylamide A | 4.0 | 10.6 | 5.8 | 20.04 |
| SAP A | 4.1 | 13.6 | 6.2 | 18.4 |

The wicking rate of the pad incorporating the surface crosslinked and interior crosslinked biobased SAP was also compared to the wicking rate of a pad including polyacrylic acid.

Figure 16:
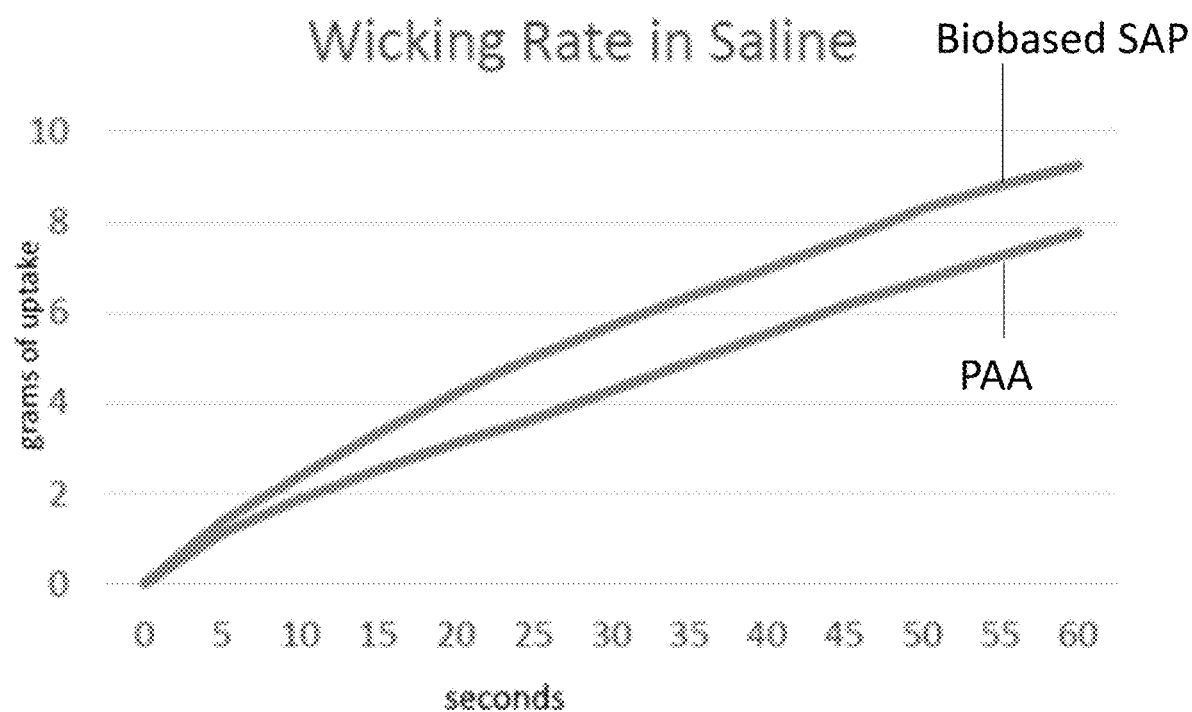
FIG. 16 illustrates a graph of the wicking rate of a menstrual pad including a biodegradable SAP and a menstrual pad including PAA.

FIG. 16 illustrates a graph of the wicking rate of a menstrual pad including a biodegradable SAP and a menstrual pad including PAA. For this testing, an adaptation of NWSP 10.1 is used to assess the capillarity, or rate at which liquid is transported into the prototype core at a 30-degree incline. The core is weighed and placed on an inclined tray with a grate suspending the core in the test liquid that is located in a reservoir on a 2 pt scale. The scale is connected via USB port to a computer where the negative scale balance is recorded every second for 1800 seconds. After a duration of 30 minutes, the distance the liquid has permeated is measured using a ruler affixed to the tray. The negative balance of the scale is recorded as the total absorption. The rate of wicking is determined by plotting the uptake per second for 1800 seconds and determining the line of best fit for the linear and exponential portions of the graph. Notably, the wicking rate of the modified biopolymer of the present invention is faster, e.g. the modified biopolymer uptakes more grams of saline, for at least the first 60 seconds compared to a polyacrylic acid based synthetic SAP.

A surface crosslinked and interior crosslinked charge modified starch was also turned into a powder. Several commercially available SAPs were also turned into powder. The free swell capacity of the surface crosslinked and interior crosslinked charge modified starch was tested against the commercial SAPs using 0.9% saline solution and the menses simulants ASTM synthetic blood, FDA, processed swine blood, and defibrinated sheep's blood.

Tables 70 through 74 display the free swell capacity of the interior crosslinked charge modified starch against the commercially available SAPs.

TABLE 70

| SAP | Liquid | Free Swell Capacity (g/g) |
|---|---|---|
| Polyacrylic acid A | Saline | 66 |
| Polyacrylamide A | | 59 |
| Commercial non-biobased SAP | | 56 |
| Polyacrylic acid D | | 51 |
| SAP A | | 32 |

TABLE 71

| SAP | Liquid | Free Swell Capacity (g/g) |
|---|---|---|
| Polyacrylic acid A | ASTM | 58 |
| Polyacrylamide A | Synthetic | 57 |
| Commercial non-biobased SAP | Blood | 53 |
| Polyacrylic acid D | | 51 |
| SAP A | | 29 |

TABLE 72

| SAP | Liquid | Free Swell Capacity (g/g) |
|---|---|---|
| Polyacrylic acid A | FDA | 49 |
| Polyacrylamide A | | 48 |
| Commercial non-biobased SAP | | 38 |
| Polyacrylic acid D | | 38 |
| SAP A | | 26 |

TABLE 73

| SAP | Liquid | Free Swell Capacity (g/g) |
|---|---|---|
| Polyacrylic acid A | Processed | 8 |
| Polyacrylamide A | Swine | 31 |
| Commercial non-biobased SAP | Blood | 12 |
| Polyacrylic acid D | | 26 |
| SAP A | | 22 |

TABLE 74

| SAP | Liquid | Free Swell Capacity (g/g) |
|---|---|---|
| Polyacrylic acid A | Defibrinated | 7 |
| Polyacrylamide A | Sheep's | 20 |
| Commercial non-biobased SAP | Blood | 13 |
| Polyacrylic acid D | | 15 |
| SAP A | | 24 |

Example 20: Surface Crosslinked and Interior Crosslinked Charge Modified Starch Synthesized Using Crosslinker A or B Used in the Creation of a Feminine Hygiene Pad The surface crosslinked and interior crosslinked charge modified starch was taken and mixed with wood pulp fluff in a 25:75 ratio of SAP to fluff to create a superabsorbent core. The superabsorbent core was then then layered with a 22 grams per square meter top sheet and a 2 Mil polyethylene back sheet to create a feminine hygiene pad. The feminine hygiene pad was made to the same specifications as Example 19. The same tests were performed and compared to the results of the multi-step process. The results of these tests can be found in Tables 75-78. Unless otherwise noted, the liquid used to obtain the results was defibrinated sheep blood.

TABLE 75

| SAP | Liquid | Free Swell Capacity (g/g) |
|---|---|---|
| Saline | SAP A | 32 |
| | SAP A formed via alternative process | 21 |
| Defibrinated Sheep's Blood | SAP A | 24 |
| | SAP A formed via alternative process | 14 |
| FDA | SAP A | 26 |
| | SAP A formed via alternative process | 18 |

TABLE 76

| SAP | Wicking Distance | Wicking Absorption |
|---|---|---|
| SAP A | 4.1 | 13.6 |
| SAP A formed via alternative process | 6.3 | 18.5 |

TABLE 77

| SAP | First Strikethrough (s) | Second Strikethrough (s) | Third Strikethrough (s) |
|---|---|---|---|
| SAP A | 31 | 43 | 43 |
| SAP A formed via alternative process | 31 | 39 | 39 |

TABLE 78

| SAP | First Rewet Under Load (g) | Second Rewet Under Load (g) | Third Rewet Under Load (g) |
|---|---|---|---|
| SAP A | 2.0 | 3.2 | 4.2 |
| SAP A formed via alternative process | 1.8 | 3.0 | 4.2 |

Example 21: Menses Absorption Performance of SAP A, SAP B, and SAP D

The surface crosslinked and interior crosslinked charge modified starches were ground into a powder.

The free swell capacity of the above three surface crosslinked and interior crosslinked charge modified starches were tested using saline solution and defibrinated sheep's blood. The results of these tests are presented in Tables 79 and 80.

TABLE 79

| SAP | Liquid | Free Swell Capacity (g/g) |
|---|---|---|
| SAP A | Saline | 30 |
| SAP B | | 36 |
| SAP D | | 36 |

TABLE 80

| SAP | Liquid | Free Swell Capacity (g/g) |
|---|---|---|
| SAP A | Defibrinated Sheep's Blood | 23 |
| SAP B | | 27 |
| SAP D | | 27 |

Example 22: Performance of Feminine Hygiene Pad Core Containing Interior Crosslinked Charge Modified Starch SAP A was taken and used in an air laying process to produce a feminine hygiene pad core that had a SAP: fluff ratio of 10:90, with SAP weighing 0.3 g, fluff weighing 3 g, a density of 0.23 g/cm$^3$, a GSM of 205, and dimensions of 20 cm×8 cm. These pads were placed in MONETERY BAY FILL YOUR OWN TEA BAGS "Tea Pot Size" tea bags in the event that the cutout dissolved during testing. Free swell capacity and centrifuge retention capacity tests were then performed on this core using saline solution, ASTM F1670, and defibrinated sheep's blood as menses simulants. The performance of this core was compared against a commercially available core.

The results of these tests are presented in Tables 81 through 86.

TABLE 81

| Core Type | Menses Simulant | FSC (g/g) |
|---|---|---|
| Pad Containing SAP A | Saline | 12.7 |
| Pad Containing Polyacrylic Acid SAP | | 15.5 |

TABLE 82

| Core Type | Menses Simulant | FSC (g/g) |
|---|---|---|
| Pad Containing SAP A | ASTM F1670 | 14.2 |
| Pad Containing Polyacrylic Acid SAP | | 17 |

TABLE 83

| Core Type | Menses Simulant | FSC (g/g) |
|---|---|---|
| Pad Containing SAP A | Defibrinated Sheep's Blood | 12.87 |
| Pad Containing Polyacrylic Acid SAP | | 12.7 |

TABLE 84

| Core Type | Menses Simulant | CRC (g/g) |
|---|---|---|
| Pad Containing SAP A | Saline | 5.6 |
| Pad Containing Polyacrylic Acid SAP | | 6.7 |

TABLE 85

| Core Type | Menses Simulant | CRC (g/g) |
|---|---|---|
| Pad Containing SAP A | ASTM F1670 | 4.4 |
| Pad Containing Polyacrylic Acid SAP | | 5.9 |

TABLE 86

| Core Type | Menses Simulant | CRC (g/g) |
|---|---|---|
| Pad Containing SAP A | Defibrinated Sheep's Blood | 4.9 |
| Pad Containing Polyacrylic Acid SAP | | 5.5 |

The liquid absorption capacity of the pad core including SAP A was also tested against the pad containing polyacrylic acid based SAP. To perform the liquid absorption capacity test, the core under analysis was taken and clamped to a square metal wire mesh with clothes line pins. The clamped core pad was then placed in a container of menses simulant to soak until it reached saturation equilibrium. The clamped core pad was massed before and after soaking, and the ratio of the two masses taken to determine the liquid absorption capacity. NWSP 10.1.RO (15) was modified to include a 10-minute soak time. Saline solution, ASTM F1670, and defibrinated sheep's blood were used as menses simulants. The core punchouts used in these tests had a SAP: Fluff ratio of 10:90, 0.3 grams of SAP, 3 grams of fluff, a density of 23 g/cm$^3$, and a GSM of 205. The FSC and CRC were also determined.

The results of these tests are detailed below in Tables 87 through 89.

TABLE 87

| Core Type | Menses Simulant | Liquid Absorption Capacity (%) | Avg FSC (g/g) | Avg CRC (g/g) |
|---|---|---|---|---|
| Pad Containing SAP A | Saline Solution | 1126% | 12.72 | 5.57 |
| Pad Containing Polyacrylic Acid SAP | | 1302% | 15.23 | 6.71 |

TABLE 88

| Core Type | Menses Simulant | Liquid Absorption Capacity (%) | Avg FSC (g/g) | Avg CRC (g/g) |
|---|---|---|---|---|
| Pad Containing SAP A | ASTM F1670 | 1325% | 14.24 | 4.40 |
| Pad Containing Polyacrylic Acid SAP | | 1481% | 17.00 | 5.89 |

TABLE 89

| Core Type | Menses Simulant | Liquid Absorption Capacity (%) | Avg FSC (g/g) | Avg CRC (g/g) |
|---|---|---|---|---|
| Pad Containing SAP A | Defibrinated Sheep's Blood | 1153% | 12.87 | 4.86 |
| Pad Containing Polyacrylic Acid SAP | | 1144% | 13.70 | 5.51 |

Next, the diffusion performance of the pad core was measured against the pad core containing PAA. To measure the diffusion performance, a whole pad core was taken and placed on top of a massing station, under a burette fixed to a ring clamp. The burette was filled with menses simulant then 7 mL of the simulant was dispensed onto the pad core under analysis. The pad core was aligned under the burette so that menses simulant dripped onto the center of the pad core. Saline solution, ASTM F1670, and defibrinated sheep's blood were used as menses simulants. The section of pad containing the absorbed menses simulant was cut out and massed to obtain a diffusion % by weight metric.

The results of these tests are detailed below in Tables 90 through 92.

TABLE 90

| Core Type | Menses Simulant | Diffusion % by Weight |
|---|---|---|
| Pad Containing SAP A | Saline Solution | 31% |
| Pad Containing Polyacrylic Acid SAP | | 38% |

TABLE 91

| Core Type | Menses Simulant | Diffusion % by Weight |
|---|---|---|
| Pad Containing SAP A | ASTM F1670 | 28% |
| Pad Containing Polyacrylic Acid SAP | | 29% |

TABLE 92

| Core Type | Menses Simulant | Diffusion % by Weight |
|---|---|---|
| Pad Containing SAP A | Defibrinated Sheep's Blood | 20% |
| Pad Containing Polyacrylic Acid SAP | | 20% |

The wicking performance of the pad core was also tested against PAA. To determine the wicking performance, an inclined wicking test was performed where the pad core under analysis was held on a board placed at a 30-degree tilt. The edge of the board was then dipped into approximately 400-500 mL of the menses simulant. The respective feminine hygiene pads cores were allowed to absorb for 30 minutes before measurements were collected. Measurements include the amount of total liquid absorbed during the time period as well as the distance the liquid traveled up the pad from the contact point of the liquid. Saline solution, ASTM F1670, and defibrinated sheep's blood.

The results of these tests are the averages of 4 pads, and are presented below in Tables 93 through 95.

TABLE 93

| Core Type | Menses Simulant | Distance Wicked (cm) | Uptake (g) |
|---|---|---|---|
| Pad Containing SAP A | Saline Solution | 17.0 | 23.9 |
| Pad Containing Polyacrylic Acid SAP | | 17.0 | 26.2 |

TABLE 94

| Core Type | Menses Simulant | Distance Wicked (cm) | Uptake (g) |
|---|---|---|---|
| Pad Containing SAP A | ASTM F1670 | 12.3 | 15.9 |
| Pad Containing Polyacrylic Acid SAP | | 12.0 | 18.1 |

TABLE 95

| Core Type | Menses Simulant | Distance Wicked (cm) | Uptake (g) |
|---|---|---|---|
| Pad Containing SAP A | Defibrinated Sheep's Blood | 9.8 | 15.9 |
| Pad Containing Polyacrylic Acid SAP | | 8.8 | 14 |

The final tests conducted on the pads were strikethrough testing and rewet under load testing. These tests were performed using the same procedures as Example 20. The results of these tests can be found in Table 96 through Table 101.

TABLE 96

| Pad | Liquid Used | First Strike-through(s) | Second Strike-through(s) | Third Strike-through(s) |
|---|---|---|---|---|
| Pad Containing SAP A | Defibrinated Sheep's Blood | 46 | 102 | 129 |
| Pad Containing Polyacrylic Acid SAP | | 74 | 123 | 156 |

TABLE 97

| Pad | Liquid Used | First Strike-through(s) | Second Strike-through(s) | Third Strike-through(s) |
|---|---|---|---|---|
| Pad Containing SAP A | Saline | 30 | 30 | 30 |
| Pad Containing Polyacrylic Acid SAP | | 30 | 30 | 30 |

TABLE 98

| Pad | Liquid Used | First Strike-through(s) | Second Strike-through(s) | Third Strike-through(s) |
|---|---|---|---|---|
| Pad Containing SAP A | ASTM F1670 | 49 | 92 | 97 |
| Pad Containing Polyacrylic Acid SAP | | 58 | 67 | 69 |

TABLE 99

| Pad | Liquid Used | First Rewet Under Load (g) | Second Rewet Under Load (g) | Third Rewet Under Load (g) |
|---|---|---|---|---|
| Pad Containing SAP A | Defibrinated Sheep's Blood | 0.60 | 1.82 | 2.66 |
| Pad Containing Polyacrylic Acid SAP | | 0.81 | 2.22 | 3.36 |

TABLE 100

| Pad | Liquid Used | First Rewet Under Load (g) | Second Rewet Under Load (g) | Third Rewet Under Load (g) |
|---|---|---|---|---|
| Pad Containing SAP A | Saline | 0.33 | 1.50 | 5.14 |
| Pad Containing Polyacrylic Acid SAP | | 0.14 | 0.59 | 3.68 |

TABLE 101

| Pad | Liquid Used | First Rewet Under Load (g) | Second Rewet Under Load (g) | Third Rewet Under Load (g) |
|---|---|---|---|---|
| Pad Containing SAP A | ASTM F1670 | 0.46 | 2.29 | 3.29 |
| Pad Containing Polyacrylic Acid SAP | | 0.19 | 2.05 | 2.66 |

Example 23: Performance of Feminine Hygiene Pad Prototype Containing Interior Crosslinked Charge Modified Starch An interior crosslinked charge modified starch was integrated into a core in a ratio of 25:75 SAP: Fluff. The total core weight was approximately 4 grams, with a density of 0.15 g/cm$^3$. The prototype included a 12 GSM top sheet, a 2-mil polyethylene back sheet, and the core. The prototype was tested according to the procedures outlined above, including strikethrough and rewet under load, in several solutions including processed swine blood (PSB), an FDA menses simulant, defibrinated sheep's blood (DSB), and a 0.9% NaCl solution. The results of the primary, secondary, and tertiary strikethrough tests, and the primary, secondary, and tertiary rewet under load (RUL) tests are outlined in Table 102 and Table 103, respectively.

TABLE 102

| Solution | Avg ST-P (s) | Avg ST-S (s) | Avg ST-T (s) |
|---|---|---|---|
| PSB | 53 | 89 | 139 |
| FDA | 37 | 58 | 68 |
| DSB | 30 | 35 | 35 |
| Saline | 30 | 31 | 34 |

TABLE 103

| Solution | Avg RUL-P (g) | Avg RUL-S (g) | Avg RUL-T (g) |
|---|---|---|---|
| PSB | 2.12 | 3.39 | 4.33 |
| FDA | 2.56 | 4.71 | 5.55 |
| DSB | 2.73 | 4.31 | 5.22 |
| Saline | 1.28 | 3.72 | 4.29 |

Example 24: Performance of Feminine Hygiene Pad Prototype Containing the Interior Crosslinked Charge Modified Starch Compared to Feminine Hygiene Pad Containing Synthetic SAP and Feminine Hygiene Pad with No SAP An interior crosslinked charge modified starch was integrated into a core in a ratio of 25:75 SAP: Fluff. The total core weight was approximately 4 grams, with a density of 0.15 g/cm$^3$. The prototype included a 12 GSM top sheet, a 2-mil polyethylene back sheet, and the core. Two additional pads were constructed, with the first additional pad utilizing a synthetic SAP but otherwise having the same SAP: Fluff ratio, weight, density, and composition of the prototype. The second additional pad did not include SAP, but was otherwise the same weight, density, and composition of the prototype. These pads was tested to determine strikethrough time and rewet under load, in defibrinated sheep's blood and the FDA menses simulant.

The results of the primary, secondary, and tertiary strikethrough tests, and the primary, secondary, and tertiary rewet under load (RUL) tests are outlined in Table 104 and Table 105, respectively.

TABLE 104

| Solution | SAP | Avg ST-P (s) | Avg ST-S (s) | Avg ST-T (s) |
|---|---|---|---|---|
| DSB | Synthetic | 31 | 43 | 43 |
| DSB | Modified biopolymer | 30 | 35 | 35 |
| DSB | None | 30 | 39 | 51 |
| FDA | Synthetic | 35 | 49 | 65 |
| FDA | Modified biopolymer | 37 | 58 | 68 |
| FDA | None | 36 | 46 | 48 |

TABLE 105

| Solution | SAP | Avg RUL-P (g) | Avg RUL-S (g) | Avg RUL-T (g) |
|---|---|---|---|---|
| DSB | Synthetic | 2.09 | 3.39 | 4.51 |
| DSB | Modified biopolymer | 2.73 | 4.31 | 5.22 |
| DSB | None | 1.3 | 3.0 | 4.3 |
| FDA | Synthetic | 2.47 | 4.06 | 5.49 |

TABLE 105-continued

| Solution | SAP | Avg RUL-P (g) | Avg RUL-S (g) | Avg RUL-T (g) |
|---|---|---|---|---|
| FDA | Modified biopolymer | 2.56 | 4.71 | 5.55 |
| FDA | None | 2.8 | 5.1 | 6.1 |

Example 25: Wicking Performance of Prototype Containing the Interior Crosslinked Charge Modified Starch Compared to Pad Containing Synthetic SAP An interior crosslinked charge modified starch was integrated into a core in a ratio of 25:75 SAP: Fluff. The total core weight was approximately 4 grams, with a density of 0.15 g/cm$^3$. The prototype incontinence pad included a 12 GSM top sheet, a commercial incontinence ADL, a 2-mil polyethylene back sheet, and the core. A first additional incontinence pad was provided, with the first additional pad utilizing a synthetic SAP but otherwise having the same SAP: Fluff ratio, weight, density, and composition of the prototype. A second additional commercially available incontinence pad was also provided. The wicking distance and wicking absorption results are outlined in Table 106.

TABLE 106

| Simulant | SAP | Wicking Distance (cm) | Wicking Absorption (g) |
|---|---|---|---|
| DSB | Synthetic | 4 | 10.6 |
| DSB | Modified biopolymer | 4.1 | 13.6 |
| FDA | Synthetic | 5.8 | 20.4 |
| FDA | Modified biopolymer | 6.2 | 18.4 |

Example 26: Performance of Core Containing Interior Crosslinked Charge Modified Starch Compared to Core Containing Synthetic SAP An interior crosslinked charge modified starch was integrated into a core in a ratio of 20:80 SAP: Fluff. The total core weight was approximately 5 grams, with a density of 0.10 g/cm$^3$. An additional core was constructed, with the first additional core utilizing a synthetic SAP but otherwise having the same SAP: Fluff ratio, weight, density, and composition of the prototype. These cores were tested according to the wicking procedure described above in defibrinated sheep's blood and the FDA menses simulant.

The acquisition time under load weighted swell (ATULWS) and the rewet under load weighted swell (RULWS) of these pads was determined in 0.9% NaCl. The ATULWS and RULWS are displayed in Table 107.

TABLE 107

| | ATULWS-P (s) | ATULWS-S (s) | RULWS-P (g) | RULWS-S (g) |
|---|---|---|---|---|
| Commercial Control | 8 | 20 | 1.98 | 10.94 |
| Synthetic SAP | 8 | 37 | 2.31 | 8.94 |
| Modified Biopolymer | 8 | 40 | 5.39 | 9.92 |

Example 27: Performance of SAP Powders in Menses Simulants

The free swell capacity and centrifuge retention capacity of the modified biopolymer formed according to the present invention, synthetic SAPs, and a SAP extracted from a commercially available diaper were tested. The results are presented in Tables 108-111 below.

TABLE 108

| SAP | FDA FSC (g/g) | Defibrinated Sheep's Blood FSC (g/g) |
|---|---|---|
| Polyacrylic acid C | 53 | 5 |
| Diaper Extracted | 39 | 30 |
| Polyacrylic acid A | 49 | 7 |
| Polyacrylamide A | 48 | 20 |
| Commercial non-biobased SAP | 38 | 13 |
| Polyacrylic acid D | 38 | 15 |
| Biobased SAP | 21 | 18 |

TABLE 109

| SAP | FDA CRC (g/g) | Defibrinated Sheep's Blood CRC (g/g) |
|---|---|---|
| Polyacrylic acid C | 35 | 4 |
| Diaper Extracted | 24 | 18 |
| Polyacrylic acid A | 31 | 5 |
| Polyacrylamide A | 27 | 11 |
| Commercial non-biobased SAP | 27 | 10 |
| Polyacrylic acid D | 28 | 13 |
| Biobased SAP | 15 | 13 |

TABLE 110

| SAP | 0.9% NaCl FS (g/g) | FDA FSC (g/g) | Defibrinated Sheep's Blood FSC (g/g) |
|---|---|---|---|
| Polyacrylic acid C | 68 | 53 | 5 |
| Polyacrylic acid D | 51 | 38 | 15 |
| Biobased SAP | 18 | 21 | 18 |

TABLE 111

| SAP | 0.9% NaCl CRC (g/g) | FDA CRC (g/g) | Defibrinated Sheep's Blood CRC (g/g) |
|---|---|---|---|
| Polyacrylic acid C | 35 | 35 | 4 |
| Polyacrylic acid D | 34 | 28 | 13 |

TABLE 111-continued

| SAP | 0.9% NaCl CRC (g/g) | FDA CRC (g/g) | Defibrinated Sheep's Blood CRC (g/g) |
|---|---|---|---|
| Biobased SAP | 8 | 15 | 13 |

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

What is claimed is:

1. A disposable absorbent sanitary article, comprising:
a fluid-permeable top layer;
a fluid-resistant back layer; and
an absorbent core;
wherein the absorbent core includes a biocompostable superabsorbent polymer (SAP);
wherein the SAP includes a modified starch-based biopolymer;
wherein the modified starch-based biopolymer is surface and interior crosslinked;
wherein the modified starch-based biopolymer includes a charge modified starch-based biopolymer including at least one negatively charged moiety;
wherein epichlorohydrin is not used as a crosslinking agent during synthesis of the modified starch-based biopolymer;
wherein the SAP exhibits no cytotoxicity and is not a dermal irritant;
wherein a biobased carbon content of the SAP is at least 80%;
wherein the modified starch-based biopolymer has a Free Swell Capacity (FSC) of at least 18 g/g and a Centrifuge Retention Capacity (CRC) of at least 13 g/g in defibrinated sheep's blood; and
wherein the liquid absorption capacity of the article is at least 1150% in defibrinated sheep's blood.

2. The article of claim 1, wherein the SAP does not include a synthetic polymer and does not include a graft polymer.

3. The article of claim 1, wherein the wicking uptake of the absorbent core is at least 15 grams in defibrinated sheep's blood.

4. The article of claim 1, wherein the article is a menstrual pad.

5. The article of claim 1, wherein a ratio of the SAP to fluff in the absorbent core is 10 to 90.

6. The article of claim 1, wherein a ratio of the SAP to fluff in the absorbent core is 25 to 75, and wherein the primary rewet under load of the article is less than 2.0 grams in defibrinated sheep's blood according to modified NWSP 070.8.R1.

7. The article of claim 6, wherein the secondary rewet under load of the article is less than 3.50 grams in defibrinated sheep's blood according to modified NWSP 070.8.R1.

8. The article of claim 7, wherein the tertiary rewet under load of the article is less than 4.50 grams in defibrinated sheep's blood according to modified NWSP 070.8.R1.

9. The article of claim 1, wherein a ratio of the SAP to fluff in the absorbent core is 10 to 90, with the absorbent core having a density of 0.23 g/cm3.

10. The article of claim 1, wherein the modified starch-based biopolymer is formed using at least two different crosslinking agents.

11. A disposable absorbent sanitary article, comprising:
a fluid-permeable top layer;
a fluid-resistant back layer; and
an absorbent core;
wherein the absorbent core includes a biocompostable superabsorbent polymer (SAP);
wherein the SAP includes a modified biopolymer;
wherein the modified biopolymer is surface and interior crosslinked;
wherein the modified biopolymer includes a charge modified starch-based biopolymer including at least one negatively charged moiety;
wherein epichlorohydrin is not used as a crosslinking agent during synthesis of the modified biopolymer;
wherein the SAP exhibits no cytotoxicity and is not a dermal irritant wherein a biobased carbon content of the SAP is at least 84%; and
wherein the primary rewet under load of the article is less than 2.00 grams and the secondary rewet under load of the article is less than 3.50 grams in defibrinated sheep's blood according to modified NWSP 070.8.R1.

12. The article of claim 11, wherein a ratio of the SAP to fluff in the absorbent core is 10 to 90, with the absorbent core having a density of 0.23 g/cm$^3$.

13. The article of claim 11, wherein the liquid absorption capacity of the article is at least 1300% in ASTM F1670.

14. The article of claim 11, wherein the wicking uptake of the absorbent core is at least 15 grams in defibrinated sheep's blood.

15. The article of claim 11, wherein the modified biopolymer has a Free Swell Capacity (FSC) of at least 18 g/g and a Centrifuge Retention Capacity (CRC) of at least 13 g/g in defibrinated sheep's blood.

16. A disposable absorbent sanitary article, comprising:
a fluid-permeable top layer;
a fluid-resistant back layer; and
an absorbent core;
wherein the absorbent core includes a biocompostable superabsorbent polymer (SAP);
wherein the SAP includes a modified starch-based biopolymer;
wherein the SAP is biobased;
wherein the modified starch-based biopolymer is surface and interior crosslinked;
wherein the modified starch-based biopolymer includes a charge modified starch-based biopolymer including at least one negatively charged moiety;
wherein epichlorohydrin is not used as a crosslinking agent during synthesis of the modified starch-based biopolymer;
wherein the SAP exhibits no cytotoxicity and is not a dermal irritant;
wherein the SAP does not include a synthetic SAP;
wherein the SAP does not include a graft polymer; and
wherein the modified starch-based biopolymer has a Free Swell Capacity (FSC) of at least 18 g/g and a Centrifuge Retention Capacity (CRC) of at least 13 g/g in defibrinated sheep's blood.

17. The article of claim 1, wherein the modified starch-based biopolymer is synthesized by producing a starch-based biopolymer through reactive extrusion using a charge modifying agent and a plasticizer, performing interior crosslinking on the starch-based biopolymer, coating the interior crosslinked starch-based biopolymer with a surface crosslinking agent, and thermally treating the interior crosslinked starch-based biopolymer to create surface crosslinks on the interior crosslinked, charge modified starch-based biopolymer.

18. The article of claim 1, wherein an alcohol is not used in a charge modification step of an extrusion process in making the modified starch-based biopolymer.

19. The article of claim 1, wherein at least 85% of the particle sizes of the modified biopolymer are between 100 micrometers and 850 micrometers.

20. The article of claim 16, wherein the modified starch-based biopolymer is synthesized by producing a starch-based biopolymer through reactive extrusion using a charge modifying agent and a plasticizer, performing interior crosslinking on the starch-based biopolymer, coating the interior crosslinked starch-based biopolymer with a surface crosslinking agent, and thermally treating the interior crosslinked starch-based biopolymer to create surface crosslinks on the interior crosslinked, charge modified starch-based biopolymer.

* * * * *